(12) United States Patent
Nadal Roura

(10) Patent No.: US 10,155,708 B2
(45) Date of Patent: *Dec. 18, 2018

(54) METHODS OF PURIFYING CANNABINOIDS, COMPOSITIONS AND KITS THEREOF

(71) Applicant: Phytoplant Research S.L., Córdoba (ES)

(72) Inventor: Xavier Nadal Roura, Córdoba (ES)

(73) Assignee: Phytoplant Research S.L., Cordoba (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,524

(22) Filed: Sep. 18, 2017

(65) Prior Publication Data

US 2018/0000879 A1  Jan. 4, 2018

Related U.S. Application Data

(63) Continuation-in-part of application No. 15/004,848, filed on Jan. 22, 2016, now Pat. No. 9,765,000.

(Continued)

(51) Int. Cl.
| | |
|---|---|
| *C07C 37/84* | (2006.01) |
| *A61K 36/18* | (2006.01) |
| *B01D 11/04* | (2006.01) |
| *C07B 63/00* | (2006.01) |
| *A61K 36/185* | (2006.01) |
| *C07C 37/00* | (2006.01) |

(Continued)

(52) U.S. Cl.
CPC ............. *C07C 37/84* (2013.01); *A61K 36/18* (2013.01); *A61K 36/185* (2013.01); *B01D 11/0403* (2013.01); *C07B 63/00* (2013.01); *C07C 37/004* (2013.01); *A61K 31/047* (2013.01); *A61K 31/352* (2013.01); *A61K 2236/00* (2013.01); *C07B 2200/13* (2013.01); *C07C 2601/16* (2017.05); *C07D 311/78* (2013.01); *G01N 2030/027* (2013.01)

(58) Field of Classification Search
CPC ..... B01D 11/04; B01D 11/0403; C07C 51/43; C07C 37/84; C07C 37/685; C07B 63/00; A61K 36/18; A61K 36/185
See application file for complete search history.

(56) References Cited

U.S. PATENT DOCUMENTS 7,700,368 B2   4/2010  Flockhart et al.

FOREIGN PATENT DOCUMENTS

| EP | 2044935 A1 | 4/2009 |
|---|---|---|
| GB | 2393182 A | 3/2004 |

(Continued)

OTHER PUBLICATIONS

Nian Ling et al., The separation and identification of Δ9-tetrahydrocannabinol in cannabis, Research for Chinese Patent Medicine, Dec. 31, 1985, pp. 29-30, vol. 8, Shanghai Institute of Pharmaceutical Industry (Thesis), Shanghai, China.

*Primary Examiner* — Yate' K Cutliff
(74) *Attorney, Agent, or Firm* — Annette S. Parent

(57) ABSTRACT

The present specification discloses methods of purifying one or more cannabinoids from a plant material, purified cannabinoids and pharmaceutical compositions comprising one or more cannabinoids produced by the disclosed method, methods and uses for treating a disease or condition employing such purified cannabinoids and pharmaceutical compositions.

42 Claims, 3 Drawing Sheets

Related U.S. Application Data

(60) Provisional application No. 62/106,644, filed on Jan. 22, 2015.

(51) Int. Cl.
    *G01N 30/02*     (2006.01)
    *A61K 31/047*     (2006.01)
    *A61K 31/352*     (2006.01)
    *C07D 311/78*     (2006.01)

(56) References Cited

FOREIGN PATENT DOCUMENTS

| | | | |
|---|---|---|---|
| WO | 2004026802 A1 | 4/2004 | |
| WO | 2004026857 A2 | 4/2004 | |
| WO | WO 2006/053766 * | 5/2006 | ........... A61K 31/353 |
| WO | 2006053766 A8 | 12/2006 | |

* cited by examiner

METHODS OF PURIFYING CANNABINOIDS, COMPOSITIONS AND KITS THEREOF

This application claims the benefit of priority and the filing date of U.S. Provisional Patent Application 62/106,644, filed on Jan. 22, 2015 and U.S. patent application Ser. No. 15/004,848, filed on Jan. 22, 2016, the contents of which are each hereby incorporated by reference in their entirety.

TECHNICAL FIELD

The present invention relates to the isolation of cannabinoid compounds.

BACKGROUND OF THE INVENTION

*Cannabis* is a genus of flowering plants whose species are distinguished by plant phenotypes and secondary metabolite profiles. At least three species are recognized, *Cannabis sativa, C. indica*, and *C. ruderalis*. *Cannabis* plants have been cultivated for a variety of uses including making fibers (hemp), medicinal use and recreational drug use. *Cannabis* is also commonly known as marijuana.

*Cannabis* has now been generally acknowledged as having substantial benefits for various medical uses. For example, *cannabis* is regularly used by a wide cross-section of society to treat a variety of maladies, ailments and symptoms including, but not limited to, nausea, pain relief (such as chronic pain, cancer related pain, or neuropathic pain), glaucoma, lack of appetite, mucous membrane inflammation, inflammatory diseases (such as Crohn's disease), neurodegenerative disease, epilepsy (that affects children and adults), seizures, diabetes, leprosy, fever, obesity, asthma, urinary tract infections, coughing, anorexia associated with weight loss in AIDS patients, graft-versus-host disease, glioma, perinatal asphyxia and post-traumatic stress disorder (PTSD) and autoimmune disease (such as multiple sclerosis).

One of the most common ways that *cannabis* is used for medicinal use in many countries is through smoking. Smoking medical *cannabis*, although proven to be beneficial in certain indications, has disadvantages. For example, the amounts of active ingredients may differ depending on the differences present in plant varietals as well as changing growing conditions which result in intravarietal variations. As a result, it can be difficult to maintain control over the proper dosing of medicinal *cannabis* due to active ingredients fluctuations. Another disadvantage of smoking medical *cannabis* is the negative impact of some of the constituents of *cannabis* smoke. The smoke from the plant matter comprise carcinogens in addition to the desired cannabinoids. In addition, heavy *cannabis* use through smoking has been associated with accelerated pulmonary decline.

Cannabinoids are compounds active on cannabinoid receptors in humans and are responsible for eliciting many of the pharmacological effects of *cannabis*. Cannabinoids of plant origin, also known as phytocannabinoids, are abundant in *Cannabis*. Two known cannabinoids which are present in relatively high concentrations in *Cannabis sativa* L. are tetrahydracannabinolacid (THCA) or its decarboxylated product tetrahydracannabinol (THC) and cannabidiolic acid (CBDA) or its decarboxylated product cannabidiol (CBD). THC elicits psychoactive (calming) effects, analgesic effects, antioxidant effects and to increase appetite. However, THC is also associated with many negative or undesirable side effects including, but are not limited to, decreased short-term memory, dry mouth, impaired visual perception and motor skills, erectile dysfunction, lower fertility, red (i.e., blood shot) eyes, increased anxiety, occasional infarction, stroke, paranoia, acute psychosis, lowered mental aptitude, hallucinations, bizarre behavior, irrational panic attacks, irrational thoughts and various other cognitive and social problems. On the other hand, CBD is increasingly becoming a popular cannabinoid for medicinal purposes because unlike THC, CBD is non-psychoactive at typical doses. In addition, CBD was found to have neuroprotective effects and to have ameliorative effects in patients with schizophrenia and Parkinson's disease. Accordingly, patients and healthcare providers are exhibiting a preference for CBD because patients need to work, drive and function with clarity while undergoing treatment.

Efforts have been made to reduce the amount THC in *cannabis* and cannabinoid products without significantly reducing the therapeutic effects of other nonpsychoactive cannabinoids. One way is to selectively breed *cannabis* varietals having an increased CBD:THC ratio. However, such *cannabis* varietals would still need to be administered by smoking, exposing the patient to its associated disadvantages and detrimental health effects. Another way to selectively manage or eliminate THC using a series of fractionating columns. Diverse chromatographic techniques have been used purify cannabinoid compounds from the plant *Cannabis sativa*. For example, Flash chromatography on silica gel, C8 or C18; preparative HPLC on silica gel columns, C8 or C18; and supercritical $CO_2$ chromatography on silica gel. However, these chromatographic processes are tedious and expensive.

Thus, what is needed is a simple and less expensive process that selectively purifies and concentrates medically beneficial cannabinoids from THC, thereby lowering THC content as a percentage of the cannabinoid mix. In addition, it is also desirous to develop medicinal formulations comprising higher levels of beneficial cannabinoids while at the same time having a lowered THC content.

The present disclosure solves these and other problems by providing a method for isolating and purifying cannabinoid compounds that does not use chromatographic steps. By means of this procedure it is possible to obtain high yields of cannabinoid compounds having a purity of 95% or more.

SUMMARY

Aspects of the present specification disclose methods of purifying one or more cannabinoids from a plant material. The disclosed methods comprising a) incubating the plant material with a first non-polar solvent to form a first solvent mixture which extracts the one or more cannabinoids from a plant material; b) reducing the volume of the first solvent mixture to about 50% or less of the original volume of the first solvent mixture in step (a) in a manner that concentrates the one or more cannabinoids; c) incubating the reduced first solvent mixture in a manner that crystallizes the one or more cannabinoids; d) incubating the one or more crystallized cannabinoids with a second non-polar solvent to form a second solvent mixture; and e) incubating the second solvent mixture in a manner that crystallizes the one or more cannabinoids, thereby resulting in the purification of one or more cannabinoids. The disclosed methods further provide that the one or more crystallized cannabinoids of step (c) may be purified prior to step (d), using, e.g., filtration that results in a collection of a mother liquor. The mother liquor may be collected reduced by evaporation and incubated in a manner that crystallizes the one or more cannabinoids.

Other aspects of the present specification disclose methods of purifying one or more cannabinoids from a plant material. The disclosed methods comprising a) incubating the plant material with a first non-polar solvent to form a first solvent mixture which extracts the one or more cannabinoids from a plant material; b) filtering the first solvent mixture; c) reducing the volume of the first solvent mixture to about 50% or less of the original volume of the first solvent mixture in step (a) in a manner that concentrates the one or more cannabinoids; d) incubating the reduced first solvent mixture in a manner that crystallizes the one or more cannabinoids; e) purifying the one or more crystallized cannabinoids in step (d) using filtration that results in a collection of a mother liquor; f) incubating the one or more crystallized cannabinoids with a second non-polar solvent to form a second solvent mixture; g) incubating the second solvent mixture in a manner that crystallizes the one or more cannabinoids; and h) purifying the one or more crystallized cannabinoids of step (g) using filtration that results in a collection of a mother liquor, thereby resulting in the purification of one or more cannabinoids. The disclosed methods may further comprising i) purifying the one or more crystallized cannabinoids using filtration that results in a collection of a mother liquor; and j) incubating the mother liquor in a manner that crystallizes the one or more cannabinoids. Steps (i) and (j), steps (f) and (g) and steps (f), (g) and (h) may be repeated one or more times.

Other aspects of the present specification disclose purified cannabinoids and pharmaceutical compositions comprising one or more cannabinoid produced by the disclosed methods.

Other aspects of the present specification disclose methods of treating a disease or condition using purified cannabinoids and pharmaceutical compositions comprising one or more cannabinoid produced by the disclosed methods. Non limiting examples of a disease or condition include pain, schizophrenia, convulsion, inflammation, anxiety, depression, neurodegenerative disease, stroke, traumatic brain injury, cancer, migraines, arthritis, chronic pain, nausea and vomiting, anorexia, glaucoma, glioma, epilepsy, asthma, perinatal asphyxia, graft-versus-hot disease, addiction, symptoms of dependency and withdrawal, multiple sclerosis, spinal cord injury, Tourette's syndrome, dystonia, or tardive dyskinesia.

DETAILED DESCRIPTION

Figure 1:
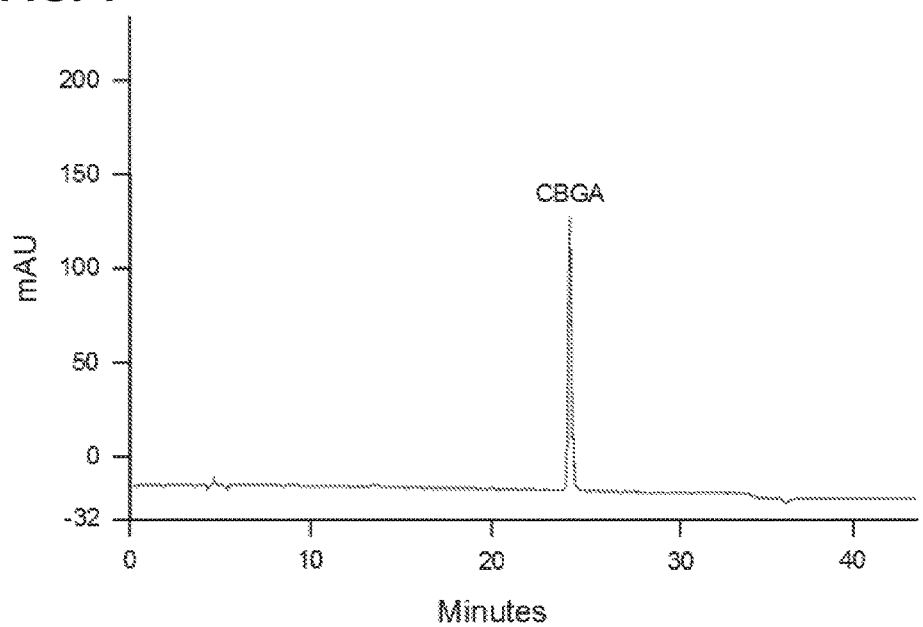
FIG. 1 shows a HPLC chromatogram at 270 nm of CBGA obtained in Example 4 with purity over 95% with normalized peak area.

The present invention provides a method for isolating and purifying one or more cannabinoids. Non-limiting examples of a cannabinoid include cannabigereol (CBG), cannabigerol acid (CBGA) or cannabidiol (CBD)) from a plant belonging to the genus *Cannabis*.

In one embodiment, a method of purifying one or more cannabinoids from a plant material comprises a) incubating the plant material with a first non-polar solvent to form a first solvent mixture which extracts the one or more cannabinoids from a plant material; b) reducing the volume of the first solvent mixture to about 50% or less of the original volume of the first solvent mixture in step (a) in a manner that concentrates the one or more cannabinoids; c) incubating the reduced first solvent mixture in a manner that crystallizes the one or more cannabinoids; d) incubating the one or more crystallized cannabinoids with a second non-polar solvent to form a second solvent mixture; and e) incubating the second solvent mixture in a manner that crystallizes the one or more cannabinoids, thereby resulting in the purification of one or more cannabinoids. The disclosed methods further provide that the one or more crystallized cannabinoids of step (c) may be purified prior to step (d), using, e.g., filtration that results in a collection of a mother liquor. The mother liquor may be collected and incubated in a manner that crystallizes the one or more cannabinoids. Step (a) may be repeated one or more times. Steps (d) and (e) may be repeated one or more times until the purity of the one or more cannabinoids is 95% or more.

In one embodiment, a method of purifying one or more cannabinoids from a plant material comprises a) incubating the plant material with a first non-polar solvent to form a first solvent mixture which extracts the one or more cannabinoids from a plant material; b) filtering the first solvent mixture; c) reducing the volume of the first solvent mixture to about 50% or less of the original volume of the first solvent mixture in step (a) in a manner that concentrates the one or more cannabinoids; d) incubating the reduced first solvent mixture in a manner that crystallizes the one or more cannabinoids; e) purifying the one or more crystallized cannabinoids in step (d) using filtration that results in a collection of a mother liquor; f) incubating the one or more crystallized cannabinoids with a second non-polar solvent to form a second solvent mixture, wherein the second solvent mixture dissolves at least 50% of the one or more crystallized cannabinoids; g) incubating the second solvent mixture in a manner that crystallizes the one or more cannabinoids; and h) purifying the one or more crystallized cannabinoids of step (g) using filtration that results in a collection of a mother liquor, thereby resulting in the purification of one or more cannabinoids. The disclosed methods may further comprising i) purifying the one or more crystallized cannabinoids using filtration that results in a collection of a mother liquor; and j) incubating the mother liquor in a manner that crystallizes the one or more cannabinoids. Step (a) may be repeated one or more times. Steps (i) and (j), steps (f) and (g) and steps (f), (g) and (h) may be repeated one or more times until the purity of the one or more cannabinoids is 95% or more.

In one embodiment, a method of purifying one or more cannabinoids from a plant material comprises a) incubating the plant material with a first non-polar solvent to form a first solvent mixture which extracts the one or more cannabinoids from a plant material; b) filtering the first solvent mixture; c) reducing by evaporation, the volume of the first non-polar solvent in the filtrate obtained in step (b); d) incubating the reduced first solvent mixture in a manner that crystallizes the one or more cannabinoids; e) removing the first non-polar solvent by vacuum filtering; f) further reducing the amount of first non-polar solvent from the filtrate of (e) by evaporation; g) incubating the one or more crystallized cannabinoids with a second non-polar solvent to form a second solvent mixture, wherein the second solvent mixture dissolves at least 50% of the one or more crystallized cannabinoids; h) incubating the second solvent mixture in a manner that crystallizes the one or more cannabinoids; i) removing the second non-polar solvent by vacuum filtering and saving the crystals obtained; and j) adding sufficient non-polar solvent per gram of cannabinoid to dissolve the crystals obtained in step (i) and recrystallizing.

Aspects of the present specification disclose, in part, incubating the plant material with a first non-polar solvent to form a first solvent mixture which extracts the one or more cannabinoids from a plant material. The extract obtained from a plant can be obtained by maceration in a non-polar solvent. A "non-polar solvent" as used herein includes a liquid non-polar solvent comprising lower $C_5$-$C_{12}$, or $C_5$-$C_8$ straight chain, or branched chain alkanes. Non-limiting examples of the non-polar solvent include pentane, hexane, petroleum ether (60-80° C. bp), cyclohexane, heptane, chloroform, benzene, toluene, or diethyl ether. In one embodiment, the non-polar solvent used in any one of or all of the present extraction steps is hexane. In one aspect of this embodiment, at least one of the extraction and/or purification steps for extraction of CBG and/or CBGA is performed with hexane. In another embodiment the non-polar solvent used in any one of or all of the present extraction steps is pentane or petroleum ether (40-60° C. bp). In one aspect of this embodiment, one or more of the extraction and/or purification steps for extraction/purification of CBD is performed with pentane or petroleum ether (40-60° C. bp).

Besides the particular non-polar solvent, extraction of the one or more cannabinoids from a plant material is a function of temperature, time and number of extraction steps. In aspects of this embodiment, incubating the plant material with a first non-polar solvent occurs for a time period of, e.g., at least 5 minutes, at least 10 minutes, at least 15 minutes, for at least 30 minutes, for at least 45 minutes, for at least 1 hour, for at least 1.25 hours, for at least 1.5 hours, for at least 1.75 hours, for at least 2 hours, for at least 2.25 hours, for at least 2.5 hours, for at least 2.75 hours, for at least 3.0 hours, for at least 3.25 hours, for at least 4.5 hours, for at least 4.75 hours, or for at least 5.0 hours. In other aspects of this embodiment, incubating the plant material with a first non-polar solvent occurs for a time period of, e.g., at most 5 hours, for at most 4.75 hours, for at most 4.5 hours, for at most 4.25 hours, for at most 4.0 hours, for at most 3.75 hours, for at most 3.5 hours, for at most 3.25 hours, for at most 3.0 hours, for at most 2.75 hours, for at most 2.5 hours, for at most 2.25 hours, for at most 2.0 hours, for at most 1.75 hours, for at most 1.5 hours, for at most 1.25 hours, for at most 1.25 hours, for at most 1.0 hours, for at most 45 minutes, for at most 30 minutes, or for at most 15 minutes. In yet other aspects of this embodiment, incubating the plant material with a first non-polar solvent occurs for a time period of, e.g., about 15 minutes to about 5 hours, about 30 minutes to about 5 hours, about 45 minutes to about 5 hours, about 1 hour to about 5 hours, about 1 hour to about 4 hours, about 1 hour to about 3.5 hours, about 1 hour to about 3.0 hours, about 1 hour to about 2.25 hours, about 1 hour to about 2 hours, about 1 hour to about 1.75 hours, about 1 hour to about 1.5 hours, about 30 minutes to about 1.5 hours, about 30 minutes to about 1.25 hours, about 30 minutes to about 1 hour, about 45 minutes to about 1.75 hours, about 45 minutes to about 1.5 hours, about 45 minutes to about 1.25 hours, or about 45 minutes to about 1 hour.

In aspects of this embodiment, incubating the plant material with a first non-polar solvent occurs at a temperature of, e.g., 0° C. or higher, 4° C. or higher, 8° C. or higher, 12° C. or higher, 16° C. or higher, 20° C. or higher or 24° C. or higher, 28° C. or higher, 32° C. or higher, 36° C. or higher, 40° C. or higher, 44° C. or higher, 48° C. or higher, 52° C. or higher, 56° C. or higher or 60° C. or higher. In other aspects of this embodiment, incubating the plant material with a first non-polar solvent occurs at a temperature of, e.g., 0° C. or lower, 4° C. or lower, 8° C. or lower, 12° C. or lower, 16° C. or lower, 20° C. or lower, 24° C. or lower, 28° C. or lower, 32° C. or lower, 36° C. or lower, 40° C. or lower, 44° C. or lower, 48° C. or lower, 52° C. or lower, 56° C. or lower or 60° C. or lower. In other aspects of this embodiment, incubating the plant material with a first non-polar solvent occurs at a temperature of, e.g., about 0° C. to about 4° C., about 0° C. to about 8° C., about 0° C. to about 12° C., about 0° C. to about 16° C., about 0° C. to about 20° C., about 0° C. to about 24° C., about 0° C. to about 28° C., about 0° C. to about 32° C., about 0° C. to about 36° C., about 0° C. to about 40° C., about 0° C. to about 44° C., about 0° C. to about 48° C., about 0° C. to about 52° C., about 0° C. to about 56° C., about 0° C. to about 60° C., about 4° C. to about 8° C., about 4° C. to about 12° C. about 4° C. to about 16° C., about 4° C. to about 20° C., about 4° C. to about 24° C., about 4° C. to about 28° C., about 4° C. to about 32° C., about 4° C. to about 36° C., about 4° C. to about 40° C., about 4° C. to about 44° C., about 4° C. to about 48° C., about 4° C. to about 52° C., about 4° C. to about 56° C., about 4° C. to about 60° C., about 8° C. to about 12° C., about 8° C. to about 16° C., about 8° C. to about 20° C., about 8° C. to about 24° C., about 8° C. to about 28° C., about 8° C. to about 32° C., about 8° C. to about 36° C., about 8° C. to about 40° C., about 8° C. to about 44° C., about 8° C. to about 48° C., about 8° C. to about 52° C., about 8° C. to about 56° C., about 8° C. to about 60° C., about 12° C. to about 16° C., about 12° C. to about 20° C., about 12° C. to about 24° C., about 12° C. to about 28° C., about 12° C. to about 32° C., about 12° C. to about 36° C., about 12° C. to about 40° C., about 12° C. to about 44° C., about 12° C. to about 48° C., about 12° C. to about 52° C., about 12° C. to about 56° C., about 12° C. to about 60° C., about 16° C. to about 20° C., about 16° C. to about 24° C., about 16° C. to about 28° C., about 16° C. to about 32° C., about 16° C. to about 36° C., about 16° C. to about 40° C., about 16° C. to about 44° C., about 16° C. to about 48° C., about 16° C. to about 52° C., about 16° C. to about 56° C., about 16° C. to about 60° C., about 20° C. to about 24° C., about 20° C. to about 28° C., about 20° C. to about 32° C., about 20° C. to about 36° C., about 20° C. to about 40° C., about 20° C. to about 44° C., about 20° C. to about 48° C., about 20° C. to about 52° C., about 20° C. to about 56° C., about 20° C. to about 60° C., about 24° C. to about 28° C., about 24° C. to about 32° C., about 24° C. to about 36° C., about 24° C. to about 40° C., about 24° C. to about 44° C., about 24° C. to about 48° C., about 24° C. to about 52° C., about 24° C. to about 56° C., about 24° C. to about 60° C., about 28° C. to about 32° C., about 28° C. to about 36° C., about 28° C. to about 40° C., about 28° C. to about 44° C., about 28° C. to about 48° C., about 28° C. to about 52° C., about 28° C. to about 56° C., about 28° C. to about 60° C., about 32° C. to about 36° C., about 32° C. to about 40° C., about 32° C. to about 44° C., about 32° C. to about 48° C., about 32° C. to about 52° C., about 32° C. to about 56° C., about 32° C. to about 60° C., about 36° C. to about 40° C., about 36° C. to about 44° C., about 36° C. to about 48° C., about 36° C. to about 52° C., about 36° C. to about 56° C., about 36° C. to about 60° C., about 40° C. to about 44° C., about 40° C. to about 48° C., about 40° C. to about 52° C., about 40° C. to about 56° C., about 40° C. to about 60° C., about 44° C. to about 48° C., about 44° C. to about 52° C., about 44° C. to about 56° C., about 44° C. to about 60° C., about 48° C. to about 52° C., about 48° C. to about 56° C., about 48° C. to about 60° C., about 52° C. to about 56° C., about 52° C. to about 60° C. or about 52° C. to about 60° C.

Aspects of the present specification disclose, in part, purifying the first solvent mixture. In an aspect of this embodiment, the first solvent mixture is purified by filtration.

Aspects of the present specification disclose, in part, reducing the volume of the first solvent mixture in a manner that concentrates the one or more cannabinoids. In aspects of this embodiment, the volume of the first solvent mixture is reduced by evaporation. In aspects of this embodiment, the volume of the first solvent mixture is reduced by, e.g., 60% or less, 50% or less, 45% or less, 40% or less, 35% or less, 30% or less, 25% or less, 20% or less, 15% or less, 10% or less, 5% or less, 4% or less, 3% or less, 2% or less, or 1% or less of the original volume of the first solvent mixture used to extract the one or more cannabinoids from a plant material. In aspects of this embodiment, the volume of the first solvent mixture is reduced by, e.g., about 0.1% to about 5%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.1% to about 45%, about 0.1% to about 50%, about 0.5% to about 5%, about 0.5% to about 10%, about 0.5% to about 15%, about 0.5% to about 20%, about 0.5% to about 25%, about 0.5% to about 30%, about 0.5% to about 35%, about 0.5% to about 40%, about 0.5% to about 45%, about 0.5% to about 50%, about 1% to about 15%, about 1% to about 20%, about 1% to about 25%, about 1% to about 30%, about 1% to about 35%, about 1% to about 40%, about 1% to about 45%, about 1% to about 50%, about 1% to about 55%, about 1% to about 60%, 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 20% to about 25%, about 20% to about 30%, about 20% to about 35%, about 20% to about 40%, about 20% to about 45%, about 20% to about 50%, about 20% to about 55%, about 20% to about 60%, about 25% to about 30%, about 25% to about 35%, about 25% to about 40%, about 25% to about 45%, about 25% to about 50%, about 25% to about 55%, about 25% to about 60%, about 30% to about 35%, about 30% to about 40%, about 30% to about 45%, about 30% to about 50%, about 30% to about 55%, about 30% to about 60%, about 35% to about 40%, about 35% to about 45%, about 35% to about 50%, about 35% to about 55%, about 35% to about 60%, about 40% to about 45%, about 40% to about 50%, about 40% to about 55%, about 40% to about 60%, about 45% to about 50%, about 45% to about 55%, about 45% to about 60%, about 50% to about 55%, about 50% to about 60% or about 55% to about 60%.

Aspects of the present specification disclose, in part, incubating the reduced first solvent mixture in a manner that crystallizes one or more cannabinoids. Generally, crystallization of the one or more cannabinoids in the reduced first solvent mixture is a function of temperature and time. In aspects of this embodiment, the reduced first solvent mixture is incubated at a temperature of, e.g., −70° C. or higher, −60° C. or higher, −50° C. or higher, −40° C. or higher, −30° C. or higher, −20° C. or higher or 0° C. or higher, 4° C. or higher, 8° C. or higher, 12° C. or higher, 16° C. or higher, 20° C. or higher, 24° C. or higher or 28° C. or higher. In other aspects of this embodiment, the reduced first solvent mixture is incubated at a temperature of, e.g., −70° C. or lower, −60° C. or lower, −50° C. or lower, −40° C. or lower, −30° C. or lower, −20° C. or lower or 0° C. or higher, 4° C. or lower, 8° C. or lower, 12° C. or lower, 16° C. or lower, 20° C. or lower, 24° C. or lower or 28° C. or lower. In yet other aspects of this embodiment, the reduced first solvent mixture is incubated at a temperature of, e.g., about −70° C. to about 40° C., −70° C. to about 30° C., −70° C. to about 20° C., −70° C. to about 10° C., −70° C. to about 0° C., −20° C. to about 40° C., −20° C. to about 30° C., −20° C. to about 20° C., −20° C. to about 10° C., −20° C. to about 0° C., about 0° C. to about 5° C., about 0° C. to about 10° C., about 0° C. to about 15° C., about 0° C. to about 20° C., about 0° C. to about 25° C., about 0° C. to about 4° C., about 0° C. to about 8° C., about 0° C. to about 12° C., about 0° C. to about 16° C., about 0° C. to about 20° C., about 0° C. to about 24° C., about 0° C. to about 28° C., about 4° C. to about 8° C., about 4° C. to about 12° C. about 4° C. to about 16° C., about 4° C. to about 20° C., about 4° C. to about 24° C., about 4° C. to about 28° C., about 8° C. to about 12° C., about 8° C. to about 16° C., about 8° C. to about 20° C., about 8° C. to about 24° C., about 8° C. to about 28° C., about 12° C. to about 16° C., about 12° C. to about 20° C., about 12° C. to about 24° C., about 12° C. to about 28° C., about 16° C. to about 20° C., about 16° C. to about 24° C., about 16° C. to about 28° C., about 20° C. to about 24° C., about 20° C. to about 28° C. or about 24° C. to about 28° C.

In aspects of this embodiment, the reduced first solvent mixture is incubated for a time period of, e.g., 1 hour or more, 2 hours or more, 3 hours or more, 4 hours or more, 5 hours or more, 6 hours or more, 7 hours or more, 8 hours or more, 9 hours or more, 10 hours or more, 12 hours or more, 14 hours or more, 16 hours or more, 18 hours or more, 20 hours or more, 22 hours or more, 24 hours or more, 28 hours or more, 32 hours or more, 36 hours or more, 40 hours or more, 44 hours or more, 48 hours or more, 52 hours or more, 56 hours or more, 60 hours or more, 64 hours or more, 68 hours or more, 72 hours or more, 76 hours or more, 80 hours or more, 84 hours or more, 88 hours or more, 92 hours or more or 96 hours or more. In other aspects of this embodiment, the reduced first solvent mixture is incubated for a time period of, e.g., 1 hour or less, 2 hours or less, 3 hours or less, 4 hours or less, 5 hours or less, 6 hours or less, 7 hours or less, 8 hours or less, 9 hours or less, 10 hours or less, 12 hours or less, 14 hours or less, 16 hours or less, 18 hours or less, 20 hours or less, 22 hours or less, 24 hours or less, 28 hours or less, 32 hours or less, 36 hours or less, 40 hours or less, 44 hours or less, 48 hours or less, 52 hours or less, 56 hours or less, 60 hours or less, 64 hours or less, 68 hours or less, 72 hours or less, 76 hours or less, 80 hours or less, 84 hours or less, 88 hours or less, 92 hours or less or 96 hours or less. In yet other aspects of this embodiment, the reduced first solvent mixture is incubated for a time period of, e.g., about 1 hour to about 12 hours, about 1 hour to about 24 hours, about 1 hour to about 36 hours, about 1 hour to about 48 hours, about 1 hour to about 60 hours, about 1 hour to about 72 hours, about 1 hour to about 84 hours, about 1 hour to about 96 hours, about 2 hours to about 12 hours, about 2 hours to about 24 hours, about 2 hours to about 36 hours, about 2 hours to about 48 hours, about 2 hours to about 60 hours, about 2 hours to about 72 hours, about 2 hours to about 84 hours, about 2 hours to about 96 hours, about 4 hours to about 12 hours, about 4 hours to about 24 hours, about 4 hours to about 36 hours, about 4 hours to about 48 hours, about 4 hours to about 60 hours, about 4 hours to about 72 hours, about 4 hours to about 84 hours, about 4 hours to about 96 hours, about 6 hours to about 12 hours, about 6 hours to about 24 hours, about 6 hours to about 36 hours, about 6 hours to about 48 hours, about 6 hours to about 60 hours, about 6 hours to about 72 hours, about 6 hours to about 84 hours, about 6 hours to about 96 hours, about 8 hours to about 12 hours, about 8 hours to about 24 hours, about 8 hours to about 36 hours, about 8 hours to about 48 hours, about 8 hours to about 60 hours, about 8 hours to about 72 hours, about 8 hours to about 84 hours, about 8 hours to about 96 hours, about 12 hours to about 24 hours, about 12 hours to about 36 hours, about 12 hours to about 48 hours, about 12 hours to about 60 hours, about 12 hours to about 72 hours, about 12 hours to about 84 hours, about 12 hours to about 96 hours, about 16 hours to about 24 hours, about 16 hours to about 36 hours, about 16 hours to about 48 hours, about 16 hours to about 60 hours, about 16 hours to about 72 hours, about 16 hours to about 84 hours, about 16 hours to about 96 hours, about 24 hours to about 36 hours, about 24 hours to about 48 hours, about 24 hours to about 60 hours, about 24 hours to about 72 hours, about 24 hours to about 84 hours, about 24 hours to about 96 hours, about 36 hours to about 48 hours, about 36 hours to about 60 hours, about 36 hours to about 72 hours, about 36 hours to about 84 hours, about 36 hours to about 96 hours, about 48 hours to about 60 hours, about 48 hours to about 72 hours, about 48 hours to about 84 hours, about 48 hours to about 96 hours or about 72 hours to about 96 hours.

Aspects of the present specification disclose, in part, purifying the one or more cannabinoids crystallized after incubation in the reduced first solvent mixture. In an aspect of this embodiment, purification of the one or more crystallized cannabinoids is performed using filtration that results in a collection of a mother liquor.

Aspects of the present specification disclose, in part, incubating the one or more crystallized cannabinoids with a second non-polar solvent to form a second solvent mixture. Incubation of the one or more crystallized cannabinoids with a second non-polar solvent to form a second solvent mixture at least partially dissolves the one or more crystallized cannabinoids. In aspects of this embodiment, incubation of the one or more crystallized cannabinoids with a second non-polar solvent to form a second solvent mixture dissolves, e.g., at least 50%, at least 55%, at least 60%, at least 65%, at least 70%, at least 75%, at least 80%, at least 85%, at least 90% or at least 95% of the one or more crystallized cannabinoids. In other aspects of this embodiment, incubation of the one or more crystallized cannabinoids with a second non-polar solvent to form a second solvent mixture dissolves, e.g., at most 50%, at most 55%, at most 60%, at most 65%, at most 70%, at most 75%, at most 80%, at most 85%, at most 90% or at most 95% of the one or more crystallized cannabinoids. In yet other aspects of this embodiment, incubation of the one or more crystallized cannabinoids with a second non-polar solvent to form a second solvent mixture dissolves, e.g., about 50% to about 95%, about 55% to about 95%, about 60% to about 95%, about 65% to about 95%, about 70% to about 95%, about 75% to about 95%, about 80% to about 95%, about 85% to about 95%, about 90% to about 95%, about 50% to 100%, about 55% to 100%, about 60% to 100%, about 65% to 100%, about 70% to 100%, about 75% to 100%, about 80% to 100%, about 85% to 100%, about 90% to 100% or about 95% to 100%.

Generally, dissolving of the one or more cannabinoids in the second solvent mixture is a function of temperature and time. In aspects of this embodiment, the second solvent mixture is incubated at a temperature of, e.g., 20° C. or higher, 25° C. or higher, 30° C. or higher, 35° C. or higher, 40° C. or higher, 45° C. or higher, 50° C. or higher, 55° C. or higher or 60° C. or higher. In other aspects of this embodiment, the second solvent mixture is incubated at a temperature of, e.g., 20° C. or lower, 25° C. or lower, 30° C. or lower, 35° C. or lower, 40° C. or lower, 45° C. or lower, 50° C. or lower, 55° C. or lower or 60° C. or lower. In other aspects of this embodiment, the second solvent mixture is incubated at a temperature of, e.g., about 20° C. to about 25° C., about 20° C. to about 30° C., about 20° C. to about 35° C., about 20° C. to about 40° C., about 20° C. to about 45° C., about 20° C. to about 50° C., about 20° C. to about 55° C., about 20° C. to about 60° C., about 25° C. to about 30° C., about 25° C. to about 35° C., about 25° C. to about 40° C., about 25° C. to about 45° C., about 25° C. to about 50° C., about 25° C. to about 55° C., about 25° C. to about 60° C., about 30° C. to about 35° C., about 30° C. to about 40° C., about 30° C. to about 45° C., about 30° C. to about 50° C., about 30° C. to about 55° C., about 30° C. to about 60° C., about 35° C. to about 40° C., about 35° C. to about 45° C., about 35° C. to about 50° C., about 35° C. to about 55° C., about 35° C. to about 60° C., about 40° C. to about 45° C., about 40° C. to about 50° C., about 40° C. to about 55° C., about 40° C. to about 60° C., about 45° C. to about 50° C., about 45° C. to about 55° C., about 45° C. to about 60° C., about 50° C. to about 55° C., about 50° C. to about 60° C. or about 55° C. to about 60° C.

In aspects of this embodiment, the second solvent mixture is incubated for a time period of, e.g., at least 5 minutes, at least 10 minutes, at least 15 minutes, for at least 30 minutes, for at least 45 minutes, for at least 1 hour, for at least 1.25 hours, for at least 1.5 hours, for at least 1.75 hours, for at least 2 hours, for at least 2.25 hours, for at least 2.5 hours, for at least 2.75 hours, for at least 3.0 hours, for at least 3.25 hours, for at least 4.5 hours, for at least 4.75 hours, or for at least 5.0 hours. In other aspects of this embodiment, the second solvent mixture is incubated for a time period of, e.g., at most 5 hours, for at most 4.75 hours, for at most 4.5 hours, for at most 4.25 hours, for at most 4.0 hours, for at most 3.75 hours, for at most 3.5 hours, for at most 3.25 hours, for at most 3.0 hours, for at most 2.75 hours, for at most 2.5 hours, for at most 2.25 hours, for at most 2.0 hours, for at most 1.75 hours, for at most 1.5 hours, for at most 1.25 hours, for at most 1.25 hours, for at most 1.0 hours, for at most 45 minutes, for at most 30 minutes, or for at most 15 minutes. In yet other aspects of this embodiment, the second solvent mixture is incubated for a time period of, e.g., about 15 minutes to about 5 hours, about 30 minutes to about 5 hours, about 45 minutes to about 5 hours, about 1 hour to about 5 hours, about 1 hour to about 4 hours, about 1 hour to about 3.5 hours, about 1 hour to about 3.0 hours, about 1 hour to about 2.25 hours, about 1 hour to about 2 hours, about 1 hour to about 1.75 hours, about 1 hour to about 1.5 hours, about 30 minutes to about 1.5 hours, about 30 minutes to about 1.25 hours, about 30 minutes to about 1 hour, about 45 minutes to about 1.75 hours, about 45 minutes to about 1.5 hours, about 45 minutes to about 1.25 hours, or about 45 minutes to about 1 hour.

Aspects of the present specification disclose, in part, incubating the second solvent mixture in a manner that crystallizes the one or more cannabinoids. Generally, crystallization of the one or more cannabinoids in the second solvent mixture is a function of temperature and time. In aspects of this embodiment, the second solvent mixture is incubated at a temperature of, e.g., −70° C. or higher, −60° C. or higher, −50° C. or higher, −40° C. or higher, −30° C. or higher, −20° C. or higher or 0° C. or higher, 4° C. or higher, 8° C. or higher, 12° C. or higher, 16° C. or higher, 20° C. or higher, 24° C. or higher or 28° C. or higher. In other aspects of this embodiment, the second solvent mixture is incubated at a temperature of, e.g., −70° C. or lower, −60° C. or lower, −50° C. or lower, −40° C. or lower, −30° C. or lower, −20° C. or lower or 0° C. or higher, 4° C. or lower, 8° C. or lower, 12° C. or lower, 16° C. or lower, 20° C. or lower, 24° C. or lower or 28° C. or lower. In yet other aspects of this embodiment, the second solvent mixture is incubated at a temperature of, e.g., about −70° C. to about 40° C., −70° C. to about 30° C., −70° C. to about 20° C., −70° C. to about 10° C., −70° C. to about 0° C., −20° C. to about 40° C., −20° C. to about 30° C., −20° C. to about 20° C., −20° C. to about 10° C., −20° C. to about 0° C., about 0° C. to about 5° C., about 0° C. to about 10° C., about 0° C. to about 15° C., about 0° C. to about 20° C., about 0° C. to about 25° C., about 0° C. to about 4° C., about 0° C. to about 8° C., about 0° C. to about 12° C., about 0° C. to about 16° C., about 0° C. to about 20° C., about 0° C. to about 24° C., about 0° C. to about 28° C., about 4° C. to about 8° C., about 4° C. to about 12° C. about 4° C. to about 16° C., about 4° C. to about 20° C., about 4° C. to about 24° C., about 4° C. to about 28° C., about 8° C. to about 12° C., about 8° C. to about 16° C., about 8° C. to about 20° C., about 8° C. to about 24° C., about 8° C. to about 28° C., about 12° C. to about 16° C., about 12° C. to about 20° C., about 12° C. to about 24° C., about 12° C. to about 28° C., about 16° C. to about 20° C., about 16° C. to about 24° C., about 16° C. to about 28° C., about 20° C. to about 24° C., about 20° C. to about 28° C. or about 24° C. to about 28° C.

In aspects of this embodiment, the second solvent mixture is incubated for a time period of, e.g., 1 hour or more, 2 hours or more, 3 hours or more, 4 hours or more, 5 hours or more, 6 hours or more, 7 hours or more, 8 hours or more, 9 hours or more, 10 hours or more, 12 hours or more, 14 hours or more, 16 hours or more, 18 hours or more, 20 hours or more, 22 hours or more, 24 hours or more, 28 hours or more, 32 hours or more, 36 hours or more, 40 hours or more, 44 hours or more, 48 hours or more, 52 hours or more, 56 hours or more, 60 hours or more, 64 hours or more, 68 hours or more, 72 hours or more, 76 hours or more, 80 hours or more, 84 hours or more, 88 hours or more, 92 hours or more or 96 hours or more. In other aspects of this embodiment, the second solvent mixture is incubated for a time period of, e.g., 1 hour or less, 2 hours or less, 3 hours or less, 4 hours or less, 5 hours or less, 6 hours or less, 7 hours or less, 8 hours or less, 9 hours or less, 10 hours or less, 12 hours or less, 14 hours or less, 16 hours or less, 18 hours or less, 20 hours or less, 22 hours or less, 24 hours or less, 28 hours or less, 32 hours or less, 36 hours or less, 40 hours or less, 44 hours or less, 48 hours or less, 52 hours or less, 56 hours or less, 60 hours or less, 64 hours or less, 68 hours or less, 72 hours or less, 76 hours or less, 80 hours or less, 84 hours or less, 88 hours or less, 92 hours or less or 96 hours or less. In yet other aspects of this embodiment, the second solvent mixture is incubated for a time period of, e.g., about 1 hour to about 12 hours, about 1 hour to about 24 hours, about 1 hour to about 36 hours, about 1 hour to about 48 hours, about 1 hour to about 60 hours, about 1 hour to about 72 hours, about 1 hour to about 84 hours, about 1 hour to about 96 hours, about 2 hours to about 12 hours, about 2 hours to about 24 hours, about 2 hours to about 36 hours, about 2 hours to about 48 hours, about 2 hours to about 60 hours, about 2 hours to about 72 hours, about 2 hours to about 84 hours, about 2 hours to about 96 hours, about 4 hours to about 12 hours, about 4 hours to about 24 hours, about 4 hours to about 36 hours, about 4 hours to about 48 hours, about 4 hours to about 60 hours, about 4 hours to about 72 hours, about 4 hours to about 84 hours, about 4 hours to about 96 hours, about 6 hours to about 12 hours, about 6 hours to about 24 hours, about 6 hours to about 36 hours, about 6 hours to about 48 hours, about 6 hours to about 60 hours, about 6 hours to about 72 hours, about 6 hours to about 84 hours, about 6 hours to about 96 hours, about 8 hours to about 12 hours, about 8 hours to about 24 hours, about 8 hours to about 36 hours, about 8 hours to about 48 hours, about 8 hours to about 60 hours, about 8 hours to about 72 hours, about 8 hours to about 84 hours, about 8 hours to about 96 hours, about 12 hours to about 24 hours, about 12 hours to about 36 hours, about 12 hours to about 48 hours, about 12 hours to about 60 hours, about 12 hours to about 72 hours, about 12 hours to about 84 hours, about 12 hours to about 96 hours, about 16 hours to about 24 hours, about 16 hours to about 36 hours, about 16 hours to about 48 hours, about 16 hours to about 60 hours, about 16 hours to about 72 hours, about 16 hours to about 84 hours, about 16 hours to about 96 hours, about 24 hours to about 36 hours, about 24 hours to about 48 hours, about 24 hours to about 60 hours, about 24 hours to about 72 hours, about 24 hours to about 84 hours, about 24 hours to about 96 hours, about 36 hours to about 48 hours, about 36 hours to about 60 hours, about 36 hours to about 72 hours, about 36 hours to about 84 hours, about 36 hours to about 96 hours, about 48 hours to about 60 hours, about 48 hours to about 72 hours, about 48 hours to about 84 hours, about 48 hours to about 96 hours or about 72 hours to about 96 hours.

Aspects of the present specification disclose, in part, purifying the one or more crystallized cannabinoids obtained from the second solvent mixture. In an aspect of this embodiment, the one or more crystallized cannabinoids is purified using filtration that results in a collection of a mother liquor.

The disclosed methods may further comprising incubating the mother liquor in a manner that crystallizes the one or more cannabinoids. The one or more cannabinoids can be crystallized using the same temperature and time conditions used to crystallizes the one or more cannabinoids from the reduced first solvent mixture and/or the second solvent or solvent mixture.

The result of the disclosed methods is a substantially pure preparation of one or more cannabinoids. A "substantially pure" preparation of a cannabinoid or a cannabinoid acid is defined as a preparation having a chromatographic purity (of the desired cannabinoid or cannabinoid acid) of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

In an aspect of this embodiment, the disclosed methods result in the purification of CBGA having a purity that is 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard. In an aspect of this embodiment, the disclosed methods result in the purification of CBG having a purity that is 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard. In an aspect of this embodiment, the disclosed methods result in the purification of CBD having a purity that is 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

The disclosed methods can achieve substantially pure preparations of one or more cannabinoids without the use of chromatographic techniques. Said another way, the disclosed methods do not use chromatographic techniques to purify the one or more cannabinoids. Thus, in one embodiment, the disclosed methods result in a substantially pure preparation of one or more cannabinoids without the use chromatographic techniques. In an aspect of this embodiment, the disclosed methods result in a substantially pure preparation of CBGA without the use chromatographic techniques. In another aspect of this embodiment, the disclosed methods result in a substantially pure preparation of CBG without the use of chromatographic techniques. In yet another aspect of this embodiment, the disclosed methods result in a substantially pure preparation of CBD without the use chromatographic techniques.

The term "crude cannabinoid", "raw cannabinoid" or "product enriched in a given cannabinoid" encompasses preparations having at least 60%, at least 65%, at least 70%, at least 75%, at least 80%, at least 85%, or at least 90% chromatographic purity for the desired cannabinoid. Such a product will generally contain a greater proportion of impurities, non-target materials and other cannabinoids than a "substantially pure" preparation.

Cannabinoids

The cannabinoids purified by the disclosed methods are not particularly limited and include cannibigerol-type (CBG-type) cannabinoids; cannaibichromene-type cannabinoids (CBC-type); cannabidiol-type cannabinoids (CBD-type); tetrahydracannabinol-type cannabinoids (THC-type); cannabinol-type cannabinoids (CBN-type); and derivatives thereof. The cannabinoid derivatives may not themselves be cannabinoids. However, their chemistry is recognized as being derived from cannabigerol, cannabinol, or cannabidiol. For instance, cannabinoids of interest include the following and their corresponding acids: CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), THC (tetrahydrocannabinol), CBT (Cannabicitran-type), Iso-THC (Iso-Tetrahydrocannabinol-type) and CBE (Cannabielsoin-type). In fresh plant material of *cannabis*, most cannabinoids are present in the form carboxylic acid known as acidic cannabinoids or "cannabinoid acids". The free phenolic forms of the cannabinoids are also known as neutral cannabinoids.

The disclosed methods may be used to extract/purify cannabinoids or cannabinoid acids from any plant material known to contain such cannabinoids or cannabinoid acids. The source for the cannabinoids is not limited, but can include plant material. The term "plant material" encompasses a plant or plant part (e.g. bark, wood, leaves, stems, roots, flowers, fruits, seeds, berries or parts thereof) as well as exudates, resins, and plant extracts, and includes material falling within the definition of "botanical raw material" in the Guidance for Industry Botanical Drug Products Draft Guidance, August 2000, US Department of Health and Human Services, Food and Drug Administration Centre for Drug Evaluation and Research.

The disclosed methods may be used to extract/purify cannabinoids or cannabinoid acids from any plant material known to contain such cannabinoids or cannabinoid acids. Most typically, but not necessarily, the "plant material" will be derived from one or more *cannabis* plants. Plants from which cannabinoids may be isolated include: *Cannabis* sp. including *Cannabis sativa* L. and all subspecies, the putative species *Cannabis indica* Lam., *Cannabis ruderalis* Janisch, and hybrids and varieties thereof, as discussed further below. The *Cannabis sativa* L. plant can be of the variety Carma or any other variety of the chemotype IV, whose main cannabinoid is CBG or CBGA (Meijer E P, Hammond K M. The inheritance of chemical phenotype in *Cannabis sativa* L. (II): Cannabigerol predominant plants. Euphytica. 2005. 145: 189-198) or from any variety belonging to the chemotype II or III (de Meijer E P, Bagatta M, Carboni A, Crucitti P, Moliterni V M, Ranalli P, Mandolino G. The inheritance of chemical phenotype in *Cannabis sativa* L. Genetics. 2003. January; 163(1):335-46.)

In one embodiment, the disclosed methods uses material from the plant *Cannabis sativa* L. variety belonging to chemotype IV, having CBGA/CBG as main cannabinoids. In another embodiment, the disclosed methods uses material from the plant *Cannabis sativa* L. variety belonging to chemotype III, having CBDA/CBD as main cannabinoids. In yet another embodiment, the disclosed methods uses material from the plant *Cannabis sativa* L. variety belonging to chemotype II, having THCA-CBDA/THC-CBD as main cannabinoids.

The term "*cannabis* plant(s)" encompasses wild type *Cannabis sativa* and also variants thereof, including *cannabis* chemovars (varieties characterised by virtue of chemical composition) which naturally contain different amounts of the individual cannabinoids, also *Cannabis sativa* L. subspecies *indica* including the variants var. *indica* and var. *kafiristanica*, *Cannabis indica* and also plants which are the result of genetic crosses, self-crosses or hybrids thereof. The term "*cannabis* plant material" is to be interpreted accordingly as encompassing plant material derived from one or more *cannabis* plants. For the avoidance of doubt, it is hereby stated that "*cannabis* plant material" includes herbal *cannabis* and dried *cannabis* biomass.

"Decarboxylated *cannabis* plant material" refers to *cannabis* plant material which has been subject to a decarboxylation step in order to convert cannabinoid acids to the corresponding free cannabinoids.

Resins

"Resin" as used herein includes resins produced from any of the plant types discussed above, and in one embodiment, includes products of the stalked resin glands of *Cannabis* sp., including the putative species *Cannabis indica*, the species *Cannabis sativa* and *Cannabis ruderalis*, and hybrids or varietals thereof. These stalked resin glands may be from female, unfertilized or fertilized plants or from dioecious or monoecious varieties of *Cannabis*.

The method of the invention makes it possible to isolate the cannabinoids of interest (e.g., CBG, CBGA or CBD) directly by crystallization with a non-polar solvent (e.g., hexane or pentane), from the plant, resin or the extracts obtained from the plant, whether the extract is obtained with pentane, hexane, heptane, petroleum ethers, cyclohexane, dicloromethane, tricloromethane, tetrahydrofurane, diethyl ether, toluene, benzene, ethanol, methanol, isopropanol, acetone, acetonitrile, ethyl acetate, butane, propane, refrigerant gases (e.g.: 1,1,1,2-Tetrafluoroethane (R134a)) or, liquid, subcritical or supercritical $CO_2$ or mixes of these solvents. In this embodiment, the disclosed method obtains the cannabinoids of interest (e.g., CBG, CBGA or CBD) with a purity of 60% to 85%, which will be called "raw" with a high yield and further with a purity of at least 60%, at least 61%, at least 62%, at least 63%, at least 64% at least 65%, at least 66%, at least 67%, at least 68%, at least 69%, least 70%, at least 71%, at least 72%, at least 73%, at least 74% at least 75%, at least 76%, at least 77%, at least 78%, at least 79%, at least 80%, at least 81%, at least 82%, at least 83%, at least 84% or at least 85% (the yield ranges between 50%-90% depending on the type of plant raw material or the type of extract). Wth subsequent recrystallizations of this "raw" composition in a non-polar solvent (e.g., hexane), it is possible to obtain a purity greater than 90% achieving a purity of 95% of CBG, CBGA and CBD without using chromatographic techniques, and further, wherein the purity is greater than 90%, greater than 91%, greater than 92%, greater than 93%, greater than 94% or greater than 95%, greater than 96%, greater than 97%, greater than 98%, greater than 99%, of CBG, CBGA and CBD without using chromatographic techniques.

The non-polar solvent used to obtain an extract is not particularly limited, the method of the invention offers good results with extracts obtained with any of pentane, hexane, heptane, cyclohexane, petroleum ethers, dicloromethane, triclomethane, tethrahydrofurane, toluene, benzene, diethyl ether, ethanol, methanol, isopropanol, acetone, acetonitrile, ethyl acetate, butane, propane, refrigerant gases (e.g.: 1,1,1,2-Tetrafluoroethane (R134a)) and liquid, subcritical or supercritical $CO_2$ or mixes of these solvents.

Isolation of Cannabinoid Acids

In embodiments wherein the method is to be used for the isolation of cannabinoid acids an acidified extraction solvent to prepare the initial extract may optionally be used to ensure the extraction of high levels of cannabinoid acids. The primary purpose of this acidification is to prevent/minimise ionisation of the cannabinoid acid, which could otherwise adversely affect the purification process. In one embodiment, the method uses acidified non-polar solvents, of the types described above. Acidification may be achieved by the addition of a small volume of acid to the solvent. Generally, it is sufficient to add a relatively weak acid, such as acetic acid. For any given purification process the optimal amount and type of acid used may be determined empirically. An example of an acidified solvent is 0.1% acetic acid in hexane. Other solvents include pentane, hexane, heptane, cyclohexane, petroleum ethers, dicloromethane, tricloromethane, tetrahydrofurane, diethyl ether, ethanol, methanol, isopropanol, acetone, acetonitrile, ethyl acetate, butane, propane, refrigerant gas 1,1,1,2-Tetrafluoroethane (R134a), liquid $CO_2$, subcritical $CO_2$ or supercritical $CO_2$ or mixes of these solvents This is the extraction solvent of choice for preparing an initial extract from the starting plant material in the preparation of cannabinoid acids.

Isolation of Cannabigerol, Cannabidiol or Tetrahydrocannabinol-Prior Decarboxylation In embodiments of the method where it is desired to purify free cannabinoids, rather than the cannabinoid acids, the plant material may be subjected to a decarboxylation step. The purpose of the decarboxylation step is to convert cannabinoid acids present in the plant material to the corresponding free cannabinoids. Decarboxylation may be carried out by heating the plant material to a defined temperature for a suitable length of time. Decarboxylation of cannabinoid acids is a function of time and temperature, thus at higher temperatures a shorter period of time will be taken for complete decarboxylation of a given amount of cannabinoid acid. In selecting appropriate conditions for decarboxylation consideration must, however, be given to minimizing thermal degradation of the desirable, pharmacological cannabinoids into undesirable degradation products, particularly thermal degradation of $\Delta^9$ THC to cannabinol (CBN).

Thus, in another embodiment of the present methods, cannabigerol (CBG), cannabidiol (CBD) cannabidivarin (CBDV), tetrahydrocannabinol (THC) or tetrahydrocannabidivarin (THCV) are isolated and purified, and in which prior to performing step (a), the plant material, resin or extracts from the plant are decarboxylated for at least about 1 hour, 1.1 hours, 1.2 hour, 1.3 hours, 1.4 hours, 1.5 hours, 1.6 hours, 1.7 hours, 1.8 hours, 1.9 hours, 2 hours, 2.1 hours, 2.2 hours, 2.3 hours, 2.4 hours, 2.5 hours, 2.6 hours, 2.7 hours, 2.8 hours, 2.9 hours, 3 hours, 3.1 hours, 3.2 hours, 3.3 hours, 3.4 hours, 3.5 hours, 4 hours, 4.5 hours, 5 hours, 5.5 hours, 6 hours, 6.5 hours, 7 hours, 7.5 hours, 8 hours at around 60° C., 65° C., 70° C., 75° C., 80° C., 85° C., 90° C., 95° C., 100° C., 105° C., 110° C., 111° C. 112° C., 113° C., 114° C., 115° C., 116° C., 117° C., 118° C., 119° C., 120° C., 121° C. 122° C., 123° C., 124° C., 125° C., 126° C., 127° C., 128° C., 129° C. or 130° C., 135° C., 140° C., 145° C., 150° C., 155° C., 160° C., 165° C., 170° C., 175° C., or 180° C. In one embodiment, the decarboxylation is performed for at least 2 hours at a temperature of 120° C. In one embodiment, the decarboxylation is performed for at least 1 hours at a temperature of 150° C.

In one embodiment, the decarboxylation is performed at a temperature of at least 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., or 180° C. In one embodiment, the decarboxylation is performed at a temperature of at most 175° C., 170° C., 165° C., 160° C., 155° C., 150° C., 145° C., 140° C., 135° C., 130° C., 125° C., 120° C., 115° C., 110° C., 100° C., 95° C., 90° C., 85° C., 80° C., 75° C., 70° C., 65° C., or 60° C. In one embodiment, the decarboxylation is performed at a temperature ranging from 60° C. to 180° C., ranging from 70° C. to 175° C., 75° C. to 170° C., 80° C. to 165° C., 85° C. to 160° C., 90° C. to 155° C., 95° C. to 150° C., 100° C. to 145° C., 105° C. to 140° C., 110° C. to 135° C., 115° C. to 130° C., or 120° C. to 130° C.

In one embodiment, the decarboxylation is performed over a period ranging from at least about 1 hour to 10 hours. In one aspect, the decarboxylation is performed over a period from approximately at least 1 hour, at least 1.1 hours, at least 1.2 hours, at least 1.3 hours, at least 1.4 hours, at least 1.5 hours, at least 1.6 hours, at least 1.7 hours, at least 1.75 hours, at least 1.8 hours at least 1.9 hours, at least 2.0 hours, at least 2.1 hours, at least 2.2 hours, at least 2.25 hours, at least 2.3 hours, at least 2.4 hours, at least 2.5 hours, at least 2.75 hours, at least 3.0 hours, at least 3.25 hours, at least 3.5 hours, at least 3.75 hours, at least 4.0 hours, at least 4.25 hours, at least 4.5 hours, at least 4.5 hours, at least 4.75 hours, at least 5.0 hours, at least 5.5 hours, at least 6.0 hours, at least 6.5 hours, at least 7.0 hours, at least 8.0 hours, at least 8.5 hours, at least 9.0 hours, at least 9.5 hours, or at least 10 hours. In one aspect, the decarboxylation is performed for at most 10 hours, at most 9.5 hours, at most 9.0 hours, at most 8.5 hours, at most 8.0 hours, at most 7.5 hours, at most 7.0 hours, at most 6.5 hours, at most 6.0 hours, at most 5.5 hours, at most 5.0 hours, at most 4.75 hours, at most 4.5 hours at most 4.25 hours, at most 4.0 hours, at most 3.75 hours, at most 3.5 hours, at most 3.25 hours, at most 3.0 hours, at most 2.75 hours, at most 2.5 hours at most 2.25 hours, or at most 2.0 hours.

Following the disclosed methods, in order to increase the purity of the cannabinoid compound to values greater than 98% a chromatography can be carried out. Conventional chromatography techniques such as Flash, preparative HPLC and even liquid-liquid chromatographic techniques such as countercurrent chromatography (CCC) or centrifugal partition chromatography (CPC), can be used.

In another embodiment, the disclosed method provides for a chromatographic step is carried out prior to each crystallization step. In one embodiment, a chromatographic step may be added to the present methods. In one embodiment, the chromatographic technique may include column chromatography (such as FLASH chromatography or HPLC), and liquid:liquid chromatography (such as countercurrent chromatography and centrifugal partition chromatography). In one embodiment, the steps of countercurrent chromatography (CCC) or centrifugal partition chromatography (CPC) are optional, and may be included after one or more of the other steps. In an aspect of the chromatographic embodiment, the chromatographic step is applied after each crystallization step (e.g. after step (c), (e), (h) or (i)).

Both CCC and CPC are liquid-based chromatographic methods, where both the stationary phase and the mobile phase are liquids. By eliminating solid supports, permanent adsorption of the analyte onto the column is avoided, and a high recovery of the analyte can be achieved. The instrument is also easily switched between normal-phase and reversed-phase modes of operation simply by changing the mobile and stationary phases. Wth liquid chromatography, operation is limited by the composition of the columns and media commercially available for the instrument. Nearly any pair of immiscible solutions can be used in liquid-liquid chromatography provided that the stationary phase can be successfully retained. In one embodiment, the mobile phase is organic and/or non-polar, and the stationary phase is the aqueous and/or polar reagent.

Solvent costs for liquid:liquid chromatography are also generally lower than for high-performance liquid chromatography (HPLC), and the cost of purchasing and disposing of solid adsorbents is eliminated. Another advantage is that experiments conducted in the laboratory can be scaled to industrial volumes. When GC or HPLC is carried out with large volumes, resolution is lost due to issues with surface-to-volume ratios and flow dynamics; this is avoided when both phases are liquid.

In one embodiment the mobile organic phase may include hexane, cyclohexane, or heptane. In one embodiment, the stationary phase may include ethanol, methanol, isopropanol, acetone, acetonitrile and/or water. In one embodiment, the mobile phase is hexane, cyclohexane, or heptane and the stationary phase is water and ethanol, methanol, or isopropanol. In one embodiment, the mobile phase is heptane, and the stationary phase is acetone and acetonitrile.

In countercurrent chromatography (CCC) and centrifugal partition chromatography (CPC), a two-phase system is used. In one embodiment of the presently recited methods, the two-phase system includes Hexane:Ethanol:Water used at ratios of (20:19:1) to (20:8:12), in one embodiment, using ratios of (20:13:7) for isolation of CBG-type cannabinoids (CBG, CBGA and CBGV), using ratios of (20:14:6) for isolation of CBD-type cannabinoids (CBD, CBDA and CBDV), using ratios of (20:17:3) for isolation of THC-type cannabinoids (THC, THCA and THCV) or using a gradient reverse phase run with ethanol and water mix as mobile phase increasing the concentration of ethanol gradually from the ratio (20:12:8) to (20:18:2), with substitutions of heptane and/or cyclohexane with hexane and methanol or isopropanol instead of ethanol, with the organic phase of hexane as mobile phase or the two-phase system.

Another embodiment of the present methods includes a two-phase system having Hexane:Ethanol:Water at ratios ranging from 20:20:1 to 20:1:20 and from 20:1:5 to 20:1:10 and from 1:20:10 to 30:20:1. For example the ratio of hexane to ethanol may be range from about 1:20 to about 20:1, e.g., about 1:20, about 1:10, about 3:20, about 4:20, 5:20, about 6:20, about 7:20, about 8:20, about 9:20, about 10:20, about 11:20, about 12:20, about 13:20, about 14:20, about 15:20, about 16:20, about 17:20, about 18:20, about 19:20, about 20:20, about 20:19, about 20:18, about 20:17, about 20:16, about 20:15, about 20:14, about 20:13, about 20:12, about 20:11, about 20:10, about 20:9, about 20:8, about 20:7, about 20:6, about 20:5, about 20:4, about 20:3, about 20:2, or about 20:1. Similarly the ratio of ethanol to water, may range from about 20:1 to about 1:20, e.g., about 1:20, about 1:10, about 3:20, about 4:20, 5:20, about 6:20, about 7:20, about 8:20, about 9:20, about 10:20, about 11:20, about 12:20, about 13:20, about 14:20, about 15:20, about 16:20, about 17:20, about 18:20, about 19:20, about 20:20, about 20:19, about 20:18, about 20:17, about 20:16, about 20:15, about 20:14, about 20:13, about 20:12, about 20:11, about 20:10, about 20:9, about 20:8, about 20:7, about 20:6, about 20:5, about 20:4, about 20:3, about 20:2, or about 20:1.

In one aspect the ratio of Hexane:Ethanol:Water is (20:19:1) to (20:8:12), and with substitutions of heptane and/or cyclohexane with hexane and methanol and/or isopropanol instead of ethanol, with the organic phase of hexane as mobile phase or the two-phases system. In particular, the ratios of the two-phase system Hexane:Ethanol:Water are (20:13:7) for isolation of CBG-type cannabinoids, (20:14:6) for isolation of CBD-type cannabinoids and (20:17:3) to isolate THC-type cannabinoids or using a gradient reverse phase run with ethanol and water mix as mobile phase increasing the concentration of ethanol gradually from the ratio (20:12:8) to (20:18:2).

Another embodiment is the method of the invention, wherein the two-phase system, Hexane:Ethanol:Water is used, and substitutions of heptane and/or cyclohexane with hexane and methanol and/or isopropanol instead of ethanol, with the organic phase of hexane as mobile phase in the chromatographic techniques of CPC and CCC for isolating and/or purifying the cannabinoids that are present in extracts made with pentane, hexane, heptane, petroleum ethers, cyclohexane, diclorometane, triclorometane, tetrahydrofurane, diethyl ether, toluene, benzene, ethanol, methanol, isopropanol, acetone, acetonitrile, ethyl acetate, butane, propane, refrigerant gases (e.g.: 1,1,1,2-Tetrafluoroethane (R134a)) or, liquid, subcritical or supercritical CO2 or mixes of these solvents from any variety and chemotype of the *Cannabis sativa* L. plant.

Therefore, an embodiment of the method of the invention includes before each crystallization step (e.g., after step (c), (e), (h) or (i)) a countercurrent chromatography (CCC) or a centrifugal partition chromatography (CPC) are carried out to isolate and purify the cannabinoids: tetrahydrocannabinol (THC), tetrahydrocannabidivarin (THCV), tetrahydrocannabinolic acid (THCA), cannabidiol (CBD), cannabidivarin (CBDV) and cannabidiolic acid (CBDA).

Another embodiment is the method, wherein cannabigerol (CBG), cannabidiol (CBD), cannabidivarin (CBDV), tetrahydrocannabinol (THC) or tetrahydrocannabidivarin (THCV) are isolated and purified, and in which prior to performing step (a), the plant material or resin of said plant are decarboxylated at least at 120° C. for 2 hours.

Another embodiment is the method, wherein step (a) is repeated at least once. In one embodiment, step (a) is repeated 2 times or 3 times. Another embodiment is the method, wherein time in step (a) is at least about 60 minutes.

Another embodiment is the method, wherein step (i) is repeated at least once. In one embodiment, step (i) is repeated 2 times or 3 times.

Another embodiment is the method of the invention, wherein temperature in steps (d) and (g) is at least about −30° C. In one aspect, the temperature ranges from −30° C. to 30° C., −25° C. to 30° C., −20° C. to 30° C., −10° C. to 30° C., −5° C. to 30° C., 0° C. to 30° C., 5° C. to 30° C., 10° C. to 30° C., −30° C. to 25° C., −25° C. to 25° C., −20° C. to 25° C., −10° C. to 25° C., −5° C. to 25° C., 0° C. to 25° C., 5° C. to 25° C., 10° C. to 25° C., −30° C. to 20° C., −25° C. to 20° C., −20° C. to 20° C., −10° C. to 20° C., −5° C. to 20° C., 0° C. to 20° C., 5° C. to 20° C., 10° C. to 20° C. In one aspect the temperatures ranges from about −20° C. to about 6° C. In one aspect, the temperature is at least −30° C., −25° C., −20° C., −15° C., −10° C., −5° C., −4° C., 0° C., 4° C., 5° C., 6° C., 7° C., 8° C., 9° C., 10° C., 11° C., 12° C., 13° C., 14° C., 15° C., 16° C., 17° C., 18° C., 19° C., 20° C., 25° C., or 30° C. In one aspect, the temperature is at most about, −10° C., −5° C., −4° C., 0° C., 4° C., 5° C., 6° C., 7° C., 8° C., 9° C., 10° C., 11° C., 12° C., 13° C., 14° C., 15° C., 16° C., 17° C., 18° C., 19° C., 20° C., 25° C., or 30° C.

Another embodiment is the method, wherein time in step (d) is at least about 0.5 hours to at least about 108 hours. In one aspect, the time in step (d) can range from about 1 hour to about 108 hours, from about 2 hours to about 108 hours, from about 3 hours to about 108 hours, from about 5 hours to about 108 hours, from about 6 hours to about 108 hours, from about 8 hours to about 108 hours, from about 10 hours to about 108 hours, from about 12 hours to about 108 hours, from about 18 hours to about 108 hours, from about 24 hours to about 108 hours, from about 36 hours to about 108 hours, from about 48 hours to about 108 hours, from about 72 hours to about 108 hours, from about 84 to about 108 hours, from about 96 hours to about 108 hours, from about 1 hour to about 96 hours, from about 2 hours to about 96 hours, from about 3 hours to about 96 hours, from about 5 hours to about 96 hours, from about 6 hours to about 96 hours, from about 8 hours to about 96 hours, from about 10 hours to about 96 hours, from about 12 hours to about 96 hours, from about 18 hours to about 96 hours, from about 24 hours to about 96 hours, from about 36 hours to about 96 hours, from about 48 hours to about 96 hours, from about 72 hours to about 96 hours, from about 84 to about 96 hours, 1 hour to about 72 hours, from about 2 hours to about 72 hours, from about 3 hours to about 72 hours, from about 5 hours to about 72 hours, from about 6 hours to about 72 hours, from about 8 hours to about 72 hours, from about 10 hours to about 72 hours, from about 12 hours to about 72 hours, from about 18 hours to about 72 hours, from about 24 hours to about 72 hours, from about 36 hours to about 72 hours, from about 48 hours to about 72 hours, 1 hour to about 48 hours, from about 2 hours to about 48 hours, from about 3 hours to about 48 hours, from about 5 hours to about 48 hours, from about 6 hours to about 48 hours, from about 8 hours to about 48 hours, from about 10 hours to about 48 hours, from about 12 hours to about 48 hours, from about 18 hours to about 48 hours, from about 24 hours to about 48 hours, from about 36 hours to about 48 hours, 1 hour to about 36 hours, from about 2 hours to about 36 hours, from about 3 hours to about 36 hours, from about 5 hours to about 36 hours, from about 6 hours to about 36 hours, from about 8 hours to about 36 hours, from about 10 hours to about 36 hours, from about 12 hours to about 36 hours, from about 18 hours to about 36 hours, from about 24 hours to about 36 hours, 1 hour to about 24 hours, from about 2 hours to about 24 hours, from about 3 hours to about 24 hours, from about 5 hours to about 24 hours, from about 6 hours to about 24 hours, from about 8 hours to about 24 hours, from about 10 hours to about 24 hours, from about 12 hours to about 24 hours, from about 18 hours to about 24 hours, from about 1 hour to about 12 hours, from about 2 hours to about 12 hours, from about 3 hours to about 12 hours, from about 4 hours to about 12 hours, from about 5 hours to about 12 hours, from about 6 hours to about 12 hours, from about 8 hours to about 12 hours, or from about 9 hours to about 12 hours. In one aspect, the time in step (d) ranges from 1 hour to 96 hours, 1 hour to 72 hours, 1 hour to 48 hours, 1 hour to 24 hours, or 1 hour to 12 hours.

Another embodiment is the method of the invention, wherein time in step (g) is at least about 0.1 hours to 108 hours. In one aspect the time in step (g) can range from about 0.1 hour to about 108 hours, from about 1 hour to about 108 hours, from about 2 hours to about 108 hours, from about 3 hours to about 108 hours, from about 5 hours to about 108 hours, from about 6 hours to about 108 hours, from about 8 hours to about 108 hours, from about 10 hours to about 108 hours, from about 12 hours to about 108 hours, from about 18 hours to about 108 hours, from about 24 hours to about 108 hours, from about 36 hours to about 108 hours, from about 48 hours to about 108 hours, from about 72 hours to about 108 hours, from about 84 to about 108 hours, from about 96 hours to about 108 hours, from about 0.1 hour to about 96 hours, from about 1 hour to about 96 hours, from about 2 hours to about 96 hours, from about 3 hours to about 96 hours, from about 5 hours to about 96 hours, from about 6 hours to about 96 hours, from about 8 hours to about 96 hours, from about 10 hours to about 96 hours, from about 12 hours to about 96 hours, from about 18 hours to about 96 hours, from about 24 hours to about 96 hours, from about 36 hours to about 96 hours, from about 48 hours to about 96 hours, from about 72 hours to about 96 hours, from about 84 to about 96 hours, from about 0.1 hour to about 72 hours, from about 1 hour to about 72 hours, from about 2 hours to about 72 hours, from about 3 hours to about 72 hours, from about 5 hours to about 72 hours, from about 6 hours to about 72 hours, from about 8 hours to about 72 hours, from about 10 hours to about 72 hours, from about 12 hours to about 72 hours, from about 18 hours to about 72 hours, from about 24 hours to about 72 hours, from about 36 hours to about 72 hours, from about 48 hours to about 72 hours, from about 0.1 hour to about 48 hours, 1 hour to about 48 hours, from about 2 hours to about 48 hours, from about 3 hours to about 48 hours, from about 5 hours to about 48 hours, from about 6 hours to about 48 hours, from about 8 hours to about 48 hours, from about 10 hours to about 48 hours, from about 12 hours to about 48 hours, from about 18 hours to about 48 hours, from about 24 hours to about 48 hours, from about 36 hours to about 48 hours, from about 0.1 hour to about 36 hours, 1 hour to about 36 hours, from about 2 hours to about 36 hours, from about 3 hours to about 36 hours, from about 5 hours to about 36 hours, from about 6 hours to about 36 hours, from about 8 hours to about 36 hours, from about 10 hours to about 36 hours, from about 12 hours to about 36 hours, from about 18 hours to about 36 hours, from about 24 hours to about 36 hours, from about 0.1 hour to about 24 hours, 1 hour to about 24 hours, from about 2 hours to about 24 hours, from about 3 hours to about 24 hours, from about 5 hours to about 24 hours, from about 6 hours to about 24 hours, from about 8 hours to about 24 hours, from about 10 hours to about 24 hours, from about 12 hours to about 24 hours, from about 18 hours to about 24 hours, from about 0.1 hour to about 12 hours, from about 1 hour to about 12 hours, from about 2 hours to about 12 hours, from about 3 hours to about 12 hours, from about 4 hours to about 12 hours, from about 5 hours to about 12 hours, from about 6 hours to about 12 hours, from about 8 hours to about 12 hours, or from about 9 hours to about 12 hours. In one aspect, the time in step (g) ranges from 0.1 hour to 96 hours, 0.1 hour to 72 hours, 0.1 hour to 48 hours, 0.1 hour to 24 hours, or 0.1 hour to 12 hours.

Characterization of Resultant Product

In one embodiment, the present methods obtain a substantially pure cannabinoid product. A "substantially pure" preparation of a cannabinoid or a cannabinoid acid is defined as a preparation having a chromatographic purity (of the desired cannabinoid or cannabinoid acid) of greater than 90%, greater than 91%, greater than 92%, greater than 93%, greater than 94%, greater than 95%, greater than 96%, greater than 97%, greater than 98%, greater than 99% and greater than 99.5%, as determined by area normalisation of an HPLC profile or by quantification by HPLC with a certified commercial standard.

Figure 3:
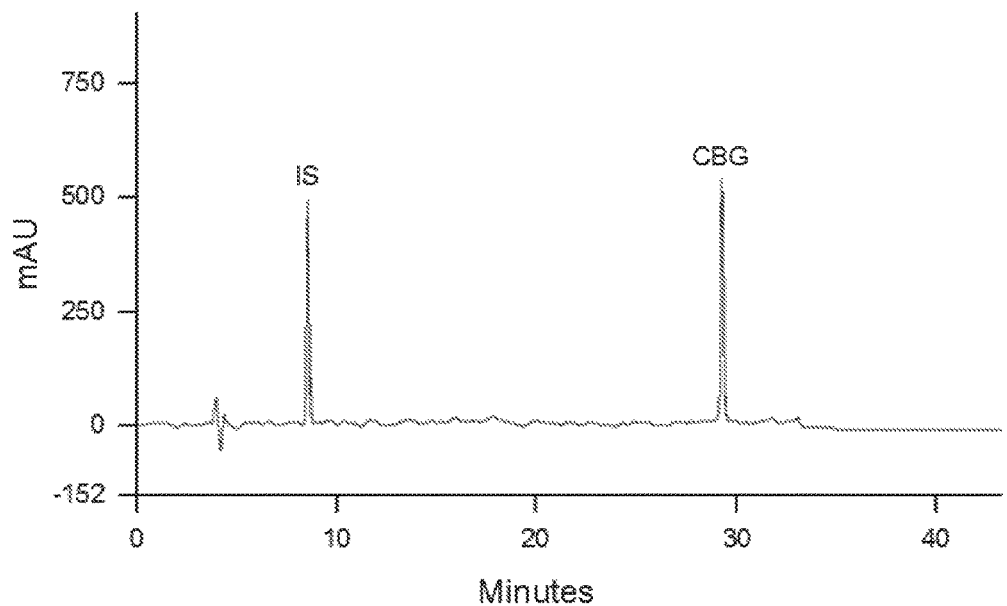
FIG. 3 shows a HPLC chromatogram at 210 nm of CBG obtained in Example 13 with purity of 99.06±0.38 quantified with certified commercial standard.
Figure 5:
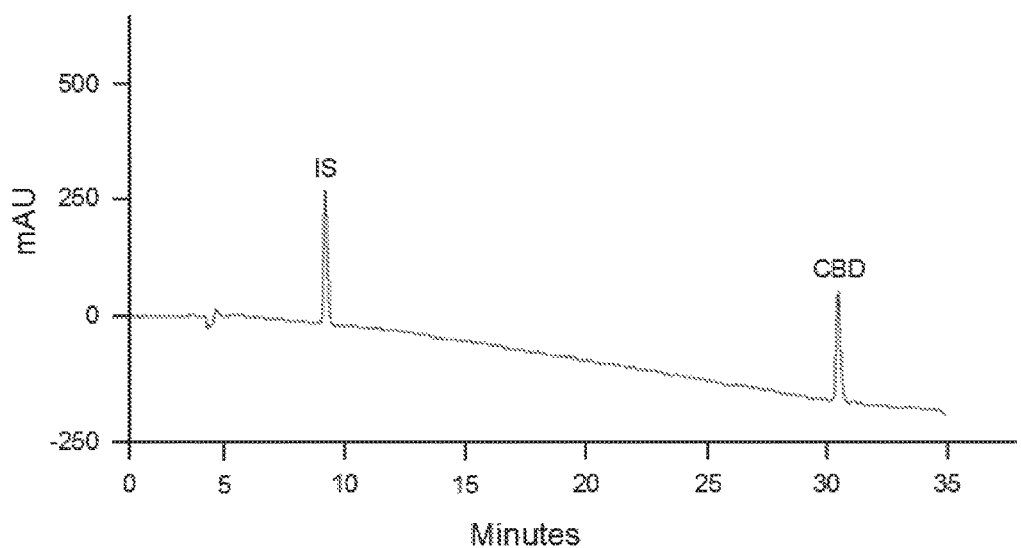
FIG. 5 shows a HPLC chromatogram at 210 nm of CBD obtained in Example 17 with purity of 97.16±0.15 quantified with certified commercial standard.

Purity of CBG and CBD are expressed as HPLC quantification with certified commercial standard from THCPharm GmB shown in FIGS. 3 and 5. Purity of CBGA is expressed as % of normalized HPLC peak area shown in FIG. 1.

The HPLC conditions used to test the cannabinoid purity where the following: Column: Mediterranean Sea, C18, 3 µm size particle, 250 mm×4.6 mm; Mobil phase: Water and Methanol with formiate ammonium; Det.: DAD, 210 nm (CBG and CBD) and 270 nm (CBGA); lnj.: 10 µL; Oven: 34° C.

Figure 2:
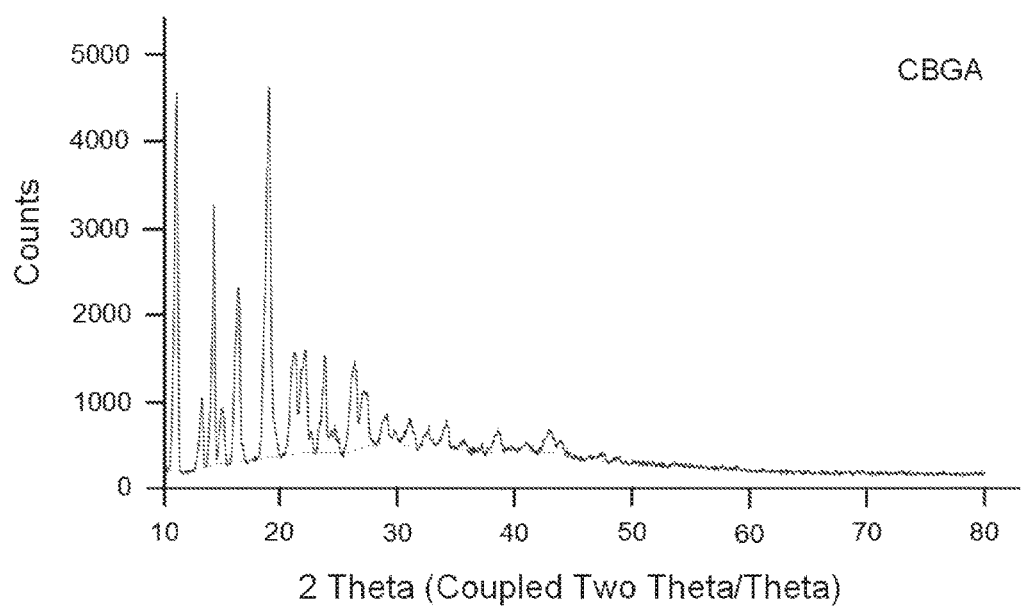
FIG. 2 shows the X-ray crystallography diffraction pattern of CBGA obtained in Example 4.
Figure 4:
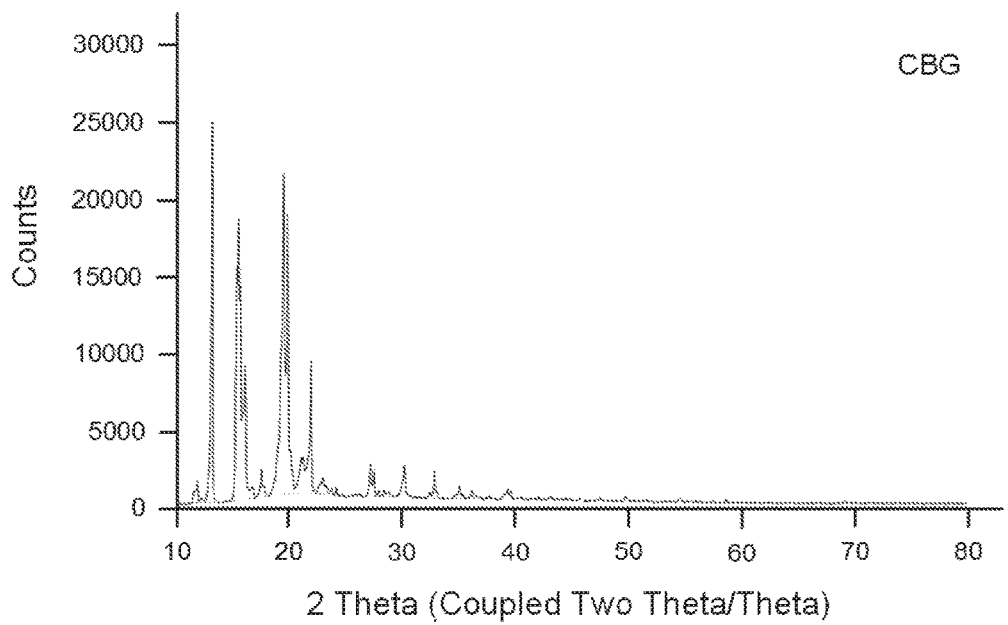
FIG. 4 shows the X-ray crystallography diffraction pattern of CBG obtained in Example 13.
Figure 6:
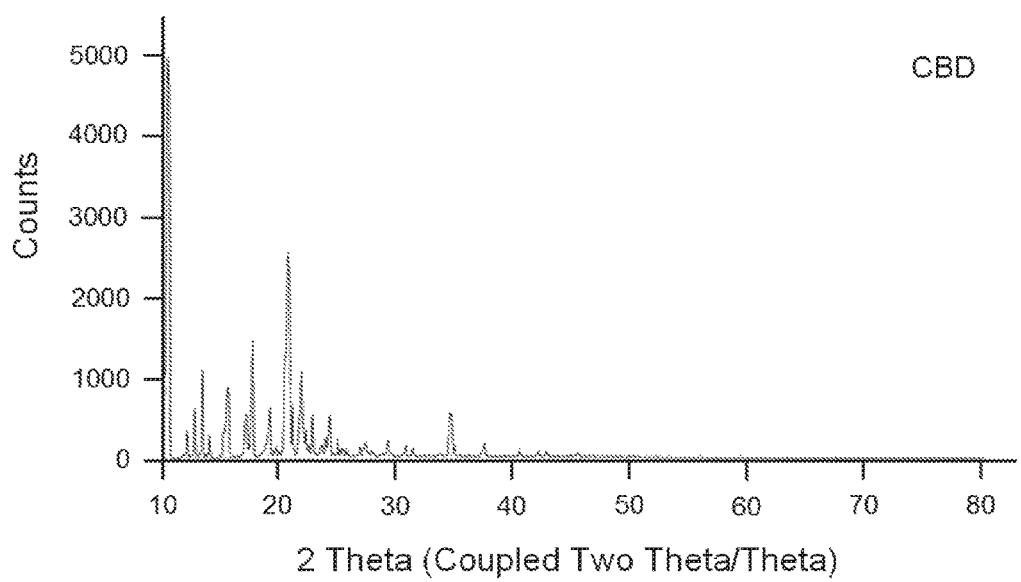
FIG. 6 shows the X-ray crystallography diffraction pattern of CBD obtained in Example 17.

X-ray crystallography diffraction patterns also studied and shown in FIGS. 2, 4 and 6.

Products Obtained by Methods

The present methods obtain a composition which includes a substantially pure cannabinoid or cannabinoid acid in liquid or solid form. For instance, the final product may be applied while in its crystalline form or may be further dissolved or formulated into a liquid, powder or compressed tablet. In one embodiment, the present methods obtain a crystalline cannabinoid in powder form. In another embodiment, the present methods obtain a cannabinoid solution.

The product obtained herein may be incorporated or formulated into products suitable for pharmaceutical purposes, recreational ingestion (e.g., food supplements, nutriceuticals), or as recreational inhalants (e.g., cigarettes and/or oils or liquids for electronic cigarettes/vape/hookah products, or incense).

Of course working with *cannabis* plants and cannabinoids may require a government license or approval in some territories, but may often be obtained for medicinal purposes. That said, the present methods do not exclude the use of the product as a non-medicinal product, with the appropriate government approvals.

Pharmaceutical Product

The present methods in one embodiment produce a product which may be included in a pharmaceutical product, medicinal preparation, or medicament (hereinafter "pharmaceuticals"). Such pharmaceutical products may be formulated as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc.

Products obtained by the present methods may be included in a pharmaceutical composition including a compound of the present product or a pharmaceutically acceptable salt or solvate thereof, together with a pharmaceutically acceptable excipient. In an aspect of this embodiment, a pharmaceutical composition comprises CBGA, CBG, CBD or any combination thereof. In a preferred aspect of this embodiment, a pharmaceutical composition comprises CBD.

The term "excipient" is used herein to describe any ingredient other than the compound of the invention. The choice of excipient will to a large extent depend on factors such as the particular mode of administration, the effect of the excipient on solubility and Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories and sprays.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form.

In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight % or from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets", Vol. 1, by H. Lieberman and L. Lachman (Marcel Dekker, New York, 1980).

Consumable oral films are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. The products obtained by the present methods can also be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates and buffering agents (in one embodiment, to a pH of from 3 to 9), but, for some applications, they may be more suitably formulated as a sterile non-aqueous solution or as a dried form to be used in conjunction with a suitable vehicle such as sterile, pyrogen-free water.

Formulations for parenteral administration may be formulated to be immediate and/or modified release. Modified release formulations include delayed-, sustained-, pulsed-, controlled-, targeted and programmed release. Thus the compound of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds obtained by the present methods may also be administered topically to the skin or mucosa, that is, dermally or transdermally. Typical formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Pharmaceutical compositions for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

The pharmaceutical composition described herein may be combined with the administration of another drug or active ingredient. Thus, the present products may be used to alleviate, minimize or prevent not only a disease or condition, but a side effect of another treatment regime.

Recreational Products

In one embodiment, the purified cannabinoids obtained by the present methods may be included in compositions such as oils (both for topical administration as massage oil, or to be burned or aeresolized), incense, cosmetics, bath oils, perfumes, makeup, food seasonings, toothpastes, ingestible solids (e.g., as a powder included in or on foods) or liquids (e.g., teas), etc.

For instance, a product produced by the present methods may be included in a "vape" product containing propylene glycol, glycerine, vegetable glycerine, aqueous glycerine, and optionally flavorings. In one aspect, the "vape" product may also include other drugs, such as nicotine.

Methods of Treatinci a Condition

The pharmaceutical products described herein may be administered to treat or reduce the symptoms of a disease or condition. In one embodiment, the present products may be administered to treat pain, Schizophrenia, convulsion, inflammation, anxiety or panic, depression (including unipolar or bipolar mood disorder and syndromal depression etc.), as a neuroprotective (i.e., for treatment of neurodegenerative disease, stroke, traumatic brain injury), cancer, graft-versus-host disease, migraines, arthritis, chronic pain (including neuropathic pain), nausea and vomiting, anorexia, glaucoma, glioma, epilepsy (that affects children and adults), asthma, perinatal asphyxia, addiction (and symptoms of dependency and withdrawal), movement disorders evidencing spasticity (in multiple sclerosis and spinal cord injury), Tourette's syndrome, dystonia, and tardive dyskinesia.

In particular methods embodiments, treatment methods reduce, decrease, suppress, limit, control or inhibit the presence of one or more symptoms associated with a condition; reduce, decrease, suppress, limit, control or inhibit side-effects of another pharmaceutical treatment; reduce, decrease, suppress, limit, control or inhibit the symptoms of addiction. In additional particular methods embodiments, treatment methods include administration of an amount of the present product sufficient to increase, induce, enhance, augment, promote or stimulate an immune response against the condition; or decrease, reduce, inhibit, suppress, prevent, control, or limit the spread of the condition within a subject or patient, or between subjects or patients. In further particular methods embodiments, treatment methods include administration of an amount of the present products sufficient to protect an individual from a pathology related to the condition, or reduce, decrease, limit, control or inhibit susceptibility to a pathology related to the condition.

Reagents for the Performance of the Present Method

In yet another embodiment the present invention includes reagents for the purification of cannabinoids. Such reagents include hexane (for CBG and CBGA), pentane and petroleum ether 40-60° C. bp (for CBD), heptane and petroleum ether 60-80° C. bp for the crystallization of the cannabinoid, and optionally reagents for the liquid chromatography such as ethanol, methanol, or isopropyl, or heptane, acetone, and acetonitrile.

Kits

Yet another embodiment of the present invention includes a kit for the purification of cannabinoids including the non-polar organic solvent, any filtration devices needed (such as a vacuum filtration mechanism including bottle top filters, and syringe filters), and any reagents, columns, or cartridges needed for the optional chromatography.

Aspects of the present specification can also be described as follows:

1. A method of purifying one or more cannabinoids from a plant material, the method comprising a) incubating the plant material with a first non-polar solvent to form a first solvent mixture which extracts the one or more cannabinoids from a plant material; b) reducing the volume of the first solvent mixture to about 50% or less of the original volume of the first solvent mixture in step (a) in a manner that concentrates the one or more cannabinoids; c) incubating the reduced first solvent mixture at a temperature range of between about −70° C. to about 40° C. in a manner that crystallizes the one or more cannabinoids; d) incubating the one or more crystallized cannabinoids with a second non-polar solvent to form a second solvent mixture, wherein the second solvent mixture dissolves at least 50% of the one or more crystallized cannabinoids; and e) incubating the second solvent mixture at a temperature range of between about −70° C. to about 40° C. in a manner that crystallizes the one or more cannabinoids, thereby resulting in the purification of one or more cannabinoids.

2. The method according to embodiment 1, wherein the plant material is a plant extract or a plant resin.

3. The method according to embodiment 1 or embodiment 2, wherein the plaint material is derived from the genera *Cannabis*.

4. The method according to any one of embodiments 1-3, wherein the plaint material is derived from a *Cannabis sativa, Cannabis indica Cannabis ruderalis*, hybrids thereof or varietals thereof.

5. The method according to embodiment 4, wherein the *Cannabis sativa* varietal comprises a Chemotype II varietal, a Chemotype III varietal or a Chemotype IV varietal.

6. The method according to embodiment 4, wherein the *Cannabis sativa* varietal comprises a Carma varietal, a AIDA varietal, a SARA varietal, a PILAR varietal, a Futura 75 varietal or a 60.2/1/9 experimental varietal.

7. The method according to any one of embodiments 1-6, wherein prior to step (a), the plant material is treated to decarboxylate one or more cannabinoids present in the plant material.

8. The method according to any one of embodiments 1-7, wherein the first non-polar solvent of step (a) comprises pentane, hexane, heptane, cyclohexane, petroleum ether, dicloromethane, tricloromethane, tethrahydrofurane, diethyl ether, ethanol, methanol, isopropanol, acetone, acetonitrile, ethyl acetate, butane, propane, refrigeration gas 1,1,1,2-Tetrafluoroethane (R134a), liquid $CO_2$, subcritical $CO_2$ and supercritical $CO_2$.

9. The method according to any one of embodiments 1-8, wherein the one or more cannabinoids comprise tetrahydrocannabinol (THC), tetrahydrocannabidivarin (THCV), tetrahidrocannabinolic acid (THCA), cannabidiol (CBD), cannabidivarin (CBDV), cannabidiolic acid (CBDA), cannabigerol (CBG), canabigerovarin (CBGV) or cannabigerolic acid (CBGA).

10. The method according to any one of embodiments 1-9, wherein in step (a) the first solvent mixture is incubated at least 5 minutes.

11. The method according to embodiment 10, wherein in step (a) the first solvent mixture is incubated at about 10 minutes to about 1500 minutes.

12. The method according to embodiment 11, wherein in step (a) the first solvent mixture is incubated at about 30 minutes to about 120 minutes.

13. The method according to any one of embodiments 1-12, wherein step (a) is repeated at least once.

14. The method according to embodiment 13, wherein step (a) is repeated three times.

15. The method according to any one of embodiments 1-14, wherein in step (b), the volume of the first solvent mixture is reduced to about 1% to about 50% of the original volume of the first solvent mixture in step (a).

16. The method according to embodiment 15, wherein in step (b), the volume of the first solvent mixture is reduced to about 0.1% to about 15% of the original volume of the first solvent mixture in step (a).

17. The method according to embodiment 15, wherein in step (b), the volume of the first solvent mixture is reduced to about 16% to about 50% of the original volume of the first solvent mixture in step (a).

18. The method according to any one of embodiments 1-17, wherein in step (b), the volume of the first solvent mixture is reduced by evaporation.

19. The method according to any one of embodiments 1-18, wherein in step (c), the reduced first solvent mixture is incubated at a temperature range of between about −20° C. to about 30° C.

20. The method according to embodiment 19, wherein in step (c), the reduced first solvent mixture is incubated at a temperature range of between about 0° C. to about 25° C.

21. The method according to embodiment 20, wherein in step (c), the reduced first solvent mixture is incubated at a temperature range of between about 4° C. to about 8° C.

22. The method according to any one of embodiments 1-21, wherein in step (c), the reduced first solvent mixture is incubated for a time period of at least 30 minutes, at least 1 hour or at least 2 hours.

23. The method according to embodiment 22, wherein in step (c), the reduced first solvent mixture is incubated for a time period of between 1 hour and 96 hours.

24. The method according to embodiment 23, wherein in step (c), the reduced first solvent mixture is incubated for a time period of between 2 hour and 72 hours.

25. The method according to embodiment 24, wherein in step (c), the reduced first solvent mixture is incubated for a time period of between 4 hour and 48 hours.

26. The method according to embodiment 25, wherein in step (c), the reduced first solvent mixture is incubated for a time period of between 6 hour and 24 hours.

27. The method according to embodiment 26, wherein in step (c), the reduced first solvent mixture is incubated for a time period of between 12 hour and 24 hours.

28. The method according to any one of embodiments 1-27, wherein step (c) further comprises seeding the reduced solvent mixture with a cannabinoid.

29. The method according to embodiment 28, wherein the cannabinoid used to seed the reduced solvent mixture comprises a purified cannabinoid, a partially purified cannabinoid or crude extract comprising a cannabinoid.

30. The method according to any one of embodiments 1-29, wherein the second non-polar solvent of step (d) comprises pentane, hexane, heptane, petroleum ethers, cyclohexane, dicloromethane, tricloromethane, tetrahydrofurane, diethyl ether, toluene, benzene, ethanol, methanol, isopropanol, acetone, acetonitrile, ethyl acetate, butane, propane, refrigerant gases (e.g.: 1,1,1,2-Tetrafluoroethane (R134a)) or, liquid, subcritical or supercritical CO2 or mixes of these solvents.

31. The method according to any one of embodiments 1-30, wherein in step (d), the second solvent mixture dissolves at least 75% of the one or more crystallized cannabinoids.

32. The method according to embodiment 31, wherein in step (d), the second solvent mixture dissolves at least 85% of the one or more crystallized cannabinoids.

33. The method according to embodiment 32, wherein in step (d), the second solvent mixture dissolves at least 95% of the one or more crystallized cannabinoids.

34. The method according to any one of embodiments 1-33, wherein in step (d), the second solvent mixture is incubated at a temperature range of between about 30° C. to about 60° C.

35. The method according to embodiment 34, wherein in step (d), the second solvent mixture is incubated at a temperature range of between about 40° C. to about 50° C.

37. The method according to any one of embodiments 1-35, wherein in step (d), the second solvent mixture is incubated for a time period of at least 6 minutes.

38. The method according to embodiment 37, wherein in step (d), the second solvent mixture is incubated for a time period of between 0.25 hour and 4 hours.

39. The method according to any one of embodiments 1-38, wherein in step (e), the second solvent mixture is incubated at a temperature range of between about −20° C. to about 30° C.

40. The method according to embodiment 39, wherein in step (e), the second solvent mixture is incubated at a temperature range of between about 0° C. to about 25° C.

41. The method according to embodiment 40, wherein in step (e), the second solvent mixture is incubated at a temperature range of between about 4° C. to about 8° C.
42. The method according to any one of embodiments 1-41, wherein in step (e), the second solvent mixture is incubated for a time period of at least 6 minutes, at least 1 hour, at least 2 hours, at least 3 hours or at least 4 hours.
43. The method according to embodiment 42, wherein in step (e), the second solvent mixture is incubated for a time period of between 0.1 hour and 96 hours.
44. The method according to embodiment 43, wherein in step (e), the second solvent mixture is incubated for a time period of between 2 hour and 72 hours.
45. The method according to embodiment 44, wherein in step (e), the second solvent mixture is incubated for a time period of between 4 hour and 48 hours.
46. The method according to embodiment 45, wherein in step (e), the second solvent mixture is incubated for a time period of between 6 hour and 24 hours.
47. The method according to embodiment 46, wherein in step (e), the second solvent mixture is incubated for a time period of between 12 hour and 24 hours.
48. The method according to any one of embodiments 1-47, wherein the one or more crystallized cannabinoids of step (c) is purified prior to step (d).
49. The method according to embodiment 48, wherein the purification is performed using filtration that results in a collection of a mother liquor.
50. The method according to embodiment 49, further comprising incubating the mother liquor at a temperature range of between about −70° C. to about 40° C. in a manner that crystallizes the one or more cannabinoids.
51. The method according to embodiment 50, further comprising f) purifying the one or more crystallized cannabinoids using filtration that results in a collection of a mother liquor; and g) incubating the mother liquor at a temperature range of between about −70° C. to about 40° C. in a manner that crystallizes the one or more cannabinoids.
52. The method according to any one of embodiments 1-52, wherein steps (f) and (g) are repeated at least once.
53. The method according to embodiment 52, wherein steps (f) and (g) are repeated 2 times.
54. The method according to embodiment 53, wherein steps (f) and (g) are repeated 3 times.
55. The method according to any one of embodiments 1-54, wherein steps (d) and (e) are repeated at least once.
56. The method according to embodiment 50, wherein steps (d) and (e) are repeated 2 times.
57. The method according to embodiment 51, wherein steps (d) and (e) are repeated 3 times.
58. The method according to any one of embodiments 1-57, wherein the first solvent mixture of step (a) is purified prior to step (b).
59. The method according to embodiment 58, wherein the purification is performed using filtration.
60. The method according to any one of embodiments 1-59, wherein the one or more crystallized cannabinoids of step (e) is filtered.
61. The method according to any one of embodiments 1-60, further comprising performing liquid:liquid chromatography after one or more of steps (b) or (d).
62. The method according to embodiment 61, wherein the liquid:liquid chromatography is counter current chromatography (CCC) or centrifugal partition chromatography (CPC).
63. The method according to embodiment 62, wherein the mobile organic phase includes hexane, cyclohexane, or heptane.
64. The method according to embodiment 62, wherein the stationary phase includes ethanol, methanol, isopropanol, acetone, acetonitrile and/or water.
65. The method according to embodiment 62, wherein the mobile phase is hexane, cyclohexane, or heptane and the stationary phase is water and ethanol, methanol, or isopropanol.
66. The method according to embodiment 62, wherein the mobile phase is heptane, and the stationary phase is acetone and acetonitrile.
67. A purified cannabinoid produced by the method according to any one of embodiments 1-66.
68. A pharmaceutical composition comprising a purified cannabinoid produced by the method according to any one of embodiments 1-66.
69. The pharmaceutical composition of embodiment 68, further comprising a pharmaceutically acceptable excipient or carrier.
70. A method of treating a disease or condition comprising administering the cannabinoid produced by the method according to any one of embodiments 1-66 to a subject in need thereof.
71. The method of treating a disease or condition of embodiment 70, wherein the disease or condition is pain, schizophrenia, convulsion, inflammation, anxiety, depression, neurodegenerative disease, stroke, traumatic brain injury, cancer, migraines, arthritis, chronic pain, nausea and vomiting, anorexia, glaucoma, epilepsy, asthma, addiction, symptoms of dependency and withdrawal, multiple sclerosis, spinal cord injury, Tourette's syndrome, dystonia, or tardive dyskinesia.
72. A method of purifying a cannabinoid from a plant material, the method comprising: a) incubating the plant material with a first non-polar solvent to form a first solvent mixture which extracts the one or more cannabinoids from a plant material; b) filtering the first solvent mixture; c) reducing the volume of the first solvent mixture to about 50% or less of the original volume of the first solvent mixture in step (a) in a manner that concentrates the one or more cannabinoids; d) incubating the reduced first solvent mixture at a temperature range of between about −70° C. to about 40° C. in a manner that crystallizes the one or more cannabinoids; e) purifying the one or more crystallized cannabinoids in step (d) using filtration that results in a collection of a mother liquor; f) incubating the one or more crystallized cannabinoids with a second non-polar solvent to form a second solvent mixture, wherein the second solvent mixture dissolves at least 50% of the one or more crystallized cannabinoids; g) incubating the second solvent mixture at a temperature range of between about −70° C. to about 40° C. in a manner that crystallizes the one or more cannabinoids; and h) purifying the one or more crystallized cannabinoids of step (g) using filtration that results in a collection of a mother liquor, thereby resulting in the purification of one or more cannabinoids
73. The method according to embodiment 72, wherein the mother liquor of step (e) and/or step (h) is incubated at a temperature range of between about −70° C. to about 40° C. in a manner that crystallizes the one or more cannabinoids.
74. The method according to embodiment 73, further comprising i) purifying the one or more crystallized cannabinoids using filtration that results in a collection of a mother liquor; and j) incubating the mother liquor at a temperature range of between about −70° C. to about 40° C. in a manner that crystallizes the one or more cannabinoids.

75. The method according to embodiment 74, wherein steps (i) and (j) are repeated at least once.
76. The method according to embodiment 75, wherein steps (i) and (j) are repeated 2 times.
77. The method according to embodiment 76, wherein steps (i) and (j) are repeated 3 times.
78. The method according to any one of embodiments 72-77, wherein steps (f) and (g) are repeated at least once.
79. The method according to embodiment 78, wherein steps (f) and (g) are repeated 2 times.
80. The method according to embodiment 79, wherein steps (f) and (g) are repeated 3 times.
81. The method according to any one of embodiments 72-80, wherein steps (f), (g) and (h) are repeated at least once.
82. The method according to embodiment 81, wherein steps (f), (g) and (h) are repeated 2 times.
83. The method according to embodiment 82, wherein steps (f), (g) and (h) are repeated 3 times.
84. The method according to any one of embodiments 72-83, wherein the plant material is a plant extract or a plant resin.
85. The method according to any one of embodiments 72-84, wherein the plaint material is derived from the genera *Cannabis*.
86. The method according to any one of embodiments 72-85, wherein the plaint material is derived from a *Cannabis sativa, Cannabis indica Cannabis ruderalis*, hybrids thereof or varietals thereof.
87. The method according to embodiment 86, wherein the *Cannabis sativa* varietal comprises a Chemotype II varietal, a Chemotype III varietal or a Chemotype IV varietal.
88. The method according to embodiment 86, wherein the *Cannabis sativa* varietal comprises a Carma varietal, a AIDA varietal, a SARA varietal, a PILAR varietal, a Futura 75 varietal or a 60.2/1/9 experimental varietal.
89. The method according to any one of embodiments 72-88, wherein prior to step (a), the plant material is treated to decarboxylate one or more cannabinoids present in the plant material.
90. The method according to any one of embodiments 72-89, wherein the first non-polar solvent of step (a) comprises pentane, hexane, heptane, cyclohexane, petroleum ether, dicloromethane, tricloromethane, tethrahydrofurane, diethyl ether, benzene, toluene, ethanol, methanol, isopropanol, acetone, acetonitrile, ethyl acetate, butane, propane, refrigeration gas 1,1,1,2-Tetrafluoroethane (R134a), liquid $CO_2$, subcritical $CO_2$ and supercritical $CO_2$.
91. The method according to any one of embodiments 72-90, wherein the one or more cannabinoids comprise tetrahydrocannabinol (THC), tetrahydrocannabidivarin (THCV), tetrahidrocannabinolic acid (THCA), cannabidiol (CBD), cannabidivarin (CBDV), cannabidiolic acid (CBDA), cannabigerol (CBG), cannabigerovarin (CBGV) or cannabigerolic acid (CBGA).
92. The method according to any one of embodiments 72-91, wherein in step (a) the first solvent mixture is incubated at least 5 minutes.
93. The method according to embodiment 92, wherein in step (a) the first solvent mixture is incubated at about 10 minutes to about 1500 minutes.
94. The method according to embodiment 93, wherein in step (a) the first solvent mixture is incubated at about 30 minutes to about 120 minutes.
95. The method according to any one of embodiments 72-94, wherein step (a) is repeated at least once.
96. The method according to embodiment 95, wherein step (a) is repeated twice.
97. The method according to embodiment 96, wherein step (a) is repeated 3 times.
98. The method according to any one of embodiments 72-97, wherein in step (c), the volume of the first solvent mixture is reduced to about 5% to about 50% of the original volume of the first solvent mixture in step (a).
99. The method according to embodiment 98, wherein in step (c), the volume of the first solvent mixture is reduced to about 1% to about 15% of the original volume of the first solvent mixture in step (a).
100. The method according to embodiment 98, wherein in step (c), the volume of the first solvent mixture is reduced to about 15% to about 50% of the original volume of the first solvent mixture in step (a).
101. The method according to any one of embodiments 72-100, wherein in step (c), the volume of the first solvent mixture is reduced by evaporation.
102. The method according to any one of embodiments 72-101, wherein in step (d), the reduced first solvent mixture is incubated at a temperature range of between about −20° C. to about 30° C.
103. The method according to embodiment 102, wherein in step (d), the reduced first solvent mixture is incubated at a temperature range of between about 0° C. to about 25° C.
104. The method according to embodiment 103, wherein in step (d), the reduced first solvent mixture is incubated at a temperature range of between about 4° C. to about 8° C.
105. The method according to any one of embodiments 72-104, wherein in step (d), the reduced first solvent mixture is incubated for a time period of at least 30 minutes, at least 1 hour or at least 2 hours.
106. The method according to embodiment 105, wherein in step (d), the reduced first solvent mixture is incubated for a time period of between 1 hour and 96 hours.
107. The method according to embodiment 106, wherein in step (d), the reduced first solvent mixture is incubated for a time period of between 2 hour and 72 hours.
108. The method according to embodiment 107, wherein in step (d), the reduced first solvent mixture is incubated for a time period of between 4 hour and 48 hours.
109. The method according to embodiment 108, wherein in step (d), the reduced first solvent mixture is incubated for a time period of between 6 hour and 24 hours.
110. The method according to embodiment 109, wherein in step (d), the reduced first solvent mixture is incubated for a time period of between 12 hour and 24 hours.
111. The method according to any one of embodiments 72-110, wherein step (d) further comprises seeding the reduced solvent mixture with a cannabinoid.
112. The method according to embodiment 111, wherein the cannabinoid used to seed the reduced solvent mixture comprises a purified cannabinoid, a partially purified cannabinoid or crude extract comprising a cannabinoid.
113. The method according to any one of embodiments 72-112, wherein the second non-polar solvent of step (f) comprises pentane, hexane, heptane, cyclohexane, petroleum ether, dicloromethane, tricloromethane, tethrahydrofurane, diethyl ether, benzene, toluene, ethanol, methanol, isopropanol, acetone, acetonitrile, ethyl acetate, butane, propane, refrigeration gas 1,1,1,2-Tetrafluoroethane (R134a), liquid $CO_2$, subcritical $CO_2$ and supercritical $CO_2$.

114. The method according to any one of embodiments 72-113, wherein in step (f), the second solvent mixture dissolves at least 75% of the one or more crystallized cannabinoids.
115. The method according to embodiment 114, wherein in step (f), the second solvent mixture dissolves at least 85% of the one or more crystallized cannabinoids.
116. The method according to embodiment 115, wherein in step (f), the second solvent mixture dissolves at least 95% of the one or more crystallized cannabinoids.
117. The method according to any one of embodiments 72-116, wherein in step (f), the second solvent mixture is incubated at a temperature range of between about 30° C. to about 60° C.
118. The method according to embodiment 117, wherein in step (f), the second solvent mixture is incubated at a temperature range of between about 40° C. to about 50° C.
119. The method according to any one of embodiments 72-118, wherein in step (f), the second solvent mixture is incubated for a time period of at least 6 minutes.
120. The method according to embodiment 119, wherein in step (f), the second solvent mixture is incubated for a time period of between 0.1 hour and 4 hours.
121. The method according to any one of embodiments 72-120, wherein in step (g), the second solvent mixture is incubated at a temperature range of between about −20° C. to about 30° C.
122. The method according to embodiment 121, wherein in step (g), the second solvent mixture is incubated at a temperature range of between about 0° C. to about 25° C.
123. The method according to embodiment 122, wherein in step (g), the second solvent mixture is incubated at a temperature range of between about 4° C. to about 8° C.
124. The method according to any one of embodiments 72-123, wherein in step (g), the second solvent mixture is incubated for a time period of at least 6 minutes, at least 1 hour, at least 2 hours, at least 3 hours or at least 4 hours.
125. The method according to embodiment 124, wherein in step (g), the second solvent mixture is incubated for a time period of between 0.1 hour and 96 hours.
126. The method according to embodiment 125, wherein in step (g), the second solvent mixture is incubated for a time period of between 2 hour and 72 hours.
127. The method according to embodiment 126, wherein in step (g), the second solvent mixture is incubated for a time period of between 4 hour and 48 hours.
128. The method according to embodiment 127, wherein in step (g), the second solvent mixture is incubated for a time period of between 6 hour and 24 hours.
129. The method according to embodiment 128, wherein in step (g), the second solvent mixture is incubated for a time period of between 12 hour and 24 hours.
130. The method according to any one of embodiments 72-129, wherein the temperature in steps (d) and (g) is at most about 4° C. for CBGA/CBG purification and step (d) is at most −20° C. for CBD purification.
131. The method according to any one of embodiments 72-130, further comprising performing liquid:liquid chromatography after one or more of steps (c), (e) or (h).
132. The method according to embodiment 131, wherein the liquid:liquid chromatography is counter current chromatography (CCC) or centrifugal partition chromatography (CPC).
133. The method according to embodiment 131 or embodiment 132, wherein the mobile organic phase includes hexane, cyclohexane, or heptane.
134. The method according to any one of embodiments 131-132, wherein the stationary phase includes ethanol, methanol, isopropanol, acetone, acetonitrile and/or water.
135. The method according to embodiment 131 or embodiment 132, wherein the mobile phase is hexane, cyclohexane, or heptane and the stationary phase is water and ethanol, methanol, or isopropanol.
136. The method according to embodiment 131 or embodiment 132, wherein the mobile phase is heptane, and the stationary phase is acetone and acetonitrile.
137. The method according to any one of embodiments 72-136, further comprising performing counter current chromatography (CCC) or centrifugal partition chromatography (CPC) after the steps (e) or (h) to isolate, purify or repurify the cannabinoids tetrahydrocannabinol (THC), tetrahydrocannabidivarin (THCV), tetrahidrocannabinolic acid (THCA), cannabidiol (CBD), cannabidivarin (CBDV), cannabidiolic acid (CBDA), cannabigerol (CBG), cannabigerovarin (CBGV) and cannabigerolic acid (CBGA).
138. The method according to any one of embodiments 131-137, wherein the chromatography uses a two-phase system, Hexane:Ethanol:Water at ratios of (20:19:1) to (20:8:12) and wherein hexane may be substituted by heptane and/or cyclohexane and wherein ethanol may be substituted by methanol and/or isopropanol instead of ethanol, with the organic phase of hexane as mobile phase or the two-phase system.
139. The method according to any one of embodiments 131-138, wherein the ratios of the two-phase system, Hexane:Ethanol:Water are (20:13:7) for CBG-type cannabinoids (20:14:6) for CBD-type cannabinoids and (20:17:3) for THC-type cannabinoids or using a gradient reverse phase run with ethanol and water mix as mobile phase increasing the concentration of ethanol gradually from the ratio (20:12:8) to (20:18:2).
140. The method according to any one of embodiments 72-139, wherein cannabigerol (CBG), cannabigerovarin (CBGV), cannabidiol (CBD), cannabidivarin (CBD), tetrahydrocannabidivarin (THCV) or tetrahidrocannabinol (THC) are isolated and purified and prior to step (a), the plant material, resin or extracts of said plant are decarboxylated at about at least 120° C. for at least 1 hour.
141. The method according to any one of embodiments 72-139, wherein cannabigerol (CBG), cannabigerovarin (CBGV), cannabidiol (CBD), cannabidivarin (CBDV), tetrahydrocannabidivarin (THCV) or tetrahidrocannabinol (THC) is isolated and purified, and prior to step (a), the plant, plant material, plant extract, or resin are decarboxylated by hydrodistillation (steam distillation) at least at 90° C. for 2 hours.
142. A purified cannabinoid produced by the method according to any one of embodiments 72-141.
143. A pharmaceutical composition comprising a purified cannabinoid produced by the method according to any one of embodiments 72-141.
144. The pharmaceutical composition of embodiment 143, further comprising a pharmaceutically acceptable excipient or carrier.
145. A method of treating a disease or condition comprising administering the cannabinoid produced by the method according to any one of embodiments 72-141 to a subject in need thereof.
146. The method of treating a disease or condition of embodiment 145, wherein the disease or condition is pain, schizophrenia, convulsion, inflammation, anxiety, depression, neurodegenerative disease, stroke, traumatic brain injury, cancer, migraines, arthritis, chronic pain, nausea and vomiting, anorexia, glaucoma, epilepsy, asthma, addiction, symptoms of dependency and withdrawal, multiple sclerosis, spinal cord injury, Tourette's syndrome, dystonia, or tardive dyskinesia.

147. The method according to any one of embodiments 7 or 89, wherein the plant material is heated between 100° C. to 160° C. in order to decarboxylate one or more cannabinoids present in the plant material.

148. The method according to embodiment 147, wherein the plant material is heated between 120° C. to 150° C. in order to decarboxylate one or more cannabinoids present in the plant material.

149. The method according to embodiments 147 or 148, wherein the plant material is heated for a time period of at least 30 minutes.

150. The method according to embodiment 149, wherein the plant material is heated for a time period of about 1 hour to about 3 hours.

151. The method according to any one of embodiments 1-150, wherein the one or more cannabinoids purified is CBGA, CBG, CBD, or any combination thereof.

152. The method according to embodiments 151, wherein the CBGA has a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

153. The method according to embodiments 151, wherein the CBG has a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

154. The method according to embodiments 151, wherein the CBD has a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

155. The pharmaceutical composition of any one of embodiments 68, 69, 143 or 144, wherein the purified cannabinoid is CBGA, CBG, CBD, or any combination thereof.

156. The pharmaceutical composition of embodiment 155, wherein the purified cannabinoid is CBGA having a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

157. The pharmaceutical composition of embodiment 155, wherein the purified cannabinoid is CBG having a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

158. The pharmaceutical composition of embodiment 155, wherein the purified cannabinoid is CBD having a purity of 90% or greater, 91% or greater, 92% or greater, 93% or greater, 94% or greater, 95% or greater, 96% or greater, 97% or greater, 98% or greater or 99% or greater as determined by area normalisation of an HPLC profile or by a quantification percent of purity respect a certified commercial standard.

159. The method according to any one of embodiments 1-154, wherein a substantially pure preparation of one or more cannabinoids is acheived without the use a chromatographic technique.

160. The method according to embodiment 159, wherein a substantially pure preparation of CBGA is acheived without the use a chromatographic technique.

161. The method according to embodiment 159, wherein a substantially pure preparation of CBG is acheived without the use a chromatographic technique.

162. The method according to embodiment 159, wherein a substantially pure preparation of CBD is acheived without the use a chromatographic technique.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

Example 1

Isolation of CBGA from Plant Material

Maceration of 150 g of plant material of *Cannabis sativa* L. of the Carma variety, with CBGA as predominant, is carried out in 750 mL of hexane for one hour. This procedure is repeated three times. The plant material is filtered and the hexane is evaporated down to a volume of about 100 mL. The extract is then incubated at about 4° C. for about 24 hours in order to crystallize CBGA "raw" material. The CBGA "raw" material is vacuum filtered and the collected mother liquors is evaporated to a volume of about 30 mL to about 50 mL, is incubated at about 4° C. for about 48 hours in order to crystallize the CBGA "raw" material, and is then vacuum filtered. The amount of CBGA "raw" material obtained in this two step process depends on CBGA concentration in the starting plant material.

The CBGA "raw" obtained is recrystallized with 5 mL of hexane per gram of CBGA two or three more times to obtain CBGA with a purity greater than 90% and about 95%.

Subsequently, the raw or recrystallized CBGA is purified by means of countercurrent chromatography, using the two-phase system, Hexane:Ethanol:Water (20:14:6) or (20:12:8) with the organic phase of the hexane as mobile phase. The CBGA is eluted to a K of 3.2-3.5 (20:14:6) or K of 1-1.5 (20:12:8), admitting a load of 0.5 g to 1 g of recrystallized CBGA per 100 mL of CCC coil. A CBGA having a purity greater than 98% is generally obtained.

Example 2

Isolation of CBGA from Plant Material

This experiment was repeated 3 times, the data shown is the mean of the three experiments. Maceration of 100.5 g of plant material of *Cannabis sativa* L. of the Carma variety, with CBGA as predominant, was carried out in 1 L of hexane for one hour. This procedure is repeated two times more with 0.75 L of hexane. The plant material was filtered and the hexane was evaporated down to a volume of 65 mL and then incubated at 4° C. for 18 hours in order to crystallize CBGA "raw" material. About 1.54 g of CBGA "raw" material was obtained. The CBGA "raw" material was vacuum filtered and the collected mother liquors evaporated to a volume of 35 mL and incubated at 4° C. for 24 hours in order to crystallize the CBGA "raw" material. About 0.22 g of CBGA "raw" material was obtained. The total amount of CBGA "raw" material obtained in this three step process was 1.76 g, representing a yield of 1.75% by weight of the initial plant material used.

1.7 g of CBGA "raw" material was then recrystallized with 9 mL of hexane (ratio of about 5 mL of hexane per gram of CBGA). The CBGA mixture was heated at 50° C. and then incubated at 4° C. for 2 hours in order to crystallize CBGA. About 1.42 g of CBGA was obtained from first recrystallization; an 83.5% yield from the initial CBGA "raw" material. A second recrystallization was performed in two of the three experiments with 1.49 g of CBGA and 15 mL of hexane (ratio of about 10 mL of hexane per gram of CBGA). The CBGA mixture was heated at 50° C. and then incubated at 4° C. for 2 hours in order to crystallize CBGA. About 1.43 g of CBGA with a purity of 95% or more was obtained, with a yield of 95.9% from the first recrystallization CBGA amount. A third recrystallization was performed in one of the three experiments with 1.45 g of CBGA and 15 mL of hexane (ratio of about 10 mL of hexane per gram of CBGA). The CBGA mixture was heated at 50° C. and then incubated at 4° C. for 2 hours in order to crystallize CBGA. About 1.36 g of CBGA with a purity of 95% or more was obtained. The yield of the third recrystallization was 93.7% and represents an 80% yield from initial CBGA "raw" material. The total amount of CBGA with a purity of 95% or more obtained was 1.43 g, representing a yield of 84.1% from the CBGA "raw" material used and 1.43% by weight of the initial plant material used. Wth one recrystallization CBGA with a purity over 95% was obtained.

Example 3

Isolation of CBGA from Plant Material

This experiment was repeated 3 times, the data shown is the mean of the three experiments. Maceration of 95.2 g of plant material of *Cannabis sativa* L. of the AIDA variety (CVPO File number: 20160167 from 14-1-16), with CBGA as predominant, was carried out in 1 L of hexane for one hour. This procedure is repeated two times more with 0.75 L of hexane. The plant material was filtered and the hexane was evaporated down to a volume of 80 mL and then incubated at 4° C. for 18 hours in order to crystallize CBGA "raw" material. About 1.8 g of CBGA "raw" material was obtained. The CBGA "raw" material was vacuum filtered and the collected mother liquors evaporated to a volume of 40 mL and incubated at 4° C. for 24 hours in order to crystallize the CBGA "raw" material. About 0.4 g of CBGA "raw" material was obtained. The total amount of CBGA "raw" material obtained in this two step process was 2.2 g, representing a yield of 2.3% by weight of the initial plant material used.

1.75 g of the CBGA "raw" material was then recrystallized with 9 mL of hexane (ratio of about 10 mL of hexane per gram of CBGA). The CBGA mixture was heated at 50° C. and then incubated at 4° C. for 2 hours in order to crystallize CBGA. About 1.51 g of CBGA with purity of 97% was obtained. The same recrystallization process was performed with the 0.4 g CBGA "raw" obtained from the mother liquors using 4 mL of hexane. About 0.35 g of CBGA with purity of 99% was obtained. The total amount of CBGA with a purity of 95% or more obtained was 1.86 g, representing a yield of 86.5% from the CBGA "raw" material used and 1.95% by weight of the initial plant material used. With only one recrystallization, CBGA with a purity over 95% was obtained.

Example 4

Isolation of CBGA from Plant Material

Maceration of 2.8 Kg of plant material of *Cannabis sativa* L. of the AIDA variety (CVPO File number: 20160167 from 14-1-16), with CBGA as predominant, was carried out in 25 L of hexane for one hour. This procedure was repeated two times more. The plant material was filtered and the hexane was evaporated down to a volume of 3 L and then incubated at 23° C. in order to crystallize CBGA "raw" material. About 26.5 g of CBGA "raw" material was obtained. The CBGA "raw" material was vacuum filtered and the mother liquors collected, evaporated to a volume of 2 L and then incubated at 7° C. for 24 hours in order to crystallize the CBGA "raw" material. About 8.8 g of CBGA "raw" material was obtained. The total amount of CBGA "raw" material obtained in this three step process was 37.4 g, representing a yield of 1.3% by weight of the initial plant material used.

35.3 g of the CBGA "raw" material was then recrystallized with 1 L of hexane (ratio of about 28 mL of hexane per gram of CBGA). The CBGA mixture was heated at 50° C. for 1 hour and then vacuum filtered to obtain 18.7 g of CBGA "washed" material. The collected mother liquors were evaporated down and then incubated at ambient temperature (23° C.) for 2 hours in order to crystallize CBGA. About 6.5 g of CBGA was obtained. The CBGA was vacuum filtered, and the collected mother liquors evaporated down and incubated at 5° C. for 2 hours in order to crystallize CBGA. About 3.7 g of CBGA was obtained. The total amount of CBGA with a purity of 95% or more obtained was 28.9 g, representing a yield of 81.9% from the CBGA "raw" material used and 1% by weight of the initial plant material used. Wth one recrystallization at ambient temperature, CBGA with a purity of over 95% was obtained (see FIG. 1 and FIG. 2).

Example 5

Isolation of CBGA from Extracts

Maceration of 10 g of extract of *Cannabis sativa* L. of the Carma variety, with CBGA as predominant, was carried out in 50 mL of hexane for one hour (×3). The part of the extract undissolved in hexane was filtered or decanted, the hexane evaporated down to a volume of 50 mL, and then incubated at 4° C. for 24 hours in order to crystallize CBGA "raw" material. The CBGA "raw" material was vacuum filtered and the collected mother liquors evaporated to a volume of 25 mL, incubated at 4° C. for 24 hours in order to crystallize the CBGA "raw" material. About 0.4 g of CBGA "raw" material was obtained.

The CBGA "raw" material obtained was recrystallized with 5 mL of hexane per gram of CBGA two or three more times to obtain CBGA with a purity greater than 90% and about 95%.

Subsequently, the recrystallized CBGA was purified. To obtain a purity greater than 98%, the recrystallized CBGA was purified by means of countercurrent chromatography (CCC), using the two phase system, Hexane:Ethanol:Water (10:7:3) with the organic phase of hexane as mobile phase. The CBGA was eluted to a K of 3.2-3.5, admitting a load of 0.5 g to 1 g of recrystallized CBGA per 100 mL of CCC coil.

Example 6

Isolation of CBGA Ethanol from Extracts

Maceration of 50.3 g of dried plant material of the Carma variety was extracted with 500 mL ethanol for 1 hour (×3) and the ethanol was evaporated to obtain about 4.7 g of solid extract representing a yield of 9.4%, according to the method disclosed in WO2009043836 or EP2044935 except without the decarboxylation step. Maceration of 4.7 g of extract of *Cannabis sativa* L. of the Carma variety, with CBGA as predominant, was carried out in 50 mL of hexane for one hour. The part of the extract undissolved in hexane was filtered or decanted, the hexane evaporated down to a volume of 40 mL and then incubated at 7° C. for 18 hours in order to crystallize crystallize CBGA "raw" material. About 491 mg of CBGA "raw" material was obtained. The CBGA "raw" material was vacuum filtered and the collected mother liquors evaporated to a volume of 20 mL and then incubated at 7° C. for 5 hours in order to crystallize the CBGA "raw" material. About 300 mg of CBGA "raw" material was obtained. The CBGA "raw" material was vacuum filtered and the collected mother liquors evaporated to a volume of 10 mL and then incubated at 7° C. for 18 hours in order to crystallize the CBGA. About 79 mg of CBGA was obtained. The total amount of CBGA obtained was 870 mg representing a yield of 18.5% from the initial extract used and 1.7% by weight of the initial plant material used. The 870 mg of CBGA obtained was recrystallized with 5 mL of hexane per gram of CBGA two or three more times to obtain CBGA with a purity greater than 90% and about 95%.

Example 7

Isolation of CBGA Ethanol from Extracts

Maceration of 51.0 g of dried plant material of the AIDA variety (CVPO File number: 20160167 from 14-1-16) was extracted by maceration with 500 mL ethanol for 1 hour (×3) and the ethanol was evaporated to obtain about 9.2 g of solid extract representing a yield of 18%, according to the method disclosed in WO2009043836 or EP2044935 except without the decarboxylation step. Maceration of 9.2 g of extract of *Cannabis sativa* L. of the AIDA variety, with CBGA as predominant, was carried out in 50 mL of hexane for one hour. The part of the extract undissolved in hexane was filtered or decanted, the hexane evaporated down to a volume of 40 mL and incubated at 7° C. for 18 hours in order to crystallize crystallize CBGA "raw" material. About 1251 mg of CBGA "raw" material was obtained. The CBGA "raw" material was vacuum filtered and the collected mother liquors evaporated to a volume of 20 mL and then incubated at 7° C. for 18 hours in order to crystallize the CBGA. About 1070 mg of CBGA was obtained. The CBGA was vacuum filtered and the collected mother liquors evaporated to a volume of 10 mL and then incubated at 7° C. for 7 hours in order to crystallize the CBGA. About 70 mg of CBGA was obtained. The total amount of CBGA obtained was 2391 mg representing a yield of 25.9% from the initial extract used and 4.7% by weight of the initial plant material used. The 2391 mg of CBGA "raw" obtained was recrystallized with 5 mL of hexane per gram of CBGA two or three more times to obtain CBGA with a purity greater than 90% and about 95%.

Example 8

Isolation of CBGA Acetone from Extracts

Maceration of 100.3 g of dried plant material of the Carma variety was extracted by maceration with 1000 mL acetone for 1 hour (×3) and the acetone was evaporated to obtain about 11 g of solid extract representing a yield of 11%, according to the method disclosed in WO2009043836 or EP2044935 except without the decarboxylation step. Maceration of 7.7 g of extract of *Cannabis sativa* L. of the Carma variety, with CBGA as predominant, was carried out in 25 mL of hexane for one hour and repeated with 10 mL of hexane. The part of the extract undissolved in hexane was decanted, the hexane evaporated down to a volume of 25 mL and then incubated at 7° C. for 18 hours in order to crystallize crystallize CBGA "raw" material. About 634 mg of CBGA "raw" material was obtained. The CBGA "raw" material was vacuum filtered and the collected mother liquors evaporated to a volume of 17 mL, and then incubated at 7° C. for 18 hours in order to crystallize the CBGA. About 121 mg of CBGA was obtained. The CBGA was vacuum filtered and the collected mother liquors evaporated to a volume of 10 mL and then incubated at 7° C. for 7 hours in order to crystallize the CBGA. About 9 mg of CBGA was obtained. The total amount of CBGA obtained was 764 mg representing a yield of 9.9% from the initial extract used and 1.1% by weight of the initial plant material used. The 870 mg of CBGA obtained was recrystallized with 5 mL of acetone per gram of CBGA two or three more times to obtain CBGA with a purity greater than 90% and about 95%.

Example 9

Isolation of CBGA Acetone from Extracts

Maceration of 100.2 g of dried plant material of the AIDA variety (CVPO File number: 20160167 from 14-1-16) was extracted by maceration with 1000 mL acetone for 1 hour (×3) and the acetone was evaporated obtaining approximately 16.6 g of solid extract representing a yield of 16.6%, according to the method disclosed in WO2009043836 or EP2044935 except without the decarboxylation step. Maceration of 9.8 g of extract of *Cannabis sativa* L. of the AIDA variety, with CBGA as predominant, was carried out in 25 mL of hexane for one hour and repeated with 10 mL of hexane. The part of the extract undissolved in hexane was decanted, the hexane evaporated down to a volume of 35 mL and then incubated at 7° C. for 24 hours in order to crystallize CBGA "raw" material. About 283 mg of CBGA "raw" material was obtained. The CBGA "raw" material was vacuum filtered and the collected mother liquors evaporated to a volume of 20 mL and then incubated at 7° C. for 18 hours in order to crystallize the CBGA. About 1172 mg of CBGA was obtained. The CBGA was vacuum filtered and the collected mother liquors evaporated to a volume of 10 mL and then incubated at 7° C. for 18 hours in order to crystallize the CBGA. About 236 mg of CBGA was obtained. The total amount of CBGA obtained was 1691 mg representing a yield of 17.2% from the initial extract used and 2.8% by weight of the initial plant material used. The 1691 mg of CBGA obtained was recrystallized with 5 mL of hexane per gram of CBGA two or three more times to obtain CBGA with a purity greater than 90% and about 95%.

Example 10

Isolation of CBG from Plant Material

In order to decarboxylate CBGA to CBG, 150 g of *Cannabis sativa* L. of the Carma variety, with CBGA as predominant, was decarboxylated by heating at 120° C. for two hours. A subsequent maceration was carried out in 750 mL of hexane for one hour (×3). The plant material was filtered, the hexane evaporated down to a volume of 100 mL, and then incubated 4° C. for 24 hours in order to crystallize the CBG "raw" material. The CBG "raw" material was vacuum filtered and the collected mother liquors evaporated to a volume of 30 mL to 50 mL and then incubated at 4° C. for 24 hours in order to crystallize the CBG. The amount of CBG obtained in this two step process depends on the concentration of CBG in the starting plant material. The CBG obtained was recrystallized with 5 mL of hexane per gram of CBG two or three more times to obtain CBG with a purity between 95% and 98%.

To achieve a purity greater than 98% the recrystallized CBG was purified by means of countercurrent chromatography (CCC), using the two-phase system, Hexane:Ethanol:Water (120:14:6) or (10:13:7) with the organic phase of hexane as mobile phase. The CBG was eluted to a K of 2 or 1 respectively, admitting a load of 0.5 to 1 g of recrystallized CBG per 100 mL of CCC coil.

Example 11

Isolation of CBG from Plant Material

This experiment was repeated 3 times, the data shown is the mean of the three experiments. In order to decarboxylate CBGA to CBG, 150 g of *Cannabis sativa* L. of the Carma variety, with CBGA as predominant, were decarboxylated by heating at 150° C. for 1 hour. Maceration of 100.5 g of decarboxylated plant material was carried out in 1 L of hexane for one hour. This procedure is repeated two times more with 0.75 L of hexane. The plant material was filtered and the hexane was evaporated down to a volume of 50 mL and then incubated at 4° C. for 72 hours in order to crystallize CBG "raw" material. About 2.24 g of CBG "raw" material was obtained. The CBG "raw" material was vacuum filtered and the collected mother liquors evaporated to a volume of 30 mL and then incubated at −18° C. for 24 hours in order to crystallize the CBG. About 0.26 g of CBG was obtained. The total amount of CBG obtained in this two step process was 2.5 g, representing a yield of 2.48% by weight of the initial decarboxilated plant material used.

2.1 g of the CBG "raw" material obtained was then recrystallized with 12.5 mL of hexane (ratio of about 6 mL of hexane per gram of CBG). The CBG mixture was heated at 40° C. until all CBG "raw" was dissolved and then incubated at 4° C. for 12 hours in order to crystallize CBG. About 1.79 g of CBG was obtained from first recrystallization; an 85% yield from the initial CBG "raw" material. A second recrystallization was performed with 1.77 g of CBG and 13.5 mL of hexane (ratio of about 8 mL of hexane per gram of CBG). The CBG mixture was heated at 40° C. until all CBG was dissolved and then incubated at 4° C. for 12 hours in order to crystallize CBG. About 1.57 g of CBG with a purity of 95% or more was obtained. The yield of the second recrystallization was 86.7% from the first recrystallization CBGA material, or 74.8% of initial CBG "raw" material. A third recrystallization was performed in two of the three experiments with 1.59 g of CBG and 12.5 mL of hexane (ratio of about 8 mL of hexane per gram of CBG). The CBG mixture was heated at 40° C. and then incubated at 4° C. for 12 hours in order to crystallize CBG. About 1.38 g of CBG with a purity of 95% or more was obtained. The yield of the third recrystallization was 86.9% and represented 66.2% yield from initial CBG "raw" material. The total amount of CBG with a purity of 95% or more obtained was from 1.43 g to 1.57 g, representing a yield of 66.2% to 74.8% from the initial CBG "raw" material and 1.4% to 1.5% by weight of the initial decarboxilated plant material used.

Example 12

Isolation of CBG from Plant Material

This experiment was repeated 3 times, the data shown is the mean of the three experiments. In order to decarboxylate CBGA to CBG, 150 g of *Cannabis sativa* L. of the AIDA variety (CVPO File number: 20160167 from 14-1-16), with CBGA as predominant, were decarboxylated by heating at 150° C. for 1 hour. Maceration of 100.4 g of decarboxylated plant material was carried out in 1 L of hexane for one hour. This procedure is repeated two times more with 0.75 L of hexane. The extract was then incubated at 4° C. for 72 hours in order to crystallize CBG "raw" material. About 4.8 g of CBG "raw" material was obtained. The CBG "raw" material was vacuum filtered and the collected mother liquors evaporated to a volume of 30 mL and then incubated at 4° C. for 72 hours in order to crystallize the CBG. About 0.1 g of CBG was obtained. The total amount of CBG obtained in this two step process was 4.9 g, representing a yield of 4.88% by weight of the initial decarboxilated plant material used.

4.77 g of the CBG "raw" material was then recrystallized with 20 mL of hexane (ratio of about 4.2 mL of hexane per gram of CBG). The CBG mixture was heated at 40° C. until the CBG was dissolved and then incubated at 4° C. for 12 hours in order to crystallize CBG. About 4.3 g of CBG was obtained from first recrystallization; a 90.2% yield from the initial CBG "raw" material. A second recrystallization was performed with 4.3 g of CBG and 20 mL of hexane (ratio of about 4.6 mL of hexane per gram of CBG). The CBG mixture was heated at 40° C. until the CBG was dissolved and then incubated at 4° C. for 12 hours in order to crystallize CBG. About 4.12 g of CBG was obtained. The yield of the second recrystallization was 89.5% from the first recrystallization CBG material, or 86.4% of initial CBG "raw" material. A third recrystallization was performed with 4.1 g of CBG and 20 mL of hexane (ratio of about 4.9 mL of hexane per gram of CBG). The CBG mixture was heated at 40° C. until the CBG was dissolved and then incubated at 4° C. for 12 hours in order to crystallize CBG. About 3.85 g of CBG with purity >95% was obtained. The yield of the third recrystallization was 93.9% and represented 80.7% yield from initial CBG "raw" material. The total amount of CBG with a purity of 95% or more obtained was 3.85 g, representing a yield of 80.7% of the initial CBG "raw" material and 3.84% by weight of the initial decarboxilated plant material used.

Example 13

Isolation of CBG from Plant Material

In order to decarboxylate CBGA to CBG, 4 Kg of *Cannabis sativa* L. of the AIDA variety (CVPO File number:

20160167 from 14-1-16), with CBGA as predominant, was decarboxylated by heating at 150° C. for 1 hour. Maceration of 3.65 Kg of decarboxylated plant material was carried out in 25 L of hexane for one hour. This procedure was repeated two times more with 20 L of hexane. The plant material was filtered, the hexane evaporated down to a volume of 2 L, and then incubated at 7° C. for 15 hours in order to crystallize CBG "raw" material. About 75.3 g of CBG "raw" material was obtained. The CBG "raw" material was vacuum filtered and the collected mother liquors evaporated to a volume of 1.5 L and then incubated at 7° C. for 24 hours in order to crystallize the CBG. About 29.2 g of CBG was obtained. The total amount of CBG obtained in this two step process was 4.9 g, representing a yield of 4.88% of initial plant material. The CBG was vacuum filtered a second time and the collected mother liquors evaporated to a volume of 1 L and then incubated at 7° C. for 12 hours in order to crystallize the CBG. About 5.9 g of CBG was obtained. The CBG" was vacuum filtered a third time and the collected mother liquors evaporated to a volume of 0.6 L and then incubated at 7° C. for 24 hours in order to crystallize the CBG. About 10.6 g of CBG was obtained. The total amount of CBG obtained in this four step process was 121 g, representing a yield of 3% from initial plant material used.

110.2 g of the CBG "raw" material was then recrystallized with 335 mL of hexane (ratio of about 3 mL of hexane per gram of CBG). The CBG mixture was heated at 40° C. until the CBG was dissolved and then incubated at 7° C. for 72 hours in order to crystallize CBG. About 87.6 g of CBG was obtained from first recrystallization; a 79.5% yield from the initial CBG "raw" material. A second recrystallization was performed with 77.1 g of CBG and 225 mL of hexane (ratio of about 3 mL of hexane per gram of CBG). The CBG mixture was heated at 40° C. until the CBG was dissolved and then incubated at 7° C. for 2 hours in order to crystallize CBG. About 61.8 g of CBG was obtained. The CBG was vacuum filtered and the collected mother liquors were evaporated down and then incubated at 7° C. for 70 hour in order to crystallize CBG. About 11.6 g of CBG was obtained. The yield of the second recrystallization was 95.2% from the first recrystallization CBG material.

An additional recrystallization was performed with the remaining 9.4 g of CBG from the first recrystallization plus the 11.6 g of CBG from second recrystallization with 210 mL of hexane (ratio of about 10 mL of hexane per gram of CBG). The CBG mixture was heated at 40° C. until the CBG was dissolved and then incubated at 7° C. for 24 hours in order to crystallize CBG. About 19.3 g of CBG was obtained. The yield of the third recrystallization was 91.9% and represented 80.7%. Summing the results of the two second recrystallization indicated that 81.1 g of CBG was obtained and represents a yield of 92.6% or a 73.6% yield from the initial CBG "raw" material.

A third recrystallization was performed with 80.8 g of CBG and 500 mL of hexane (ratio of about 6.2 mL of hexane per gram of CBG). The CBG mixture was heated at 40° C. until the CBG was dissolved and then incubated at ambient temperature (23° C.) for 12 hours in order to crystallize CBG. About 67.2 g of CBG with a purity of 99% or more was obtained. The CBG was vacuum filtered and the collected mother liquors were evaporated down and then incubated at 7° C. for 2 hours in order to crystallize CBG. About 7.9 g of CBG with purity >95% was obtained. The total amount of CBG with a purity of 95% or more obtained in the third recrystallization was 75.1 g with a yield of 92.6% and represents a 68.2% yield from initial CBG "raw" material.

The 10.5 g of CBG obtained in the last crystallization was treated and processed apart, and initially recrystallized with 100 mL of hexane (ratio of about 10 mL of hexane per gram of CBG). The CBG mixture was incubated at 7° C. for 24 hours in order to crystallize CBG. About 7.24 g of CBG was obtained. The yield of the first recrystallization was 69% from the initial CBG "raw" material. A second recrystallization was performed with 7.12 g of CBG and 60 mL of hexane (ratio of about 8.4 mL of hexane per gram of CBG). The CBG mixture was heated at 40° C. until the CBG was dissolved and then incubated at 4° C. for 5 hours in order to crystallize CBG. About 6.55 g of CBG was obtained. The yield of the second recrystallization was 92% from the first recrystallization CBG material, or 62.4% of initial CBG "raw" material. A third recrystallization was performed with 6.55 g of CBG and 60 mL of hexane (ratio of about 9.2 mL of hexane per gram of CBG). The CBG mixture was heated at 40° C. until the CBG was dissolved and then incubated at 4° C. for 5 hours in order to crystallize CBG. About 5.99 g of CBG with a purity of 95% or more was obtained. The yield of the third recrystallization was 91.5% and represented 57% yield from initial CBG "raw" material. The total amount of CBG with a purity of 95% or more obtained was 80.8 g, representing a yield of 66.8% from the initial CBG "raw" material and 2.2% by weight of the initial decarboxilated plant material used. (See FIG. 3 and FIG. 4).

Example 14

Isolation of CBG from Extracts

In order to decarboxylate CBGA to CBG, 150 g of *Cannabis sativa* L. of the Carma variety, with CBGA as predominant, was decarboxylated by heating at 120° C. for two hours. The decarboxylated plant material was extracted by maceration with 750 mL acetone for 1 hour (×3) and the acetone was evaporated to obtain about 12 g of solid extract, according to the method disclosed in WO2009043836 or EP2044935 except without the decarboxylation step. A subsequent maceration of 10 g of the extract of *Cannabis sativa* L. of the Carma variety, with CBG as predominant, was carried out in 50 mL of hexane for one hour (×3). The part of the extract undissolved in hexane was filtered, and the hexane evaporated down to a volume of 50 mL and then incubated at 4° C. for 24 hours in order to crystallize crystallize CBG "raw" material. The CBG "raw" material was vacuum filtered and the collected mother liquors evaporated to a volume of 25 mL and then incubated at 4° C. for 48 hours in order to crystallize the CBG "raw" material. The amount of CBG "raw" material obtained in these two steps depends on CBG concentration in the starting extract.

The CBG "raw" material was then recrystallized with 5 ml of hexane per gram of CBG two or three more times to obtain CBG with a purity of 95% or more.

To obtain a purity greater than 98%, the recrystallized CBG was purified by means of current counter chromatography (CCC), using the two-phase system, Hexane:Ethanol:Water (20:14:6), with the organic phase of hexane as mobile phase. The CBG was eluted to a K of 2-2.5 (20:14:6) or K of 1-1.5 (20:13:7), admitting a load of 0.5 to 1 g of recrystallized CBG per 100 ml of CCC coil.

Example 15

Isolation of CBG from Resin Butane Extracts

1 Kg of *Cannabis sativa* L. of the Carma variety, with CBGA as predominant, were sieved with a 150 μm sieve obtaining 87 g of resin. In order to decarboxylate CBGA to CBG, 87 g of resin of *Cannabis sativa* L. of the Carma variety, with CBGA as predominant, was decarboxylated by heating at 120° C. for two hours. 75 g of the decarboxylated resin was extracted by cold extraction using butane as solvent with 200 g of butane for 20 minutes to 45 minutes (×4). About 11 g of solid resin extract was obtained. A subsequent maceration of 10 g of the butane extract of *Cannabis sativa* L. of the Carma variety, with CBG as predominant, was carried out in 50 mL of hexane for one hour. The resin extract was dissolved and the solution placed at 4° C. for 12 hours in order to crystallize the CBGA "raw" material. About 4.5 mg of CBGA "raw" material was obtained. The collected mother liquors was used to purify other cannabinoids with the counter current chromatography (CCC). The amount of CBG "raw" material represents a yield of 45% from the extract used and 6% by weight of the decarboxilated resin used.

4.5 g of CBG "raw" material was then recrystallized with 50 mL of hexane (ratio of about 10 mL per gram of CBG). The CBG mixture was heated at 40° C. until the CBG was dissolved and then incubated at 4° C. for 12 hours in order to crystallize CBG. This recrystallization step was performed twice. About 3.1 g of CBG with a purity of 95% or more was obtained. The yield of CBG with a purity of 95% or more was 31% from the initial CBG "raw" material and 4.1% by weight of the initial decarboxilated resin used.

To obtain the THC and CBD from the collected mother liquors with a purity greater than 95%, the mother liquors were evaporated and the dry residue purified by means of current counter chromatography (CCC), using the two-phase system, Hexane:Ethanol:Water (10:7:3), with the organic phase of hexane as mobile phase if CBD was the main target compound. The THC was eluted to a K of 0.5 and CBD was eluted to a K of 1-1.5, admitting a load of 1 g to 2 g of dry mother liquors per 100 mL of CCC coil. If THC was the main target compound, the two-phase system used was Hexane:Ethanol:Water (20:17:3), with the organic phase of hexane as mobile phase. The THC was eluted to a K of 1 and CBD was eluted to a K of 2-2.5, admitting a load of 1 g to 2 g of dry mother liquors per 100 mL of CCC coil.

Example 16

Isolation of CBD from Plant Material

This experiment was repeated 2 times, the data shown is the mean of the two experiments. In order to decarboxylate CBDA to CBD, 465 g of *Cannabis sativa* L. of the SARA variety (CVPO File number: 20150098 from 15-1-15), with CBDA as predominant, were decarboxylated by heating at 150° C. for 1 hour. Maceration of 203.6 g of decarboxylated plant material was carried out in 2 L of petroleum ether (40-60° C. bp) for one hour. This maceration procedure was repeated two times with 1.5 L petroleum ether (40-60° C. bp). The plant material was filtered and the petroleum ether was evaporated down to a volume of 120 mL and then incubated at −18° C. for 1 to 2 hours in order to precipitate insoluble material. The solution was vacuum filtered, seeded with 0.1 g of CBD, and incubated at −18° C. for 14 hours in order to crystallize crystallize CBD "raw" material. About 16.3 g of CBD "raw" material was obtained. The CBD "raw" material was vacuum filtered and the collected mother liquors evaporated to a volume of 70 mL and then incubated at −18° C. for 20 hours in order to crystallize the CBD. About 1.4 g of CBD was obtained. The CBD was vacuum filtered and the collected mother liquors evaporated to a volume of 50 mL and then incubated at −18° C. for 48 hours in order to crystallize the CBD. About 1.05 g of CBD was obtained. The CBD was vacuum filtered. The total amount of CBD obtained in this three step process was 18.7 g, representing a yield of 9.2% by weight of the initial decarboxilated plant material used.

In one experiment, the CBD of each crystallization step was processed independently. The 15 g of the CBD obtained in the first crystallization was recrystallized with 22.5 mL of petroleum ether (40-60° C. bp), ratio of about 1.5 mL of petroleum ether per gram of CBD. The CBD mixture was heated at 40° C. until the CBD was dissolved and then incubated at ambient temperature (23° C.) for 12 hours in order to crystallize CBD. About 2.8 g of CBD was obtained. The CBD was vacuum filtered and the collected mother liquors were evaporated down and then incubated at 7° C. for 2 hours in order to crystallize the CBD. About 10.5 g of CBD was obtained. The CBD was vacuum filtered and the collected mother liquors were evaporated down and then incubated at −18° C. for 24 hours in order to crystallize the CBD. About 0.5 g of CBD was obtained. The yield of recrystallized CBD at ambient temperature (23° C.) was 18.7%, while the yield of recrystallized CBD at 7° C. is 70%.

A second recrystallization was performed with 8.3 g of CBD obtained at 7° C. after wash with cold petroleum ether with 8.5 ml of petroleum ether (40-60° C. bp), ratio of about 1 mL of petroleum ether per gram of CBD. The CBD was heated at 40° C. until the CBD was dissolved and then incubated at ambient temperature (23° C.) for 12 hours in order to crystallize CBD. About 4.6 g of CBD was obtained. The CBD material was vacuum filtered and the collected mother liquors evaporated down and then incubated at 7° C. for 2 hours in order to crystallize the CBD. About 1.0 g of CBD was obtained. The yield of the second recrystallization at ambient temperature (23° C.) was 55.4%, and the yield of recrystallization at 7° C. is 12.7%. Both together represents a yield of 58.1%.

A third recrystallization was performed with 4.6 g of CBD and 5 mL of petroleum ether (40-60° C. bp), ratio of about 1 mL of petroleum ether per gram of CBD. The CBD was heated at 40° C. until the CBD was dissolved and then incubated at ambient temperature (23° C.) for 12 hours in order to crystallize CBD. About 3.6 g of CBD was obtained. After filtering the CBD, the collected mother liquors were evaporated down and then incubated at 7° C. for 2 hours in order to crystallize CBD. About 0.7 g of CBD was obtained.

2.4 g of CBD obtained in the second crystallization was recrystallized with 2.5 mL of petroleum ether (40-60° C. bp), ratio of about 1 mL of petroleum ether per gram of CBD. The CBD mixture was heated at 40° C. until the CBD was dissolved and then incubated at 4° C. for 12 hours in order to crystallize CBD. About 1.3 g of CBD was obtained. After filtering the CBD, the collected mother liquors were evaporated down and then incubated at 7° C. for 2 hours in order to crystallize CBD material. About 0.6 g of CBD was obtained. The yield of the first recrystallization at ambient temperature (23° C.) was 54.2%, and the yield of recrystallization at 7° C. is 25%.

0.8 g of CBD obtained in the third crystallization was recrystallized with 1 mL of petroleum ether (40-60° C. bp), ratio of about 1.25 mL of petroleum ether per gram of CBD. The CBD mixture was heated at 40° C. until the CBD "raw" was dissolved and then incubated at ambient temperature (23° C.) for 12 hours in order to crystallize CBD. About 0.5 g of CBD was obtained. After filtering the CBD, the collected mother liquors were evaporated down and then incubated at 7° C. for 2 hours in order to crystallize CBD. About 0.2 g of CBD was obtained. The yield of the first recrystallization at ambient temperature (23° C.) was 54.2%, and the yield of recrystallization at 7° C. is 25%. The yield of the first recrystallization at ambient temperature (23° C.) is 62.5%, and the yield of recrystallization at 7° C. is 25%.

The CBD recrystallized at ambient temperature (23° C.) from all 3 crystallization steps plus the CBD obtained at 7° C. from first and second crystallization steps were pooled together (9.1 g) and this CBD amount was recrystallized for second time with 10 mL of petroleum ether (40-60° C. bp), ratio of about 1 mL of petroleum ether per gram of CBD. The CBD mixture was heated at 40° C. until the CBD was dissolved and then incubated at ambient temperature (23° C.) for 12 hours in order to crystallize CBD. About 7.0 g of CBD was obtained. After filtering the CBD, the collected mother liquors were evaporated down and then incubated at 7° C. for 2 hours in order to crystallize CBD. About 1.4 g of CBD was obtained. The yield of the first recrystallization at ambient temperature (23° C.) was 54.2%, and the yield of recrystallization at 7° C. is 25%. The yield of the first recrystallization at ambient temperature (23° C.) is 62.5%, and the yield of recrystallization at 7° C. is 25%.

The CBD recrystallized at 7° C. from the third crystallization and second recrystallization steps plus the CBD obtained at −18° C. from first crystallization step were pooled together (3.5 g) and this CBD amount was recrystallized for second time with 3.5 mL of petroleum ether (40-60° C. bp), ratio of about 1 mL of petroleum ether per gram of CBD. The CBD mixture was heated at 40° C. until the CBD was dissolved and then incubated at ambient temperature (23° C.) for 12 hours in order to crystallize CBD. About 2.8 g of CBD was obtained. After filtering the CBD, the collected mother liquors were evaporated down and then incubated at 7° C. for 2 hours in order to crystallize CBD. About 0.5 g of CBD was obtained.

A third and last recrystallization was performed with the CBD obtained at ambient temperature (23° C.) from the two second recrystallizations (9.3 g) and this amount of CBD was recrystallized with 10 mL of petroleum ether (40-60° C. bp), ratio of about 1 mL of petroleum ether per gram of CBD. The CBD mixture was heated at 40° C. until the CBD was dissolved and then incubated at ambient temperature (23° C.) for 5 hours in order to crystallize CBD. About 7.3 g of CBD with purity of 98.3% was obtained. After filtering the CBD, the collected mother liquors were evaporated down and then incubated at 7° C. for 2 hours in order to crystallize CBD. About 1.4 g of CBD was obtained. The yield of the third recrystallization at ambient temperature (23° C.) was 78.5%, and the yield of recrystallization at 7° C. was 15%. The total amount of CBD with a purity of 95% or more was 7.3 g with a yield of 78.5%, and representing 40.5% yield from initial CBD "raw" material and a yield of 3.6% by weight of the initial decarboxilated plant material used.

In the second experiment, 17.6 g of the CBD "raw" material was recrystallized with 13.5 mL of petroleum ether (40-60° C. bp), ratio of about 0.75 mL of petroleum ether per gram of CBD. The CBD mixture was heated at 40° C. until the CBD was dissolved and then incubated at ambient temperature (23° C.) for 7 hours in order to crystallize CBD. About 8.5 g of CBD was obtained. After filtering the CBD, the collected mother liquors were evaporated down and then incubated at 7° C. for 2 hours in order to crystallize CBD. About 6.5 g of CBD was obtained. The yield of the recrystallization at ambient temperature (23° C.) is 48.3%, and the yield of recrystallization at 7° C. is 36.9%.

A second recrystallization was performed with 6.5 g of CBD obtained at 7° C. and 4.8 mL of petroleum ether (40-60° C. bp), ratio of about 0.75 mL of petroleum ether per gram of CBD. The CBD mixture was heated at 40° C. until the CBD was dissolved and then incubated at ambient temperature (23° C.) for 48 hours in order to crystallize CBD. About 4.1 g of CBD was obtained. After filtering the CBD, the collected mother liquors were evaporated down and then incubated at 7° C. for 2 hours in order to crystallize CBD material. About 1.3 g of CBD was obtained. The yield of the recrystallization at ambient temperature (23° C.) was 63%, and the yield of recrystallization at 7° C. is 20%. Wth the 8.5 g and 4.1 g of CBD from the recrystallizations at ambient temperature (23° C.) a second recrystallization was performed with 9.75 mL of petroleum ether (40-60° C. bp), ratio of about 1.5 mL of petroleum ether per gram of CBD. The CBD mixture was heated at 40° C. until the CBD was dissolved and then incubated at ambient temperature (23° C.) for 3 hours in order to crystallize CBD. About 9.4 g of CBD was obtained. After filtering the CBD, the collected mother liquors were evaporated down and then incubated at 7° C. for 3 hours in order to crystallize CBD. About 2.1 g of CBD was obtained. The yield of the second recrystallization at ambient temperature (23° C.) is 74.6%, and the yield of recrystallization at 7° C. is 16.7%. Both together represents a yield of 91.3%. The amount of the second recrystallization at ambient temperature (23° C.) was 9.4 g with yield of 53.4% of the initial CBD "raw" material.

A third recrystallization was performed with 12.6 g of CBD and 19 mL of petroleum ether (40-60° C. bp), ratio of about 1.5 mL of petroleum ether per gram of CBD. The CBD mixture was heated at 40° C. until the CBD was dissolved and then incubated at 7° C. for 2 hours in order to crystallize CBD material. About 11.7 g of CBD with purity of 97.5% was obtained. The total amount of CBD with a purity of 95% or more obtained in the was 11.7 g with a yield of 93.6% and represents 61.5% yield from initial CBD "raw" material and a yield of 5.7% by weight of the initial decarboxilated plant material used.

Example 17

Isolation of CBD from Plant Material

In order to decarboxylate CBDA to CBD, 1 Kg of *Cannabis sativa* L. of the SARA variety (CVPO File number: 20150098 from 15-1-15), with CBDA as predominant, were decarboxylated by heating at 150° C. for 1 hour. Maceration of 880 g of decarboxylated plant material was carried out in 10 L of petroleum ether (40-60° C. bp) for one hour. This procedure was repeated two times with 7.5 L of petroleum ether (40-60° C. bp). The plant material was filtered and the petroleum ether was evaporated down to a volume of 850 mL and incubated at −18° C. for 1 to 2 hours in order to precipitate insoluble material. The solution was vacuum filtered, seeded with 0.1 g of CBD, and incubated at −18° C. for 16 hours in order to crystallize crystallize CBD "raw" material. About 24 g of CBD "raw" material was obtained. The CBD "raw" material was vacuum filtered and the collected mother liquors evaporated to 450 mL and then incubated at −18° C. for 16 hours in order to crystallize the CBD "raw" material. About 13.2 g of CBD "raw" material was obtained. The CBD "raw" material was vacuum filtered and the collected mother liquors evaporated to a volume of 210 mL and then incubated at −18° C. for 24 hours in order to crystallize CBD. About 12.3 g of CBD was obtained. The CBD was vacuum filtered and the collected mother liquors evaporated to a volume of 110 mL and then incubated at −18° C. for 96 hours in order to crystallize the CBD. About 10.8 g of CBD was obtained. The CBD was vacuum filtered. The total amount of CBD obtained in this four step process was 60.3 g, representing a yield of 6.8% by weight of the initial decarboxylated plant material used.

44.7 g of the CBD "raw" material was then washed with 100 mL of cold (−18° C.) petroleum ether (40-60° C. bp) and filtered to obtain 34.4 g of CBD "washed" material. 100 mL of the wash was evaporated to a volume of 20 mL and incubated at −18° C. in order to crystallize the CBD. About 4.4 g of CBD was obtained. 34.4 g of CBD "washed" material was recrystallized with 35 mL of petroleum ether (40-60° C. bp), ratio of about 1 mL of petroleum ether per gram of CBD. The CBD mixture was heated at 40° C. until the CBD was dissolved and then incubated at ambient temperature (23° C.) for 14 hours in order to crystallize CBD. About 11 g of CBD was obtained. The CBD was vacuum filtered and the collected mother liquors were evaporated down and then incubated at 7° C. for 12 hours in order to crystallize the CBD. About 16.3 g of CBD was obtained. The CBD was vacuum filtered and the collected mother liquors were evaporated down and then incubated at −18° C. for 72 hours in order to crystallize the CBD. About 3.1 g of CBD was obtained.

A second recrystallization was performed with the 16.3 g of the CBD obtained in the first recrystallization at 7° C. solving with 10 mL of petroleum ether (40-60° C. bp), ratio of about 0.6 mL of petroleum ether per gram of CBD. The CBD was heated at 40° C. until the CBD was dissolved and then incubated at ambient temperature (23° C.) for 3 hours in order to crystallize CBD. About 11.6 g of CBD was obtained. The CBD material was vacuum filtered and the collected mother liquors were evaporated down and then incubated at 7° C. for 2 hours in order to crystallize the CBD. About 3.3 g of CBD was obtained. The CBD material was vacuum filtered and the collected mother liquors were evaporated down and then incubated at −18° C. for 48 hours in order to crystallize the CBD. About 0.7 g of CBD was obtained.

A first recrystallization was performed on 6.7 g of CBD "raw" material obtained with 5 mL of petroleum ether (40-60° C. bp), ratio of about 0.75 mL of petroleum ether per gram of CBD. The CBD was heated at 40° C. until the CBD was dissolved and then incubated at ambient temperature (23° C.) for 4 hours in order to crystallize CBD. About 1.9 g of CBD was obtained. The CBD material was vacuum filtered and the collected mother liquors were evaporated down and then incubated at 7° C. for 2 hours in order to crystallize the CBD. About 3.1 g of CBD was obtained. The CBD material was vacuum filtered and the collected mother liquors were evaporated down and then incubated at −18° C. for 48 hours in order to crystallize the CBD. About 0.8 g of CBD was obtained.

A first recrystallization was performed on 6.6 g of CBD "raw" material obtained with 4.7 mL of petroleum ether (40-60° C. bp), ratio of about 0.7 mL of petroleum ether per gram of CBD. The CBD was heated at 40° C. until the CBD was dissolved and then incubated at ambient temperature (23° C.) for 14 hours in order to crystallize CBD. About 1.2 g of CBD was obtained. The CBD material was vacuum filtered and the collected mother liquors mixed with 1.5 mL of petroleum ether (40-60° C. bp) and then incubated at 7° C. for 2 hours in order to crystallize the CBD. About 3.5 g of CBD was obtained. The CBD material was vacuum filtered and the collected mother liquors were evaporated down and then incubated at −18° C. for 36 hours in order to crystallize the CBD. About 0.65 g of CBD was obtained.

The last 2.3 g of CBD "raw" material was pooled with the 4.4 g of the CBD from the wash and the 3.3 g and 3.1 g of CBD obtained in the first recrystallizations at 7° C. 12.8 g of this CBD pool was recrystallized with 6.4 mL of petroleum ether (40-60° C. bp), ratio of about 0.5 mL of petroleum ether per gram of CBD. The CBD was heated at 40° C. until the CBD was dissolved and then incubated at ambient temperature (23° C.) for 2.5 hours in order to crystallize CBD. About 4.4 g of CBD was obtained. The collected mother liquor was decanted in a new vessel and placed at ambient temperature (23° C.) for 1.5 hours in order to crystallize CBD. About 3.9 g of CBD was obtained. The total CBD obtained at ambient temperature (23° C.) after 4 hours was 8.3 g. The CBD material was vacuum filtered and the collected mother liquors were evaporated down and then incubated at 7° C. for 2 hours in order to crystallize the CBD. About 0.9 g of CBD was obtained.

A second recrystallization was performed with 24.4 g of CBD obtained from the first recrystallizations at ambient temperature (23° C.) and 15.6 mL of petroleum ether (40-60° C. bp), ratio of about 0.65 mL of petroleum ether per gram of CBD. The CBD was heated at 40° C. until the CBD was dissolved and then incubated at ambient temperature (23° C.) for 36 hours in order to crystallize CBD. About 21.8 g of CBD was obtained. The CBD material was vacuum filtered and the collected mother liquors were evaporated down and then incubated at 7° C. for 3 hours in order to crystallize the CBD. About 1.1 g of CBD was obtained. The CBD material was vacuum filtered and the collected mother liquors were evaporated down and then incubated at −18° C. for 6 hours in order to crystallize the CBD. About 0.8 g of CBD was obtained. The yield of the recrystallization at ambient temperature (23° C.) is 89.3%, and the yield of recrystallization at 7° C. is 4.5%. Both together represents a yield of 93.8%.

The remainder of CBD obtained from the first recrystallizations at 7° C. (3.5 g+1.1 g) and the second recrystallization (2.6 g) was pooled to obtain 7.2 g of CBD that was recrystallized for second time with 5 mL of petroleum ether (40-60° C. bp), ratio was 0.7 mL of petroleum ether per gram of CBD. The CBD was heated at 40° C. until the CBD was dissolved and then incubated at ambient temperature (23° C.) for 3 hours in order to crystallize CBD. About 5.6 g of CBD was obtained. The CBD material was vacuum filtered and the collected mother liquors were evaporated down and then incubated at 7° C. for 12 hours in order to crystallize the CBD. About 1.1 g of CBD was obtained. The yield of the recrystallization at ambient temperature (23° C.) is 77.8%, and the yield of recrystallization at 7° C. is 15.3%. Both together represents a yield of 93.1%. The total amount of the second recrystallization at ambient temperature (23° C.) was 27.4 g with yield of 45% of the initial CBD "raw" material.

A third recrystallization was performed with 27.4 g of CBD obtained in the second recrystallization at 23° C. and 8.3 g and 1.2 g of the remaining CBD obtained in the first recrystallizations at 23° C. 36.1 g of this pooled CBD amount was recrystallized with 27 mL of petroleum ether (40-60° C. bp), ratio of about 0.75 mL of petroleum ether per gram of CBD. The CBD was heated at 40° C. until the CBD was dissolved and then incubated at ambient temperature (23° C.) for 12 hours in order to crystallize CBD. About 31.9 g of CBD with a purity of 95% or more was obtained. The CBD material was vacuum filtered and the collected mother liquors were evaporated down and then incubated at 7° C. for 2 hours in order to crystallize the CBD. About 3.1 g of CBD with purity 92.5% was obtained. The total amount of CBD with a purity of 95% or more obtained in the third recrystallization was 31.9 g with a yield of 88.4%, representing 52.9% yield from initial CBD "raw" material and a yield of 3.6% by weight of the initial decarboxilated plant material used. (See FIG. 5 and FIG. 6).

Example 18

Isolation of CBD from Plant Material

In order to decarboxylate CBDA to CBD, 1.5 Kg of *Cannabis sativa* L. of the PILAR variety (CVPO File number: 20160115 from 14-1-16), with CBDA as predominant, were decarboxylated be heating at 150° C. for 1 hour. Maceration of 1.28 Kg of decarboxylated plant material was carried out in 10 L of petroleum ether (40-60° C. bp) for one hour. This procedure was repeated two times with 7.5 L of petroleum ether (40-60° C. bp). The plant material was filtered and the petroleum ether evaporated down to a volume of 300 mL and then incubated at −18° C. for 1 to 2 hours in order to precipitate insoluble material. The solution was vacuum filtered, seeded with 1 g of CBD, and incubated at −18° C. for 48 hours in order to crystallize crystallize CBD "raw" material. About 22.3 g of CBD "raw" material was obtained. The CBD "raw" material was vacuum filtered and the collected mother liquors evaporated to a volume of 150 mL and then incubated at −18° C. for 48 hours in order to crystallize the CBD. About 3.8 g of CBD was obtained. The CBD was vacuum filtered. The total amount of CBD obtained in this two step process was 26.2 g, representing a yield of 2% by weight of the initial decarboxilated plant material used.

22.2 g of the CBD "raw" material was then recrystallized with 33 mL of petroleum ether (40-60° C. bp), ratio of about 1.5 mL of petroleum ether per gram of CBD. The CBD mixture was heated at 40° C. until the CBD was dissolved and then incubated at 7° C. for 48 hours in order to crystallize CBD. About 16.3 g of CBD was obtained. 3.8 g of the CBD "raw" material was then recrystallized with 5.7 mL of petroleum ether (40-60° C. bp), ratio of about 1.5 mL of petroleum ether per gram of CBD. The CBD mixture was heated at 40° C. until the CBD was dissolved and then incubated at 7° C. for 5 hours in order to crystallize CBD. About 2.3 g of CBD was obtained. The yield of the first recrystallization was 71.5% from the initial CBD "raw" material.

A second recrystallization was performed with 15 g of CBD and 22.5 mL of petroleum ether (40-60° C. bp), ratio was 1.5 mL of petroleum ether per gram of CBD. The CBD mixture was heated at 40° C. until the CBD was dissolved and then incubated at ambient temperature (23° C.) for 48 hours in order to crystallize CBD. About 8.3 g of CBD was obtained. The CBD was vacuum filtered and the collected mother liquors were evaporated down and then incubated at 7° C. for 2 hours in order to crystallize the CBD. About 4.9 g of CBD was obtained. The yield of the recrystallization at ambient temperature (23° C.) was 37%, and the yield of recrystallization at 7° C. was 21.8%. Both together represent a yield of 58.8%.

Wth the 2.3 g of CBD from the first recrystallization at 7° C. and the 4.9 g obtained in the second recrystallization at 7° C. another recrystallization was performed with 10.5 mL of petroleum ether (40-60° C. bp), ratio of about 1.5 mL of petroleum ether per gram of CBD. The CBD mixture was heated at 40° C. until the CBD was dissolved and then incubated at ambient temperature (23° C.) for 18 hours in order to crystallize CBD. About 4 g of CBD was obtained. The CBD was vacuum filtered and the collected mother liquors were evaporated down and then incubated at 7° C. for 18 hours in order to crystallize the CBD. About 2.6 g of CBD was obtained. The yield of the recrystallization at ambient temperature (23° C.) is 56.3%, and the yield of recrystallization at 7° C. is 36.6%. Both together represent a yield of 92.9%. The total amount of the second recrystallization at ambient temperature (23° C.) was 12.3 g with yield of 47.3% from the initial CBD "raw" material used.

A third recrystallization was performed with 12.1 g of CBD and 12 mL petroleum ether (40-60° C. bp), ratio was 1 mL of petroleum ether per gram of CBD. The CBD mixture was heated at 40° C. until the CBD was dissolved and then incubated at ambient temperature (23° C.) for 18 hours in order to crystallize CBD. About 9.8 g of CBD with purity of 95.1% was obtained. The CBD was vacuum filtered and the collected mother liquors were evaporated down and then incubated at 7° C. for 2 hours in order to crystallize the CBD. About 1.9 g of CBD with purity of 95.1% was obtained. The total amount of CBD with a purity of 95% or more obtained in the third recrystallize at was 11.7 g, representing a yield of 45% from the CBD "raw" material used and 0.9% by weight of the initial decarboxilated plant material used.

Example 19

Isolation of CBD from Ethanol Extracts

In order to decarboxylate CBDA to CBD, 150 g of *Cannabis sativa* L. of the Futura 75 variety, with CBDA/CBD as predominant, were decarboxylated be heating at 150° C. for 1 hour. 100.1 g of the decarboxylated plant material was extracted by maceration with 750 mL ethanol for 1 hour (×3) and the ethanol was evaporated obtaining about 5.8 g of solid extract, according to the method disclosed in WO2009043836 or EP2044935 except without the decarboxylation step. A subsequent maceration of 1.8 g of the extract of *Cannabis sativa* L. of the Futura 75 variety, with CBD as predominant, was carried out in 20 mL of petroleum ether (40-60° C. bp) for one hour. The part of the extract undissolved in petroleum ether was filtered, and the petroleum ether evaporated down to a volume of 15 mL and then incubated at −18° C. for 24 hours in order to crystallize CBD "raw" material. About 34 mg of CBD "raw" material was obtained. The CBD "raw" material was vacuum filtered and the collected mother liquors evaporated to a volume of 7 mL and then incubated at −18° C. for 48 hours in order to crystallize the CBD "raw" material. About 48 mg of CBD "raw" material was obtained. The total amount of CBD "raw" material obtained in this two step process was 159 mg representing a yield of 8.8% from initial ethanol extraction used and 0.46% by weight of the initial decarboxylated plant material used.

The 159 mg of CBD "raw" material was then recrystallized with 1.5 mL of petroleum ether (40-60° C.) bp per gram of CBD two or three more times at ambient temperature (23° C.) to obtain CBD with a purity over 95%.

Example 20

Isolation of CBD from Ethanol Extracts

In order to decarboxylate CBDA to CBD, 150 g of *Cannabis sativa* L. of the PILAR variety (CVPO File number: 20160115 from 14-1-16), with CBDA/CBD as predominant, were decarboxylated by heating at 150° C. for 1 hour. 50.3 g of the decarboxylated plant material was extracted by maceration with 500 mL ethanol for 1 hour (×3) and the ethanol was evaporated obtaining approximately 4.9 g of solid extract representing a yield of 9.8%, according to the method disclosed in WO2009043836 or EP2044935. A subsequent maceration of 4.9 g of the extract of *Cannabis sativa* L. of the PILAR variety, with CBD as predominant, was carried out in 35 mL of petroleum ether (40-60° C. bp) for one hour. The part of the extract undissolved in petroleum ether was filtered, the petroleum ether evaporated down to a volume of 15 mL, chilled to −18° C., seeded with 25 mg CBD and then incubated at −18° C. for 24 hours in order to crystallize the CBD "raw" material. About 1040 mg of CBD "raw" material was obtained. The CBD "raw" material was vacuum filtered and the collected mother liquors evaporated to a volume of 8 mL and then incubated at −18° C. for 12 hours in order to crystallize the CBD "raw" material. About 152 mg of CBD "raw" material was obtained. The mother liquors were evaporated down to a volume of 4 mL and incubated at −18° C. for 24 hours in order to crystallize the CBD "raw" material. About 45 mg of CBD "raw" material was obtained. The total amount of CBD "raw" obtained in this three step process was 1237 mg, representing a yield of 25.2% from initial ethanol extraction used and 2.46% by weight of the initial decarboxylated plant material used.

The 1.2 g of CBD "raw" material was then recrystallized with 1.5 mL of petroleum ether (40-60° C. bp) per gram of CBD two or three more times at ambient temperature (23° C.) to obtain CBD with a purity 95% or more.

Example 21

Isolation of CBD from Acetone Extracts

In order to decarboxylate CBDA to CBD, 101.3 g of *Cannabis sativa* L. of the 60.2/1/9 experimental variety, with CBDA/CBD as predominant, were decarboxylated by hydrodestilation process staying under 100° C. for 2 hour. The plant material was dried by heating at 50° C. for 12 hours. 88.6 g of the decarboxylated plant material was extracted by maceration with 750 mL acetone for 1 hour (×3) and the acetone was evaporated to obtain about 12.6 g of solid extract, according to the method disclosed in WO2009043836 or EP2044935 except the decarboxylation step was modified. A subsequent maceration of 5 g of the extract of *Cannabis sativa* L. of the 600.2/1/9 experimental variety, with CBD as predominant, was carried out in 50 mL of petroleum ether (40-60° C. bp) for one hour under agitation. The part of the extract undissolved in petroleum ether was filtered, the petroleum ether evaporated down to a volume of 30 mL, chilled to −18° C., seeded with 50 mg CBD and then incubated at −18° C. for 36 hours in order to crystallize the CBD "raw" material. After one wash with cold petroleum ether (40-60° C. bp), about 219 mg of CBD "raw" material was obtained. The CBD "raw" material was vacuum filtered and the collected mother liquors evaporated to a volume of 20 mL and then incubated at −18° C. for 72 hours in order to crystallize the CBD "raw" material. After one wash with cold petroleum ether (40-60° C. bp), about 493 mg of CBD "raw" material was obtained. The CBD "raw" material was vacuum filtered and the collected mother liquors evaporated to a volume of 20 mL and then incubated at −18° C. for 24 hours in order to crystallize the CBD "raw" material. After one wash with cold petroleum ether (40-60° C. bp), about 209 mg of CBD "raw" material was obtained.

The total amount of CBD "raw" and "washed" material obtained in the three step process was 921 mg, representing a yield of 18.4% from initial acetone extraction used and 2.6% by weight of the initial decarboxylated plant material used.

The 921 mg of CBD "raw" material was then recrystallized with 1 mL of petroleum ether (40-60° C. bp) per gram of CBD two or three more times to obtain CBD with a purity over 95%.

Example 22

Isolation of CBD from Acetone Extracts

In order to decarboxylate CBDA to CBD, 100 g of *Cannabis sativa* L. of the SARA variety (CVPO File number: 20150098 from 15-1-15), with CBDA/CBD as predominant, were decarboxylated in the hydrodestilation process staying under 100° C. for 2.5 hours. The plant material was dried by heating at 50° C. for 12 hours. 88.8 g of the decarboxylated plant material was extracted by maceration with 750 mL acetone for 1 hour (×3) and then evaporating the acetone to obtain 15 g of solid extract, according to the method disclosed in WO2009043836 or EP2044935 except the decarboxylation step was modified. A subsequent maceration of 7.9 g of the extract of *Cannabis sativa* L. of the SARA variety, with CBD as predominant, was carried out in 50 mL of petroleum ether (40-60° C. bp) for one hour under agitation. The part of the extract undissolved in petroleum ether was filtered, the petroleum ether evaporated down to a volume of 30 mL, chilled to −18° C., seeded with 50 mg CBD and then incubated at −18° C. for 24 hours in order to crystallize the CBD "raw" material. After one wash with cold petroleum ether (40-60° C. bp), about 727 mg of CBD "raw" material was obtained. The CBD "raw" material was vacuum filtered and the collected mother liquors evaporated to a volume of 15 mL and then incubated at −18° C. for 24 hours in order to crystallize the CBD "raw" material. After one wash with cold petroleum ether (40-60° C. bp), about 149 mg of CBD "raw" material was obtained. The total amount of CBD "raw" and "washed" material obtained in the three step process was 1.4 g, representing a yield of 17.7% from initial acetone extraction used and 3% by weight of the initial decarboxylated plant material used.

The 1.4 g of CBD "washed" material was then recrystallized with 3 mL of petroleum ether (40-60° C. bp), ratio was 2 mL of petroleum ether per gram of CBD. The CBD mixture was heated at 40° C. until the CBD was dissolved and then incubated at 7° C. for 12 hours in order to crystallize CBD. After one wash with cold petroleum ether (40-60° C. bp), about 1.13 g of CBD was obtained. The yield of the first recrystallization was 80.7% from the initial CBD "raw" material.

A second recrystallization was performed with 1.13 g of CBD and 2 mL plus 1 mL wash of petroleum ether (40-60° C. bp), ratio of about 2.6 mL of petroleum ether per gram of CBD. The CBD mixture was heated at 40° C. at 40° C. until the CBD was dissolved and then incubated at 7° C. for 12 hours in order to crystallize CBD. The mother liquors were decanted and the crystalline mass of CBD was recrystallized for third time with 1.5 mL of petroleum ether (40-60° C. bp), ratio of about 1-1.5 mL of petroleum ether per gram of CBD. The solution was incubated at ambient temperature (23° C.) for 12 hours in order to crystallize CBD. About 0.8 g of CBD with a purity of 95% or more was obtained. After filtering the mother liquors were evaporated down and then incubated at 7° C. for 12 hours in order to crystallize CBD.

About 0.2 g of CBD with a purity of 90% or more was obtained. The yield of the third recrystallization at ambient temperature (23° C.) is 57.1%, and the yield of recrystallization at 7° C. is 14.3% from initial CBD "washed" material. Both together represents a yield of 71.4%. The total amount of CBD with a purity of 95% or more obtained in the third recrystallization was 0.8 g, representing a yield of 57.1% from initial CBD "raw" material and a yield of 10.1% from the initial acetone extraction and 1.7% by weight of the initial decarboxylated plant material used.

Example 23

Isolation of CBD from Acetone Extracts 100 g of the dried plant material of *Cannabis sativa* L. of the SARA variety (CVPO File number: 20150098 from 15-1-15), with CBDA as predominant, was extracted by maceration with 750 mL acetone for 1 hour (×3) and the acetone was evaporated to obtain about 18.1 g of solid extract, according to the method disclosed in WO2009043836 or EP2044935 except without the decarboxylation step. In order to decarboxylate CBDA to CBD, 10 g of acetone extract were decarboxylated by heating at 150° C. for 2 hours, resulting in 6.7 g of decarboxylated extract. A subsequent maceration of the 6.7 g was carried out in 50 mL of petroleum ether (40-60° C. bp) for one hour under agitation. The part of the extract undissolved in petroleum ether was filtered, the petroleum ether evaporated down to a volume of 20 mL, chilled to −18° C., seeded with 50 mg CBD and then incubated at −18° C. for 48 hours in order to crystallize the CBD "raw" material. About 1.6 g of CBD "raw" material was obtained. The CBD "raw" material was vacuum filtered and the collected mother liquors evaporated to a volume of 15 mL and then incubated at −18° C. for 78 hours in order to crystallize the CBD "raw" material. About 0.1 g of CBD "raw" material was obtained. The mother liquors were evaporated down to a volume of 4 mL and incubated at −18° C. for 24 hours in order to crystallize the CBD "raw" material. About 45 mg of CBD "raw" material was obtained. The total amount of CBD "raw" obtained in this three step process was 2.1 g, representing a yield of 21% from initial acetone extraction used, 31.3% of the decarboxylated extraction used and 2.1% by weight of the initial plant material used.

The 1.5 g of CBD "raw" material was then was recrystallized with 3 mL of petroleum ether (40-60° C. bp), ratio of about 2 mL of petroleum ether per gram of CBD. The CBD mixture was heated at 40° C. until the CBD was dissolved and then incubated at 7° C. for 12 hours in order to crystallize CBD. About 1.3 g of CBD was obtained. The yield of the first recrystallization was 86.7% from the initial CBD "raw" material.

A second recrystallization was performed with 1.3 g of CBD and 3 mL of petroleum ether (40-60° C. bp), ratio of about 2.3 mL of petroleum ether per gram of CBD. The CBD mixture was heated at 40° C. until the CBD was dissolved and then incubated at 7° C. for 12 hours in order to crystallize CBD. About 1.14 g of CBD with a purity of 90% or more was obtained. The yield of the second recrystallization was 87.7% and 76% from the initial CBD "raw" material. The mother liquors of both recrystallizations were evaporated to 3 mL and placed at 7° C. for 48 hours in order to crystallize CBD. About 0.3 g of CBD was obtained.

The CBD of the second and third crystallization steps, the CBD recovered from the mother liquors and the CBD from the two recrystallization were pooled together (1.9 g) and recrystallized with 4 mL of petroleum ether (40-60° C. bp), ratio of about 2 mL of petroleum ether per gram of CBD. The CBD mixture was heated at 40° C. until the CBD was dissolved and then incubated at 7° C. for 12 hours in order to crystallize CBD. About 1.6 g of CBD was obtained. The yield of the recrystallization can be considered 84.2% from the first recrystallization and 76.2% from the initial CBD "raw" material.

1.6 g and recrystallized with 3 mL of petroleum ether (40-60° C. bp), ratio of about 2 mL of petroleum ether per gram of CBD. The CBD mixture was heated at 40° C. until the CBD was dissolved and then incubated at 7° C. for 12 hours in order to crystallize CBD. About 1.4 g of CBD with a purity of 90% or more was obtained. The yield of the second recrystallization that was 87.5% and 66.7% from the initial CBD "raw" material.

1.4 g of CBD was recrystallized for a third time with 2 mL of petroleum ether (40-60° C. bp), ratio of about 1.5 mL of petroleum ether per gram of CBD. The solution was incubated at ambient temperature (23° C.) for 12 hours in order to crystallize CBD. About 1 g of CBD with a purity of 95% or more was obtained. After filtering the mother liquors were evaporated down and then incubated at 7° C. for 12 hours in order to crystallize CBD. About 0.3 g of CBD with a purity of 90% or more was obtained. The yield of the third recrystallization at ambient temperature (23° C.) is 71.4%, and the yield of recrystallization at 7° C. is 21.4%, and 47.6% and 14.3% respectively from initial CBD "raw" material. The total amount of CBD with a purity of 95% or more obtained in the third recrystallization was 1 g with a yield of 47.6% from initial CBD "raw" material, a yield of 10% from the initial acetone extraction used, 15% from the initial decarboxylated acetone extraction used, and 1% by weight of the initial plant material used.

Example 24

Isolation of CBD from Acetone Extracts

This experiment was repeated twice and the data shown is the mean of both. 100.7 g of the dried plant material of *Cannabis sativa* L. of the 60.2/1/9 experimental variety, with CBDA as predominant, was extracted by maceration with 750 mL acetone for 1 hour (×3) and the acetone was evaporated to obtain about 15.3 g of solid extract, according to the method disclosed in WO2009043836 or EP2044935 except without the decarboxylation step. In order to decarboxylate CBDA to CBD, 5 g of acetone extract was decarboxylated by heating at 150° C. for 1 hour, resulting in 3.8 g of decarboxylated extract. A subsequent maceration of the 3.8 g of the decarboxylated acetone extract was carried out in 40 mL of petroleum ether (40-60° C. bp) for one hour under agitation. The part of the extract undissolved in petroleum ether was filtered, the petroleum ether evaporated down to a volume of 20 mL, chilled to −18° C., seeded with 50 mg CBD and then incubated at −18° C. for 18 hours in order to crystallize the CBD "raw" material. About 0.95 g of CBD "raw" material was obtained. The CBD "raw" material was vacuum filtered and the collected mother liquors evaporated to a volume of 20 mL and then incubated at −18° C. for 72 hours in order to crystallize the CBD "raw" material. About 0.25 g of CBD "raw" material was obtained. The mother liquors were evaporated down to a volume of 10 mL and incubated at −18° C. for 78 hours in order to crystallize the CBD "raw" material. About 0.18 g of CBD "raw" material was obtained. The total amount of CBD "raw" obtained in this three step process was 1.4 g, representing a yield of 28% from initial acetone extraction used, 36.8% from the decarboxylated extraction used and a yield of 4.3% by weight of the initial plant material used.

1.3 g of CBD "raw" material was then recrystallized with 2.6 mL of petroleum ether (40-60° C. bp), ratio of about 2 mL of petroleum ether per gram of CBD. The CBD mixture was heated at 40° C. until the CBD was dissolved and then incubated at 7° C. for 12 hours in order to crystallize CBD. The mother liquors were then decanted and the crystalline mass of CBD was recrystallized for second time with 2 mL of petroleum ether (40-60° C. bp), ratio of about 1.5-2 mL of petroleum ether per gram of CBD. The CBD mixture was heated at 40° C. until the CBD was dissolved and then incubated at ambient temperature (23° C.) for 1 hour in order to crystallize CBD. About 0.6 g of CBD with a purity of 95% or more was obtained. After filtering, the mother liquors were evaporated down and then incubated at 7° C. for 12 hours in order to crystallize CBD. About 0.3 g of CBD with a purity of 90% or more was obtained. The yield of the third recrystallization at ambient temperature (23° C.) was 46.1%, and the yield of recrystallization at 7° C. is 23.1% from initial CBD "raw" material. The total amount of CBD with a purity of 95% or more obtained in the second recrystallization was 0.6 g with a yield of 46.1% from initial CBD "raw" material, 12% from the initial acetone extraction used, 15.8% from the initial decarboxylated acetone extraction used and 1.8% by weight of the initial plant material used.

Example 25

Isolation of CBD from Acetone Extracts 100.2 g of the dried plant material of *Cannabis sativa* L. of the PILAR variety (CVPO File number: 20160115 from 14-1-16), with CBDA as predominant, was extracted by maceration with 750 mL acetone for 1 hour (×3) and the acetone was evaporated to obtain about 11.8 g of solid extract, according to the method disclosed in WO2009043836 or EP2044935 except without the decarboxylation step. In order to decarboxylate CBDA to CBD, 5 g of acetone extract were decarboxylated by heating at 150° C. for 1 hour, resulting in 2.8 g of decarboxylated extract. A subsequent maceration of the 2.8 g of the decarboxylated acetone extract was carried out in 25 ml of petroleum ether (40-60° C. bp) for one hour under agitation. The part of the extract undissolved in petroleum ether was filtered, the petroleum ether evaporated down to a volume of 15 mL, chilled to −18° C., seeded with 25 mg CBD and then incubated at −18° C. for 18 hours in order to crystallize the CBD "raw" material. About 0.3 g of CBD "raw" material was obtained. The CBD "raw" material was vacuum filtered and the collected mother liquors evaporated to a volume of 10 mL and then incubated at −18° C. for 72 hours in order to crystallize the CBD "raw" material. About 0.13 g of CBD "raw" material was obtained. The mother liquors were evaporated down to a volume of 4 mL and incubated at −18° C. for 78 hours in order to crystallize the CBD "raw" material. About 0.14 g of CBD "raw" material was obtained. The total amount of CBD "raw" obtained in this three step process was 0.58 g, representing a yield of 20.7% from the decarboxylated extraction used.

0.58 g of CBD "raw" material was then recrystallized with 1.5 mL of petroleum ether (40-60° C. bp), ratio of about 3 mL of petroleum ether per gram of CBD. The CBD mixture was heated at 40° C. until the CBD was dissolved and then incubated at 7° C. for 12 hours in order to crystallize CBD. The mother liquors were then decanted and the crystalline mass of CBD was recrystallized for second time with 1 mL of petroleum ether (40-60° C. bp), ratio of about 2 mL of petroleum ether per gram of CBD. The CBD mixture was heated at 40° C. at 40° C. until the CBD was dissolved and then incubated at ambient temperature (23° C.) for 12 hour in order to crystallize CBD. About 0.36 g of CBD with a purity of 95% or more was obtained. After filtering, the mother liquors were evaporated down and then incubated at 7° C. for 12 hours in order to crystallize CBD. About 0.05 g of CBD with a purity of 90% or more was obtained. The yield of the second recrystallization at ambient temperature (23° C.) is 46.1%, and the yield of recrystallization at 7° C. is 23.1% from initial CBD "raw" material. The total amount of CBD with a purity of 95% or more obtained in the second recrystallization was 0.6 g with a yield of 62.1% from initial CBD "raw" material and a yield of 12.9% from the initial decarboxilated acetone extraction used.

Example 26

Isolation of CBGA from Plant Material with Only Washing the Crystallized CBGA, without Recrystallization Isolation of CBGA from Plant Material Maceration of 4000 g of plant material of *Cannabis sativa* L. of the AIDA variety (CVPO File number: 20160167 from 14-1-16), with CBGA as predominant at 6% concentration, was carried out in 25 L of hexane for one hour. This procedure is repeated two times more with 20 L of hexane. The plant material was filtered and the hexane was evaporated down to a volume of 2500 mL and then incubated at 25° C. for 5 hours in order to crystallize CBGA "raw" material. About 103 g of CBGA "raw" material was obtained. The CBGA "raw" material was vacuum filtered and the collected mother liquors evaporated to a volume of 1400 mL and incubated at 4° C. for 12 hours in a reactor of 3 L with agitation in order to crystallize the CBGA "raw" material. About 40 g of CBGA "raw" material was obtained. The total amount of CBGA "raw" material obtained in this two-step process was 143 g, representing a yield of 3.6% by weight of the initial plant material used.

101 g of the CBGA "raw" material was then washed with 500 mL of hexane (ratio of about 5 mL of hexane per gram of CBGA). The CBGA mixture was heated at 35° C. in a reactor with agitation for 5 minutes and filtered in order to obtain the CBGA. This process was repeated twice and 85 g of CBGA with a purity of 97% was obtained. The same washing process was performed with the 40 g CBGA "raw" obtained from the mother liquors using 200 mL of hexane. About 18 g of CBGA with a purity of 96% was obtained. The total amount of CBGA with a purity of 95% or more obtained was 103 g, representing a yield of 72% from the CBGA "raw" material used and 2.6% by weight of the initial plant material used. Wth only a washing process of the CBGA "raw", CBGA with a purity over 95% was obtained.

Example 27

Isolation of CBG of Plant Material Using Reactors with Agitation and Cleaning Process with Ethanol at the End Isolation of CBG from Plant Material In order to decarboxylate CBGA to CBG, 4.3 Kg of *Cannabis sativa* L. of the AIDA variety (CVPO File number:

20160167 from 14-1-16), with CBGA as predominant at 6% of concentration, was decarboxylated by heating at 150° C. for 2 hour. Maceration of 3.97 Kg of decarboxylated plant material was carried out in 25 L of hexane for one hour. This procedure was repeated two times more with 20 L of hexane. The plant material was filtered, the hexane evaporated down to a volume of 2.5 L, and then incubated at 4° C. for 5 hours in a 3 L reactor with agitation in order to crystallize CBG "raw" material. About 122.6 g of CBG "raw" material was obtained. The CBG "raw" material was vacuum filtered and the collected mother liquors evaporated to a volume of 1.25 L and then incubated at 4° C. for 5 hours in a reactor with agitation in order to crystallize the CBG. About 7.8 g of CBG was obtained. The CBG "raw" material was vacuum filtered and the collected mother liquors evaporated to a volume of 0.625 L and then incubated at 4° C. for 12 hours in a reactor with agitation in order to crystallize the CBG. About 96.3 g of CBG was obtained. The total amount of CBG obtained in this three step process was 226.7 g, representing a yield of 5.7% of initial plant material.

128 g of the CBG "raw" material was then recrystallized with 640 mL of hexane (ratio of about 5 mL of hexane per gram of CBG). The CBG mixture was heated at 40° C. until the CBG was dissolved and then incubated at 4° C. in a 1 L reactor with agitation for 2 hours in order to crystallize CBG. About 103.2 g of CBG was obtained from first recrystallization; 80.6% yield from the initial CBG "raw" material. Another first recrystallization was performed with resting 95.8 g of CBG "raw" from the third crystallization and 300 mL of hexane (ratio of about 3 mL of hexane per gram of CBG). The CBG mixture was heated at 40° C. until the CBG was dissolved and then incubated at 4° C. in a 1 L reactor for 2 hours in order to crystallize CBG. About 48.1 g of CBG was obtained. The yield of the second first recrystallization was 50.1% from the CBG "raw" used.

A second recrystallization was performed with 102.4 g of CBG from the first recrystallization with 310 mL of hexane (ratio of about 3 mL of hexane per gram of CBG). The CBG mixture was heated at 40° C. until the CBG was dissolved and then incubated at 4° C. in a 1 L reactor with agitation for 2 hours in order to crystallize CBG. About 92.5 g of CBG was obtained. The yield of the second recrystallization was 90.3% and represented 72.2% from the CBG "raw used. Another second recrystallization was performed with the 48.1 g of CBG from the third crystallization and 150 mL of hexane (ratio of about 3 mL of hexane per gram of CBG). The CBG mixture was heated at 40° C. until the CBG was dissolved and then incubated at 4° C. in a 1 L reactor for 2 hours in order to crystallize CBG. About 44.4 g of CBG was obtained. The yield of the second recrystallization was 92.3% and represented a 46.3% from the CBG "raw" used.

A third recrystallization was performed with 92.5 g of CBG and 300 mL of hexane (ratio of about 3 mL of hexane per gram of CBG). The CBG mixture was heated at 40° C. until the CBG was dissolved and then incubated at 4° C. in a 1 L reactor with agitation for 2 hours in order to crystallize CBG. About 91 g of CBG with a purity of 92.1% was obtained. The yield of the third recrystallization was 98.4% and represented a 71.1% from the CBG "raw" used. Another third recrystallization was performed with 43.9 g of CBG from the third crystallization and 150 mL of hexane (ratio of about 3 mL of hexane per gram of CBG). The CBG mixture was heated at 40° C. until the CBG was dissolved and then incubated at 4° C. in a 1 L reactor for 2 hours in order to crystallize CBG. About 42.8 g of CBG a purity of 91.6% was obtained. The yield of the second third recrystallization was 97.6% and represented a 44.7% from the CBG "raw" used.

As the total of 133.8 g of CBG obtained do not reach the 95% purity we treated it with special washing process by dissolving it in 670 mL of 100% ethanol, filtered and the mother liquors obtained evaporated to dryness to obtain 116.2 g of CBG as an oil. 116.2 g of the CBG "oil" material was then recrystallized with 360 mL of hexane (ratio of about 3 mL of hexane per gram of CBG). The CBG mixture was heated at 40° C. until the CBG was dissolved and then incubated at 4° C. in a 1 L reactor with agitation for 2 hours in order to crystallize CBG. About 92.1 g of CBG with a purity of 99.3% was obtained, representing 71.9% yield from the initial CBG "raw" material and a 2.3% yield from the initial decarboxylated plant material.

Example 28

Isolation CBD from Plant Material Via Dry Extract Decarboxylated After, Using Reactors with Agitation with the Steps of Impurity Filtration and Seedling Isolation of CBD from Plant Material Maceration of 4.85 Kg of plant material of the experimental variety H6 from 2015 harvest with 6.4% of CBD was carried out in 25 L of petroleum ether (40-60° C. bp) for one hour. This procedure was repeated two times with 20 L of petroleum ether (40-60° C. bp). The plant material was filtered and the petroleum ether evaporated down completely to achieve 703 g of dry extract. This 703 g of extract was decarboxylated at 150° C. for 2 hours obtaining 687 g of decarboxylated extract. The extract was dissolved with a volume of 2061 mL and then incubated at −18° C. in a reactor with agitation for 2 hours in order to precipitate insoluble material. The solution was vacuum filtered obtaining 10 g of insoluble material, seeded with 0.5 g of CBD, and incubated at −18° C. in a 3 L reactor with agitation for 2 hours in order to crystallize CBD "raw" material. About 146.1 g of CBD "raw" material was obtained. The CBD "raw" material was vacuum filtered and the collected mother liquors and incubated at −18° C. in a 3 L reactor with agitation for 12 hours in order to crystallize the CBD. About 53 g of CBD "raw" was obtained. The CBD was vacuum filtered. The total amount of CBD obtained in this two-step process was 199.1 g, representing a yield of 4.1% by weight of the initial plant material used.

194.5 g of the CBD "raw" material was then recrystallized with 585 mL of petroleum ether (40-60° C. bp), ratio of about 3 mL of petroleum ether per gram of CBD. The CBD mixture was heated at 40° C. until the CBD was dissolved and then incubated at 4° C. in a 1 L reactor with agitation for 2 hours in order to crystallize CBD. About 141.1 g of CBD was obtained. The yield of the first recrystallization was 72.5% from the initial CBD "raw" material.

A second recrystallization was performed with 126.3 g of CBD and 380 mL of petroleum ether (40-60° C. bp), ratio was 3 mL of petroleum ether per gram of CBD. The CBD mixture was heated at 40° C. until the CBD was dissolved and then incubated at 4° C. in a 1 L reactor with agitation for 2 hours in order to crystallize CBD. About 113.3 g of CBD was obtained. The yield of the recrystallization at 4° C. was 89.7%. The total amount of the second recrystallization was a yield of 63.6% from the initial CBD "raw" material used.

A third recrystallization was performed with 110 g of CBD and 330 mL petroleum ether (40-60° C. bp), ratio was 3 mL of petroleum ether per gram of CBD. The CBD mixture was heated at 40° C. until the CBD was dissolved and then incubated at 15° C. in a 1 L reactor with agitation for 1 hours in order to crystallize CBD. About 81 g of CBD with purity of 99.3% was obtained. The CBD was vacuum filtered and the collected mother liquors were incubated at 4° C. in a 1 L reactor with agitation for 2 hours in order to crystallize the CBD. About 16.4 g of CBD with a purity of 95.1% was obtained. The total amount of CBD with a purity of 95% or more obtained in the third recrystallization was 97.4 g, representing a yield of 48.9% from the CBD "raw" material used and 2% by weight of the initial plant material used.

Example 29

Isolation of CBD from Plant Material Via Dry Extract Decarboxylated after, Using Reactors with Agitation without the Steps of Impurity Filtration and without Seedling Isolation of CBD from Plant Material Maceration of 4.08 Kg of plant material of the experimental variety H6 from 2016 harvest with 3.1% of CBD was carried out in 25 L of petroleum ether (40-60° C. bp) for one hour. This procedure was repeated two times with 25 L of petroleum ether (40-60° C. bp). The plant material was filtered and the petroleum ether evaporated down completely to achieve 410 g of dry extract. This 410 g of extract was decarboxylated at 150° C. for 2 hours obtaining 370 g of decarboxylated extract. The extract was dissolved with a volume of 1110 mL and then incubated at −18° C. in a 3 L reactor with agitation for 12 hours in order to crystallize CBD "raw" material. About 105.7 g of CBD "raw" material was obtained. The CBD "raw" material was vacuum filtered and the collected mother liquors and incubated at −18° C. in a 3 L reactor with agitation for 12 hours in order to crystallize the CBD. About 2 g of CBD "raw" was obtained. The CBD was vacuum filtered. The total amount of CBD obtained in this two-step process was 107.7 g, representing a yield of 2.6% by weight of the initial plant material used.

102.9 g of the CBD "raw" material was then recrystallized with 309 mL of petroleum ether (40-60° C. bp), ratio of about 3 mL of petroleum ether per gram of CBD. The CBD mixture was heated at 40° C. until the CBD was dissolved and then incubated at 4° C. in a 1 L reactor with agitation for 2 hours in order to crystallize CBD. About 79.9 g of CBD was obtained. The yield of the first recrystallization was 77.7% from the initial CBD "raw" material.

A second recrystallization was performed with 73.6 g of CBD and 225 mL of petroleum ether (40-60° C. bp), ratio was 3 mL of petroleum ether per gram of CBD. The CBD mixture was heated at 40° C. until the CBD was dissolved and then incubated at 4° C. in a 1 L reactor with agitation for 2 hours in order to crystallize CBD. About 65.6 g of CBD was obtained. The yield of the recrystallization at 4° C. was 89%. The total amount of the second recrystallization was a yield of 63.7% from the initial CBD "raw" material used.

A third recrystallization was performed with 62 g of CBD and 330 mL petroleum ether (40-60° C. bp), ratio was 3 mL of petroleum ether per gram of CBD. The CBD mixture was heated at 40° C. until the CBD was dissolved and then incubated at 15° C. in a 1 L reactor with agitation for 1 hours in order to crystallize CBD. About 47.1 g of CBD with purity of 97.5% was obtained. The CBD was vacuum filtered and the collected mother liquors were incubated at 4° C. in a 1 L reactor with agitation for 2 hours in order to crystallize the CBD. About 6.9 g of CBD with purity of 95.2% was obtained. The total amount of CBD with a purity of 95% or more obtained in the third recrystallization was 54 g, representing a yield of 52.5% from the CBD "raw" material used and 1.3% by weight of the initial plant material used.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A method of purifying one or more cannabinoids from a plant material, the method consisting essentially of the following steps:
   a) incubating the plant material with a non-polar solvent selected from the group consisting of petroleum ether, pentane and hexane to form a first solvent mixture which extracts the one or more cannabinoids from a plant material;
   b) reducing the volume of the first solvent mixture to about 50% or less of the original volume of the first solvent mixture in step (a) thereby concentrating the one or more cannabinoids;
   c) incubating the reduced first solvent mixture at a temperature range of between about −70° C. to about 40° C. to crystalize the one or more cannabinoids;

d) incubating the one or more crystalized cannabinoids with the non-polar solvent, wherein the non-polar solvent is the same non-polar solvent as in step (a) to form a second solvent mixture, thereby dissolving at least 50% of the one or more crystalized cannabinoids; and e) incubating the second solvent mixture at a temperature range of between about −70° C. to about 40° C. to crystalize the one or more cannabinoids, and f) washing the crystallized one or more cannabinoids by dissolving in ethanol, methanol, isopropylic alcohol or acetone, filtering, evaporating to dryness and recrystallizing using the same non-polar solvent as in step a), thereby resulting in the purification of one or more cannabinoids.

2. The method according to claim 1, wherein recovery of one or more crystalized cannabinoids of step (c) is performed prior to step (d).

3. The method according to claim 2, wherein the recovery is performed using filtration that results in collection of a crystalline product and a mother liquor.

4. The method according to claim 3, further comprising incubating the mother liquor at a temperature range of between about −70° C. to about 40° C. to crystalize the one or more cannabinoids.

5. The method according to claim 4, further comprising after step e) and before step f), the steps of:
e1) recovering the one or more crystalized cannabinoids using filtration that results in a collection of a crystalline product and a mother liquor; and
e2) incubating the mother liquor at a temperature range of between about −70° C. to about 40° C. to crystalize the one or more cannabinoids.

6. The method according to claim 5, wherein steps e1) and e2) are repeated at least once.

7. The method according to claim 1, wherein steps (d) and (e) or steps (b) and (c) are repeated at least once.

8. The method according to claim 1, wherein the first solvent mixture of step (a) is purified prior to step (b) or (c).

9. The method according to claim 1, wherein prior to step (a), the one or more cannabinoids present in the plant material are decarboxylated by heating the plant material.

10. The method according to claim 1, further comprising performing liquid:liquid chromatography after one or more of steps (b) or (d).

11. The method of claim 1, wherein after step c) the crystallized one or more cannabinoids are washed by being dissolved in ethanol, methanol, isopropylic alcohol or acetone, filtered, evaporated to dryness and recrystallized using the same non-polar solvent as in step a).

12. The method of claim 7, wherein after each repeated step e) the crystallized one or more cannabinoids are washed by being dissolved in ethanol, methanol, isopropylic alcohol or acetone, filtered, evaporated to dryness and recrystallized using the same non-polar solvent as in step a).

13. The method of claim 7, wherein after each repeated steps c) and e) the crystallized one or more cannabinoids are washed by being dissolved in ethanol, methanol, isopropylic alcohol or acetone, filtered, evaporated to dryness and recrystallized using the same non-polar solvent as in step a).

14. The method of claim 9, wherein after step c) the crystallized one or more cannabinoids are washed by being dissolved in ethanol, methanol, isopropylic alcohol or acetone, filtered, evaporated to dryness and recrystallized using the same non-polar solvent as in step a).

15. The method of claim 1, wherein the non-polar solvent is hexane or petroleum ether.

16. The method of claim 1, wherein after step e) the crystallized one or more cannabinoids are washed with the non-polar solvent and filtered to obtain a a crystalline product and a mother liquor.

17. The method of claim 16, wherein the wash and filtration are repeated one or more times.

18. A method of purifying a cannabinoid from a plant material, the method consisting essentially of the following steps:
a) incubating the plant material with a solvent selected from the group consisting of pentane, hexane, heptane, cyclohexane, petroleum ethers, dicloromethane, tricloromethane, tethrahydrofurane, diethyl ether, ethanol, methanol, isopropanol, acetone, acetonitrile, ethyl acetate, butane, propane, refrigerant gas 1,1,1,2-Tetrafluoroethane (R134a), liquid $CO_2$, subcritical $CO_2$ or supercritical $CO_2$ or mixes of these solvents to form a first solvent mixture which extracts the one or more cannabinoids from a plant material;

b) filtering, decanting or centrifuging the first solvent mixture;

c) reducing the volume of the first solvent mixture to dryness thereby concentrating the one or more cannabinoids in a first extract;

d) incubating the first extract with a non-polar solvent selected from the group consisting of petroleum ether, pentane and hexane to form a second solvent mixture which extracts the one or more cannabinoids from the first extract;

e) filtering, decanting or centrifuging the second solvent mixture;

f) incubating the second solvent mixture at a temperature range of between about −70° C. to about 40° C. to crystalize the one or more cannabinoids;

g) collecting the one or more crystalized cannabinoids in step (f) using filtration that results in a collection of a crystalline product and a mother liquor;

h) incubating the one or more crystalized cannabinoids of step (g) with the non-polar solvent wherein the non-polar solvent is the same non-polar solvent as in step (d) to form a third solvent mixture, wherein the third solvent mixture dissolves at least 50% of the one or more crystalized cannabinoids;

i) incubating the third solvent mixture at a temperature range of between about −70° C. to about 40° C. to crystalize the one or more cannabinoids, and then washing the crystallized one or more cannabinoids by dissolving in ethanol, methanol, isopropylic alcohol or acetone, filtering, evaporating to dryness and recrystallizing using the same non-polar solvent as in step d); and j) collecting the one or more crystalized cannabinoids of step (i) using filtration that results in a collection of a crystalline product and a mother liquor, thereby resulting in the purification of one or more cannabinoids.

19. The method according to claim 18, wherein the mother liquor of step (g) and/or step (j) is incubated at a temperature range of between about −70° C. to about 40° C. to crystalize the one or more cannabinoids.

20. The method according to claim 19, further comprising
k) collecting the one or more crystalized cannabinoids using filtration that results in a collection of crystals and a mother liquor; and
l) incubating the mother liquor at a temperature range of between about −70° C. to about 40° C. to crystalize the one or more cannabinoids.

21. The method according to claim 20, wherein steps (k) and (l) are repeated at least once.

22. The method according to claim 18, wherein steps (h) and (i) are repeated at least once.

23. The method according to claim 18, wherein step (h) (i) and (j) are repeated at least once.

24. The method according to claim 18, wherein the first solvent mixture of step (a) is purified prior to step (b).

25. The method according to claim 18, wherein prior to step (a), the one or more cannabinoids present in the plant material are decarboxylated by heating.

26. The method according to claim 18, wherein after step (c), the one or more cannabinoids present in the plant material are decarboxylated by heating.

27. The method according to claim 18, further comprising performing liquid:liquid chromatography after one or more of steps (c) (g) or (j).

28. The method of claim 18, wherein after step f) the crystallized one or more cannabinoids are washed by being dissolved in ethanol, methanol, isopropylic alcohol or acetone, filtered, evaporated to dryness and recrystallized using the same non-polar solvent as in step a).

29. The method of claim 18, wherein after step c) and before step d) the one or more cannabinoids in a first extract are washed by being dissolved in ethanol, methanol, isopropylic alcohol or acetone, filtered, evaporated to dryness and after step f) the crystallized one or more cannabinoids are washed by being dissolved in ethanol, methanol, isopropylic alcohol or acetone, filtered, evaporated to dryness and recrystallized using the same non-polar solvent as in step a).

30. The method of claim 23, wherein after step f) the crystallized one or more cannabinoids are washed by being dissolved in ethanol, methanol, isopropylic alcohol or acetone, filtered, evaporated to dryness and recrystallized using the same non-polar solvent as in step a).

31. The method of claim 23, wherein after step c) and before step d) the one or more cannabinoids in a first extract are washed by being dissolved in ethanol, methanol, isopropylic alcohol or acetone, filtered, evaporated to dryness and after step f) the crystallized one or more cannabinoids are washed by being dissolved in ethanol, methanol, isopropylic alcohol or acetone, filtered, evaporated to dryness and recrystallized using the same non-polar solvent as in step a).

32. The method of claim 25, wherein after step f) the crystallized one or more cannabinoids are washed by being dissolved in ethanol, methanol, isopropylic alcohol or acetone, filtered, evaporated to dryness and recrystallized using the same non-polar solvent as in step a).

33. The method of claim 25, wherein after step c) and before step d) the one or more cannabinoids in a first extract are washed by being dissolved in ethanol, filtered, evaporated to dryness and after step f) the crystallized one or more cannabinoids are washed by being dissolved in ethanol, methanol, isopropylic alcohol or acetone, filtered, evaporated to dryness and recrystallized using the same non-polar solvent as in step a).

34. The method of claim 18, wherein the solvent in step a) is hexane or petroleum ether.

35. The method of claim 1, wherein the cannabinoid is THCA or THC.

36. The method of claim 18, wherein the cannabinoid is THCA or THC.

37. The method of claim 1, wherein the cannabinoid is CBDA or CBD.

38. The method of claim 18, wherein the cannabinoid is CBDA or CBD.

39. The method of claim 1, wherein the cannabinoid is CBGA or CBG.

40. The method of claim 18, wherein the cannabinoid is CBGA or CBG.

41. The method of claim 1, wherein in step f) the crystallized one or more cannabinoids are washed by being dissolved in ethanol.

42. The method of claim 18, wherein in step i) the crystallized one or more cannabinoids are washed by being dissolved in ethanol.

* * * * *